US009534202B2

(12) United States Patent
Pecora et al.

(10) Patent No.: US 9,534,202 B2
(45) Date of Patent: *Jan. 3, 2017

(54) COMPOSITIONS AND METHODS FOR TREATING PROGRESSIVE MYOCARDIAL INJURY DUE TO A VASCULAR INSUFFICIENCY

(75) Inventors: Andrew L. Pecora, Wyckoff, NJ (US); Robert A. Preti, Ridgefield, NJ (US)

(73) Assignee: Amorcyte, Inc., Hackensack, NJ (US)

( * ) Notice: Subject to any disclaimer, the term of this patent is extended or adjusted under 35 U.S.C. 154(b) by 184 days.

This patent is subject to a terminal disclaimer.

(21) Appl. No.: 13/285,466

(22) Filed: Oct. 31, 2011

(65) Prior Publication Data
US 2012/0064045 A1    Mar. 15, 2012

Related U.S. Application Data

(60) Continuation of application No. 12/910,328, filed on Oct. 22, 2010, now abandoned, and a continuation-in-part of application No. 12/629,361, filed on Dec. 2, 2009, and a continuation-in-part of application No. 11/552,396, filed on Oct. 24, 2006, now Pat. No. 7,794,705, and a continuation-in-part of application No. 12/401,291, filed on Mar. 10, 2009, now Pat. No. 8,088,370, which is a division of application No. 11/552,396, filed on Oct. 24, 2006, now Pat. No. 7,794,705.

(60) Provisional application No. 61/254,539, filed on Oct. 23, 2009, provisional application No. 60/734,151, filed on Nov. 7, 2005, provisional application No. 61/119,552, filed on Dec. 3, 2008, provisional application No. 61/169,850, filed on Apr. 16, 2009.

(51) Int. Cl.
*A61K 35/28* (2015.01)
*C12N 5/02* (2006.01)
*C12N 5/0789* (2010.01)

(52) U.S. Cl.
CPC ................... *C12N 5/0647* (2013.01)

(58) Field of Classification Search
None
See application file for complete search history.

(56) References Cited

U.S. PATENT DOCUMENTS

| | | | |
|---|---|---|---|
| 5,206,222 A * | 4/1993 | Forman et al. | 514/46 |
| 5,628,761 A * | 5/1997 | Rizik | 606/170 |
| 5,750,397 A | 5/1998 | Tsukamoto et al. | |
| 5,922,674 A * | 7/1999 | Anagnostou et al. | 424/604 |
| 5,980,887 A | 11/1999 | Isner et al. | |
| 6,287,265 B1 | 9/2001 | Gleason | |
| 6,569,082 B1 * | 5/2003 | Chin | 600/37 |
| 6,569,428 B1 | 5/2003 | Isner et al. | |
| 6,569,434 B1 | 5/2003 | Bayne et al. | |
| 6,676,937 B1 | 1/2004 | Isner et al. | |
| 6,933,134 B2 | 8/2005 | Bayne et al. | |
| 7,101,708 B1 | 9/2006 | Lapidot et al. | |
| 7,135,171 B2 | 11/2006 | Edelberg et al. | |
| 7,172,758 B2 | 2/2007 | Colb et al. | |
| 7,268,205 B2 * | 9/2007 | Williams et al. | 528/354 |
| 7,470,538 B2 | 12/2008 | Laughlin et al. | |
| 7,919,315 B2 | 4/2011 | Zeiher et al. | |
| 2002/0061587 A1 | 5/2002 | Anversa | |
| 2002/0098167 A1 | 7/2002 | Anversa et al. | |
| 2002/0142457 A1 | 10/2002 | Umezawa et al. | |
| 2002/0172663 A1 | 11/2002 | Palasis | |
| 2003/0054973 A1 | 3/2003 | Anversa | |
| 2003/0059414 A1 | 3/2003 | Ho et al. | |
| 2003/0109420 A1 * | 6/2003 | Valkirs et al. | 514/2 |
| 2003/0113304 A1 | 6/2003 | Burkhoff | |
| 2003/0148512 A1 | 8/2003 | Fanslow, III et al. | |
| 2003/0199464 A1 | 10/2003 | Itescu | |
| 2003/0232050 A1 | 12/2003 | Isner et al. | |
| 2004/0058412 A1 | 3/2004 | Ho et al. | |
| 2004/0067218 A1 | 4/2004 | Casteilla et al. | |
| 2004/0076619 A1 | 4/2004 | Anversa et al. | |
| 2004/0131585 A1 | 7/2004 | Itescu | |
| 2004/0136966 A1 | 7/2004 | Anversa et al. | |
| 2004/0136973 A1 | 7/2004 | Huberman et al. | |
| 2004/0197310 A1 | 10/2004 | Sanberg et al. | |
| 2004/0209821 A1 * | 10/2004 | Hamann et al. | 514/19 |
| 2004/0219136 A1 | 11/2004 | Hariri | |
| 2004/0247564 A1 | 12/2004 | Itescu | |
| 2004/0258670 A1 | 12/2004 | Laughlin et al. | |

(Continued)

FOREIGN PATENT DOCUMENTS

| | | |
|---|---|---|
| JP | 2006/115771 | 5/2006 |
| JP | 2008-126087 | 6/2008 |

(Continued)

OTHER PUBLICATIONS

"Plan" and "Treatment." Taber's Cyclopedic Medical Dictionary (18th ed.) 1997. (Philadelphia: F.A. Davis Co.; Thomas CL, ed.). pp. 1487 and 1990.*
"Chronic," "adverse," and "consequence." Definitions from Merriam-Webster's Online Dictionary, available at <http://www.merriam-webster.com/>, accessed Feb. 27, 2015. 3 pages.*
Abrahamsen JF et al. 2002. Cryopreserving human peripheral blood progenitor cells with 5-percent rather than 10-percent DMSO results in less apoptosis and necrosis in CD34+ cells. Transfusion 42: 1573-1580.*
Debrunner M et al. 2008. Proinflammatory cytokines in acute myocardial infarction with and without cardiogenic shock. Clin Res Cardiol 97: 298-305.*

(Continued)

*Primary Examiner* — Allison Fox
(74) *Attorney, Agent, or Firm* — Chiesa Shahinian & Giantomasi PC

(57) ABSTRACT

The described invention provides methods and regimens for treating adverse consequences of a persistent and progressive myocardial injury-due to a vascular insufficiency that occurs early or late in a subject in need thereof, and progressive myocardial injury-preventing compositions that contain a chemotactic hematopoietic stem cell product, and, optionally, an additional active agent.

29 Claims, 3 Drawing Sheets

(56) References Cited

U.S. PATENT DOCUMENTS

| | | |
|---|---|---|
| 2005/0069527 A1 | 3/2005 | Laughlin et al. |
| 2005/0095228 A1 | 5/2005 | Fraser et al. |
| 2005/0129663 A1 | 6/2005 | Fulga et al. |
| 2005/0232905 A1 | 10/2005 | Yeh |
| 2005/0233992 A1 | 10/2005 | Itescu |
| 2006/0008450 A1 | 1/2006 | Verfaillie et al. |
| 2006/0193836 A1 | 8/2006 | Rudd |
| 2006/0239983 A1 | 10/2006 | Anversa |
| 2007/0059288 A1 | 3/2007 | Dinsmore et al. |
| 2007/0065417 A1 | 3/2007 | Chancellor et al. |
| 2007/0077201 A1 | 4/2007 | Reading et al. |
| 2007/0105217 A1 | 5/2007 | Pecora et al. |
| 2007/0190127 A1 | 8/2007 | Zhou |
| 2008/0118977 A1 | 5/2008 | Henon |
| 2010/0143317 A1 | 6/2010 | Pecora et al. |
| 2011/0076255 A1 | 3/2011 | Pecora et al. |
| 2012/0059357 A1 | 3/2012 | Pecora et al. |
| 2012/0071855 A1 | 3/2012 | Pecora et al. |
| 2012/0076760 A1 | 3/2012 | Pecora et al. |

FOREIGN PATENT DOCUMENTS

| | | |
|---|---|---|
| JP | 2009514950 A | 4/2009 |
| JP | 2009522209 A | 6/2009 |
| WO | 93/25216 | 12/1993 |
| WO | 95/05843 | 3/1995 |
| WO | 98/19712 | 5/1998 |
| WO | 99/37751 | 7/1999 |
| WO | 99/61584 | 12/1999 |
| WO | 00/06704 | 2/2000 |
| WO | 00/12683 | 3/2000 |
| WO | 01/32842 | 5/2001 |
| WO | 01/71016 | 9/2001 |
| WO | 02/09650 | 2/2002 |
| WO | 02/13760 | 2/2002 |
| WO | 02/20003 | 3/2002 |
| WO | 02/28355 | 4/2002 |
| WO | 02/064157 | 8/2002 |
| WO | 02/081007 | 10/2002 |
| WO | 02/097066 | 12/2002 |
| WO | 03/025149 | 3/2003 |
| WO | 03/060077 | 7/2003 |
| WO | 03/103611 | 12/2003 |
| WO | 2004/007697 | 1/2004 |
| WO | 2004/010959 | 2/2004 |
| WO | 2004/019767 | 3/2004 |
| WO | 2005/083061 | 9/2005 |
| WO | 2006/060779 | 6/2006 |
| WO | 2006/093860 | 9/2006 |
| WO | 2007/055905 | 5/2007 |
| WO | 2007/055905 A2 | 5/2007 |
| WO | 2007/076701 | 7/2007 |
| WO | 2011/050266 A1 | 4/2011 |

OTHER PUBLICATIONS

Nakajima M et al. 2009. Coronary flow velocity reserve in patients with ischemic stroke. Medical Science Monitor 15: CD383-388.*

Kawamoto et al., "CD34-Positive Cells Exhibit Increased Potency and Safety for Therapeutic Neovascularization After Myocardial Infarction Compared With Total Mononuclear Cells", Circulation, 2006, vol. 114, pp. 2163-2169.

Kim, Y.-H., "Intramyocardial transplantation of circulating CD34+ cells: source of stem cells for myocardial regeneration", Journal of Korean Medical Science, Dec. 2003, vol. 18, No. 6, pp. 797-803.

Kocher, A. A. et al., "Neovascularization of ischemic myocardium by human bone-marrow-derived angioblasts prevents cardiomyocyte apoptosis, reduces remodeling and improves cardiac function", Nature Medicine, Apr. 2001, vol. 7, No. 4, pp. 430-436.

Koh, J. Y. et al., "Long-term survival of AT-1 cardiomyocyte grafts in syngeneic myocardium", The American Journal of Physiology: Heart and Circulatory Physiology, May 1993, vol. 264, No. 5 (Pt. 2), pp. H1727-H1733.

Korbling, M. et al., "Hepatocytes and epithelial cells of donor origin in recipients of peripheral-blood stem cells", The New England Journal of Medicine, Mar. 7, 2002, vol. 346, No. 10, pp. 738-746.

Krause, D. S. et al., "Multi-organ, multi-lineage engraftment by a single bone marrow-derived stem cell", Cell, May 4, 2001, vol. 105, No. 3, pp. 369-377.

Krause, D. S., "Plasticity of marrow-derived stem cells", Gene Therapy, Jun. 2002, vol. 9, No. 11, pp. 754-758.

Kurrelmeyer, K. M. et al., "Endogenous tumor necrosis factor protects the adult cardiac myocyte against ischemic-induced apoptosis in a murine model of acute myocardial infarction", Proc. Natl. Acad. Sci. U.S.A., May 2000, vol. 97, No. 10, pp. 5456-5461.

Labarge, M. A. et al., "Biological progression from adult bone marrow to mononucleate muscle stem cell to multinucleate muscle fiber in response to injury", Cell, Nov. 15, 2002, vol. 111, No. 4, pp. 589-601.

Lasky, L. A., "Selectins: interpreters of cell-specific carbohydrate information during inflammation", Science, Nov. 1992, vol. 258, No. 5084, pp. 964-969.

Lefer, D. J. et al., "Oxidative stress and cardiac disease", The American Journal of Medicine, Sep. 2000, vol. 109, No. 4, pp. 315-323.

Leone, A. M. et al., "Mobilization of bone marrow-derived stem cells after myocardial infarction and left ventricular function", European Heart Journal, Jun. 2005, vol. 26, No. 12, pp. 1196-1204.

Li, R. K. et al., "Smooth muscle cell transplantation into myocardial scar tissue improves heart function", Journal of Molecular and Cellular Cardiology, Mar. 1999, vol. 31, No. 3, pp. 513-522.

Li, R. K. et al., "Autologous porcine heart cell transplantation improved heart function after a myocardial infarction", The Journal of Thoracic and Cardiovascular Surgery, Jan. 2000, vol. 119, No. 1, pp. 62-68.

Lin, Y. et al., "Origins of circulating endothelial cells and endothelial outgrowth from blood", Journal of Clinical Investigation, Jan. 2000, vol. 105, No. 1, pp. 71-77.

Lonza X-Vivo Media Systems Information Sheet Downloaded from lonza.com.

Ma, X. L. et al., "Monoclonal antibody to L-selectin attenuates neutrophil accumulation and protects ischemic reperfused cat myocardium," Circulation, Aug. 1993, vol. 88, No. 2, pp. 649-658.

Ma, N. et al., "Human cord blood cells induce angiogenesis following myocardial infarction in NOD/scid-mice", Cardiovascular Research, Apr. 1, 2005, vol. 66, No. 1, pp. 45-54.

Mangi, A. A. et al., Mesenchymal stem cells modified with Akt prevent remodeling and restore performance of infarcted hearts, Nature Medicine, Sep. 2003, vol. 9, No. 9, pp. 1195-1201.

Mann, D. L., "Mechanisms and models in heart failure: A combinatorial approach", Circulation, Aug. 31, 1999, vol. 100, No. 9, pp. 999-1008.

Marelli, D. et al., "Cell transplantation for myocardial repair: an experimental approach", Cell Transplantation, 1992, vol. 1, No. 6, pp. 383-390.

Martin-Rendon, E. et al., "Autologous bone marrow stem cells to treat acute myocardial infarction: a systematic review," Eur. Heart J., Aug. 2008, vol. 29, No. 15, pp. 1807-1818.

Miraglia, S. et al., "A novel five-transmembrane hematopoietic stem cell antigen: isolation, characterization, and molecular cloning", Blood, Dec. 15, 1997, vol. 90, No. 12, pp. 5013-5021.

Matsubara, H., "Risk to the coronary arteries of intracoronary stem cell infusion and G-CSF cytokine therapy," The Lancet, Mar. 6, 2004, vol. 363, No. 9411, pp. 746-747.

Muller-Ehmsen, J. et al., "The mobilization of CD34 positive mononuclear cells after myocardial infarction is abolished by revascularization of the culprit vessel", International Journal of Cardiology, Aug. 3, 2005, vol. 103, No. 1, pp. 7-11.

Murry, C. E. et al., "Skeletal myoblast transplantation for repair of myocardial necrosis", The Journal of Clinical Investigation, Dec. 1, 1996, vol. 98, No. 11, pp. 2512-2523.

Okamoto, R. et al., "Damaged epithelia regenerated by bone marrow-derived cells in the human gastrointestinal tract", Nature Medicine, Sep. 2002, vol. 8, No. 9, pp. 1011-1017.

(56) References Cited

OTHER PUBLICATIONS

Orlic, D., "Cytokine mobilized CD34+ cells do not benefit Rhesus monkeys following induced myocardial infarction", Blood suppl., 2002, vol. 100, Abstract #94.
Orlic, D. et al., "Bone marrow cells regenerate infarcted myocardium", Nature, Apr. 5, 2001, vol. 410, No. 6829, pp. 701-705.
Orlic, D. et al., "Mobilized bone marrow cells repair the infarcted heart, improving function and survival", Proc. Natl. Acad. Sci. U.S.A., Aug. 28, 2001, vol. 98, No. 18, pp. 10344-10349.
Ott, I. et al., "Endothelial-like cells expanded from CD34+ blood cells improve left ventricular function after experimental myocardial infarction", The FASEB Journal, Jun. 2005, vol. 19, No. 8, pp. 992-994.
Paul, S. D. et al., "Geriatric patients with acute myocardial infarction: Cardiac risk factor profiles, presentation, thrombolysis, coronary interventions, and prognosis", American Heart Journal, 1996, vol. 131, No. 4, 710-715.
Pecora, A. L. et al., "CD34+CD33- cells influence days to engraftment and transfusion requirements in autologous blood stem-cell recipients", Journal of Clinical Oncology, Jun. 1998, vol. 16, No. 6, pp. 2093-2104.
Pecora, A. L. et al., "A phase II trial evaluating the safety and effectiveness of the AastromReplicell system for augmentation of low-dose blood stem cell transplantation", Bone Marrow Transplantation, Aug. 2001, vol. 28, No. 3, pp. 295-303.
Penn, M. S. et al., "Autologous cell transplantation for the treatment of damaged myocardium", Progress in Cardiovascular Diseases, Jul.-Aug. 2002, vol. 45, No. 1, pp. 21-32.
Pfeffer, M. A. et al. "Ventricular remodeling after myocardial infarction. Experimental observations and clinical implications", Circulation, 1990, vol. 81, No. 4, pp. 1161-1172.
Peichev, M. et al., "Expression of VEGFR-2 and AC133 by circulating human CD34(+) cells identifies a population of functional endothelial precursors", Blood, Feb. 1, 2000, vol. 95, No. 3, pp. 952-958.
Pouzet, B. et al., "Factors affecting functional outcome after autologous skeletal myoblast transplantation", The Annals of Thoracic Surgery, Mar. 2001, vol. 71, No. 3, pp. 844-851.
Rajnoch, C. et al., "Cellular therapy reverses myocardial dysfunction", The Journal of Thoracic Cardiovascular Surgery, May 2001, vol. 121, No. 5, pp. 871-878.
Ren, G. et al., "Morphological Characteristics of the Microvasculature in Healing Myocardial Infarcts", The Journal of Histochemistry and Cytochemistry, 2002, vol. 50, No. 1, pp. 71-79.
Reyes, M. et al., "Origin of endothelial progenitors in human postnatal bone marrow", J. Clinical Investigation, Feb. 2002, vol. 109, No. 3, pp. 337-346.
Rich, M. W. et al., "Is age an independent predictor of early and late mortality in patients with acute myocardial infarction?", The American Journal of Medicine, 1992, vol. 92, No. 1, pp. 7-13.
Robinson, S. W. et al., "Arterial delivery of genetically labelled skeletal myoblasts to the murine heart: long-term survival and phenotypic modification of implanted myoblasts", Cell Transplantation, 1996, vol. 5, No. 1, pp. 77-91.
Ruhparwar, A. et al., "Transplanted fetal cardiomyocytes as cardiac pacemaker", European Journal of Cardio-thoracic Surgery, May 2002, vol. 21, No. 5, pp. 853-857.
Sahoo, S. et al., "Exosomes from human CD34(+) stem cells mediate their proangiogenic paracrine activty," Circ. Res., 2011, vol. 109, No. 7, pp. 724-728.
Saito, T. et al., "Myogenic Expression of Mesenchymal Stem Cells within Myotubes of mdx Mice in Vitro and in Vivo", Tissue Engineering, 1995, vol. 1, No. 4, pp. 327-337.
Sakata, K. et al., "A clinical feature of myocardial stunning associated with acute myocardial infarction", Annals of Nuclear Medicine, 1994, vol. 8, No. 2, pp. 153-157.
Schachinger, V. et al., "Intracoronary bone marrow-derived progenitor cells in acute myocardial infarction," New Engl. J. Med., Sep. 21, 2006, vol. 355, No. 12, pp. 1210-1221.
Schiller, N. B. et al., "Recommendations for quantitation of the left ventricle by two-dimensional echocardiography. American Society of Echocardiography Committee on Standards, Subcommittee on Quantitation of Two-Dimensional Echocardiograms", The Journal of American Society of Echocardiography, Sep.-Oct. 1989, vol. 2, No. 5, pp. 358-367.
Shake, J. G. et al., "Mesenchymal stem cell implantation in a swine myocardial infarct model: engraftment and functional effects", The Annals of Thoracic Surgery, Jun. 2002, vol. 73, No. 6, pp. 1919-1926.
Sheiban, I. ey al., "Time course and determinants of left ventricular function recovery after primary angioplasty in patients with acute myocardial infarction", Journal of the American College of Cardiology, 2001, vol. 38, No. 2, pp. 464-471.
Shi, Q. et al., "Evidence for circulating bone marrow-derived endothelial cells", Blood, Jul. 15, 1998, vol. 92, No. 2, pp. 362-367.
Shintani, S. et al., "Mobilization of endothelial progenitor cells in patients with acute myocardial infarction", Circulation, Jun. 12, 2001, vol. 103, No. 23, pp. 2776-2779.
Simpson, P. J. et al., "Reduction of experimental canine myocardial reperfusion injury by a monoclonal antibody (anti-Mo1, anti-CD11b) that inhibits leukocyte adhesion", Journal of Clinical Investigation, Feb. 1988, vol. 81, No. 2, pp. 624-629.
Soeki, T. et al., "Serial changes in serum VEGF and HGF in patients with acute myocardial infarction", Cardiology, 2000, vol. 93, No. 3, pp. 168-174.
Soonpaa, M. H. et al., "Formation of nascent intercalated disks between grafted fetal cardiomyocytes and host myocardium", Science, Apr. 1, 1994, vol. 264, No. 5155, pp. 98-101.
Sousa, J. E. et al., "New frontiers in cardiology: drug-eluting stents: Part II", Circulation, May 13, 2003, vol. 107, No. 18, pp. 2383-2389.
Stamm, C. et al., "Autologous bone-marrow stem-cell transplantation for myocardial regeneration", The Lancet, Jan. 4, 2003, vol. 361, No. 9351, pp. 45-46.
Stiff, P. et al., "Autologous transplantation of ex vivo expanded bone marrow cells grown from small aliquots after high-dose chemotherapy for breast cancer", Blood, Mar. 15, 2000, vol. 95, No. 6, pp. 2169-2174.
Strauer, B. E. et al., "Repair of infarcted myocardium by autologous intracoronary mononuclear bone marrow cell transplantation in humans", Circulation, Oct. 8, 2002, vol. 106, No. 15, pp. 1913-1918.
Szilvassy et al., "Organ-Selective Homing Defines Engraftment Kinetics of Murine Hematopoietic Stem Cells and Is Compromised by Ex Vivo Expansion", Blood, 1999, vol. 93, pp. 1557-1566.
Takahashi, T. et al., "Ischemia- and cytokine-induced mobilization of bone marrow-derived endothelial progenitor cells for neovascularization", Nature Medicine, Apr. 1999, vol. 5, No. 4, pp. 434-438.
Taylor, D. A. et al., "Regenerating functional myocardium: improved performance after skeletal myoblast transplantation", Nature Medicine, Aug. 1998, vol. 4, No. 8, pp. 929-933.
Thum, T. et al., "Mobilization of bone marrow-derived stem cells after myocardial infarction and left ventricular function: simply effects of optimized drug treatment", European Heart Journal, Aug. 2005, vol. 26, No. 16, pp. 1685.
Toma, C. et al., "Human mesenchymal stem cells differentiate to a cardiomyocyte phenotype in the adult murine heart", Circulation, Jan. 1, 2002, vol. 105, No. 1. pp. 93-98.
Tomita, S. et al., "Autologous transplantation of bone marrow cells improves damaged heart function", Circulation, Nov. 9, 1999, vol. 100 (19 Suppl.), pp. II247-II256.
Tse, H. F. et al., "Angiogenesis in ischaemic myocardium by intramyocardial autologous bone marrow mononuclear cell implantation", The Lancet, Jan. 4, 2003, vol. 361, No. 9351, pp. 47-49.
Vasa, M. et al., "Number and migratory activity of circulating endothelial progenitor cells inversely correlate with risk factors for coronary artery disease", Circulation Research, Jul. 6, 2001, vol. 89, No. 1, pp. E1-E7.
Wakitani, S. et al., "Myogenic cells derived from rat bone marrow mesenchymal stem cells exposed to 5-azacytidine", Muscle & Nerve, Dec. 1995, vol. 18, No. 12, pp. 1417-1426.

(56) References Cited

OTHER PUBLICATIONS

Walter, D. H. et al., "Impaired CXCR4 signaling contributes to the reduced neovascularization capacity of endothelial progenitor cells from patients with coronary artery disease," Circ. Res. Nov. 25, 2005, vol. 97, No. 11, pp. 1142-1151.

Wang, J. S. et al., "The coronary delivery of marrow stromal cells for myocardial regeneration: pathophysiologic and therapeutic implications", The Journal of Thoracic and Cardiovascular Surgery, Oct. 2001, vol. 122, No. 4, pp. 699-705.

Wang, J. et al., "Human CD34+ cells in experimental myocardial infarction: long-term survival, sustained functional improvement, and mechanism of action," Circ. Res., Jun. 25, 2010, vol. 106, No. 12, pp. 1904-1911.

Watanabe, E. et al., "Cardiomyocyte transplantation in a porcine myocardial infarction model", Cell Transplantation, 1998, vol. 7, No. 3, pp. 239-246.

Wollert, K. C. et al., "Intracoronary autologous bone-marrow cell transfer after myocardial infarction: the BOOST randomised controlled clinical trial", The Lancet, Jul. 2004, vol. 364, No. 9429, pp. 141-148.

Yamaguchi, J. et al., "Stromal cell-derived factor-1 effects on ex vivo expanded endothelial progenitor cell recruitment for ischemic neovascularization", Circulation, Mar. 11, 2003, vol. 107, No. 9, pp. 1322-1328.

Yeh, E. T. et al., "Transdifferentiation of human peripheral blood CD34+-enriched cell population into cardiomyocytes, endothelial cells, and smooth muscle cells in vivo", Circulation, Oct. 28, 2003, vol. 108, No. 17, pp. 2070-2073.

Yellon, D. M. et al., "Myocardial reperfusion injury," N. Engl. J. Med., Sep. 13, 2007 vol. 357, No. 11, pp. 1121-1135.

Yin, A. H. et al., "AC133, a novel marker for human hematopoietic stem and progenitor cells", Blood, Dec. 15, 1997, vol. 90, No. 12, pp. 5002-5012.

Yoon, Y. Y S. et al., "Unexpected severe calcification after transplantation of bone marrow cells in acute myocardial infarction", Circulation, Jun. 29, 2004, vol. 109, No. 25, pp. 3154-3157.

Yoshioka, T. et al., "Repair of infarcted myocardium mediated by transplanted bone marrow-derived CD34+ stem cells in a nonhuman primate model", Stem Cells, Mar. 2005, vol. 23, No. 3, pp. 355-364.

Ziegelhoeffer, T. et al., "Bone marrow-derived cells do not incorporate into the adult growing vasculature", Circulation Research, Feb. 6, 2004, vol. 94, No. 2, pp. 230-238.

Aiuti, A. et al., "Human CD34+ cells express CXCR4 and its ligand stromal cell-derived factor-1. Implications for infection by T-cell tropic human immunodeficiency virus," Blood, Jul. 1999, vol. 94, No. 1, pp. 62-73.

Kollet, O. et al., "Human CD34+CXCR4-sorted cells harbor intracellular CSCR4, which can be functionally expressed and provide NOD/SCID repopulation," Blood, Oct. 2002, vol. 100, No. 8, pp. 2778-2786.

Calmels, B, et al., "Preclinical evaluation of an automated closed fluid management device: CytomateTM, for washing out DMSO from hematopeotic stem cell grafts after thawing," Bone Marrow Transplantation, May 2003, vol. 31, No. 9, pp. 823-828.

Wojakowski, W. et al., "Mobilization of bone marrow-derived progenitor cells in acute coronary syndromes," Folia Histochemica Et Cytobiologica, 2005, vol. 43, No. 4, pp. 229-232.

Haider, K. H. et al., "Bone marrow stem cells in the infarcted heart," Coronary Heart disease, 2005, vol. 16, No. 2, pp. 99-103.

Ratajczak, M. Z. et al., "Stem cell plasticity revisited: CXCR4-positive cells expressing mRNA for early muscle, liver and neural cells 'hide out' in the bone marrow," Leukemia, Oct. 2003, vol. 18, pp. 29-40.

Kucia, M. et al., "Cells Expressing Early Cardiac Markers Reside in the Bone Marrow and Are Mobilized Into the Peripheral Blood After Myocardial Infarction," Circulation Research, 2004, vol. 95, pp. 1191-1199.

Antman et al., Heart Disease, 6th ed., E. Brunwald, Zipes D.P., Libby P. (eds.), Philadelphia, Saunders, 2001, pp. 1386-1399.

Asahara, T. et al., "VEGF contributes to postnatal neovascularization by mobilizing bone marrow-derived endothelial progenitor cells", The EMBO Journal, Jul. 15, 1999, vol. 18, No. 14, pp. 3964-3972.

Asahara, T. et al., "Isolation of putative progenitor endothelial cells for angiogenesis", Science, Feb. 14, 1997, vol. 275, No. 5302, pp. 964-967.

Askari, A. T. et al., "Effect of stromal-cell-derived factor 1 on stem-cell homing and tissue regeneration in ischaemic cardiomyopathy", The Lancet, Aug. 30, 2003, vol. 362, No. 9385, pp. 697-703.

Assmus, B. et al., "Transplantation of Progenitor Cells and Regeneration Enhancement in Acute Myocardial Infarction (TOPCARE-AMI)", Circulation, Dec. 10, 2002, vol. 106, No. 24, pp. 3009-3017.

Atkins, B. Z. et al., "Cellular cardiomyoplasty improves diastolic properties of injured heart", The Journal of Surgical Research, Aug. 1999, vol. 85, No. 2, pp. 234-242.

Atkins, B. Z. et al., "Myogenic cell transplantation improves in vivo regional performance in infarcted rabbit myocardium", The Journal of Heart and Lung Transplantation, Dec. 1999, vol. 18, No. 12, pp. 1173-1180.

Balsam, L. B. et al., "Haematopoietic stem cells adopt mature haematopoietic fates in ischaemic myocardium", Nature, Apr. 8, 2004, vol. 428, No. 6983, pp. 668-673.

Birdsall et al., "Complement C5a, TGF-beta 1, and MCP-1, in sequence, induce migration of monocytes into ischemic canine myocardium within the first one to five hours after reperfusion," Circulation, Feb. 4, 1997, vol. 95, No. 3, pp. 684-692.

Bolli, R., et al., "Basic and clinical aspects of myocardial stunning", Progress in Cardiovascular Diseases, 1998, vol. 40, No. 6, pp. 477-516.

Bolognese, L. et al., "Left ventricular remodeling after primary coronary angioplasty: patterns of left ventricular dilation and long-term prognostic implications", Circulation, Oct. 29, 2002, vol. 106, No. 18, pp. 2351-2357.

Braunwald, E. et al., "Congestive Heart Failure: Fifty Years of Progress", Circulation, 2000, vol. 102, pp. IV-14-IV-23.

Britten, M. B. et al., "Infarct remodeling after intracoronary progenitor cell treatment in patients with acute myocardial infarction (TOPCARE-AMI): mechanistic insights from serial contrast-enhanced magnetic resonance imaging", Circulation, Nov. 4, 2003, vol. 108, No. 18, pp. 2212-2218.

Camargo, F. D. et al., "Single hematopoietic stem cells generate skeletal muscle through myeloid intermediates", Nature Medicine, Dec. 2003, vol. 9, No. 12, pp. 1520-1527.

Ceradini, D. J. et al., "Progenitor cell trafficking is regulated by hypoxic gradients through HIF-1 induction of SDF-1", Nature Medicine, Aug. 2004, vol. 10, No. 8, pp. 858-864.

Cerqueira, M. D. et al., "Safety profile of adenosine stress perfusion imaging: results from the Adenoscan Multicenter Trial Registry", Journal of the American College of Cardiology, Feb. 1994, vol. 23, No. 2, pp. 384-389.

Chen, HK, et al., "Combined cord blood stem cells and gene therapy enhances angiogenesis and improves cardiac performance in mouse after acute myocardial infarction", Eur. J. Clin. Invest., Nov. 2005, vol. 35, No. 11, pp. 677-686.

Chiu, R. C. et al., "Cellular cardiomyoplasty: myocardial regeneration with satellite cell implantation", The Annals of Thoracic Surgery, Jul. 1995, vol. 60, No. 1, pp. 12-18.

Dobert, N. et al., "Transplantation of progenitor cells after reperfused acute myocardial infarction: evaluation of perfusion and myocardial viability with FDG-PET and thallium SPECT", European Journal of Nuclear Medicine and Molecular Imaging, 2004, vol. 31, No. 8, pp. 1146-1151.

Dorfman, J. et al., "Myocardial tissue engineering with autologous myoblast implantation", The Journal of Thoracic and Cardiovascular Surgery, Nov. 1998, vol. 116, No. 5, pp. 744-751.

Edelberg, J. M. et al., "Young adult bone marrow-derived endothelial precursor cells restore aging-impaired cardiac angiogenic function", Circulation Research, May 31, 2002, vol. 90, No. 10, pp. E89-E93.

(56) References Cited

OTHER PUBLICATIONS

Ejiri, M. et al., "Development of collateral circulation after acute myocardial infarction; its role in preserving left ventricular function", Journal of Cardiology, 1990, vol. 20, pp. 31-37.

Entman, M. L. et al., "Neutrophil induced oxidative injury of cardiac myocytes. A compartmented system requiring CD11b/CD18-ICAM-1 adherence", Journal of Clinical Investigation, Oct. 1992, vol. 90, No. 4, pp. 1335-1345.

Etzion, S. et al., "Influence of embryonic cardiomyocyte transplantation on the progression of heart failure in a rat model of extensive myocardial infarction", Journal of Molecular and Cellular Cardiology, Jul. 2001, vol. 33, No. 7, pp. 1321-1330.

Fang, K. C. et al., "Mast cell expression of gelatinases A and B is regulated by kit ligand and TGF-beta", The Journal of Immunology, 1999, vol. 162, pp. 5528-5535.

Frangogiannis, N. G. et al., "Stem cell factor induction is associated with mast cell accumulation after canine myocardial ischemia and reperfusion", Circulation, Aug. 1998, vol. 98, No. 7, pp. 687-698.

Frangogiannis, N. G. et al., "The inflammatory response in myocardial infarction", Cardiovascular Research, 2002, vol. 53, No. 1, pp. 31-47.

Frangogiannis, N. G. et al., "Resident cardiac mast cells degranulate and release preformed TNF-alpha, initiating the cytokine cascade in experimental canine myocardial ischemia/reperfusion", Circulation, Aug. 1998, vol. 98, No. 7, pp. 699-710.

Frangogiannis, N. G. et al., "Induction and suppression of interferon-inducible protein (IP)-10 in reperfused myocardial infarcts may regulate angiogenesis", The FASEB Journal, Jun. 2001, vol. 15, No. 8, pp. 1428-1430.

Frangogiannis, N. G. et al., "IL-10 is induced in the reperfused myocardium and may modulate the reaction to injury", The Journal of Immunology, Sep. 1, 2000, vol. 165, No. 5, pp. 2798-2808.

Hamano, K. et al., "Therapeutic angiogenesis induced by local autologous bone marrow cell implantation", The Annals of Thoracic Surgery, Apr. 2002, vol. 73, No. pp. 1210-1215.

Hamano, K. et al., "Local implantation of autologous bone marrow cells for therapeutic angiogenesis in patients with ischemic heart disease: clinical trial and preliminary results", Japanese Circulation Journal, Sep. 2001, vol. 65, No. 9, pp. 845-847.

Hattori, K. et al., "Placental growth factor reconstitutes hematopoiesis by recruiting VEGFR1(+) stem cells from bone-marrow microenvironment", Nature Medicine, Aug. 2002, vol. 8, No. 8, pp. 841-849.

Hayashi, M. et al., "Comparison of intramyocardial and intravenous routes of delivering bone marrow cells for the treatment of ischemic heart disease: an experimental study", Cell Transplantation, 2004, vol. 13, No. 6, pp. 639-647.

Heeschen, C. et al., "Profoundly reduced neovascularization capacity of bone marrow mononuclear cells derived from patients with chronic ischemic heart disease," Circulation, Apr. 6 2004, vol. 109, No. 13, pp. 1615-1622.

Hertenstein et al., Monitoring of bone marrow cell homing in the infarcted human myocardium by PET. Blood supplement, 2004; Abst. No. 2696.

Hill, J. M. et al., "Circulating endothelial progenitor cells, vascular function, and cardiovascular risk", New England Journal of Medicine, Feb. 13, 2003, vol. 348, No. 7, pp. 593-600.

Hirai, T. et al., "Importance of collateral circulation for prevention of left ventricular aneurysm formation in acute myocardial infarction", Circulation, 1989, vol. 79, No. 4, pp. 791-796.

Hirata, Y. et al., "Human umbilical cord blood cells improve cardiac function after myocardial infarction", Biochemical and Biophysical Research Communications, Feb. 11, 2005, vol. 327, No. 2, pp. 609-614.

Hofmann, M. et al., "Monitoring of Bone Marrow Cell Homing Into the Infarcted Human Myocardium", Circulation, 2005, vol. 111, pp. 2198-2202.

Ince, H. et al., "Prevention of Left Ventricular Remodeling With Granulocyte Colony-Stimulating Factor After Acute Myocardial Infarction: Final 1-year Results of the Front-Integrated Revascularization and Stem Cell Liberation in Evolving Acute Myocardial Infarction by Granulocyte Colony-Stimulating Factor (FIRSTLINE-AMI) Trial", Circulation, Aug. 30, 2005, vol. 112 (9 Suppl.), pp. I-73-I-80.

International Search Report and Written Opinion for PCT/US06/41536.

Jackson, K. A. et al., "Regeneration of ischemic cardiac muscle and vascular endothelium by adult stem cells", The Journal of Clinical Investigation, 2001, vol. 107, No. 11, pp. 1395-1402.

Jain, M. et al., "Cell therapy attenuates deleterious ventricular remodeling and improves cardiac performance after myocardial infarction", Circulation, Apr. 10, 2001, vol. 103, No. 14, pp. 1920-1927.

Jiang, Y. et al., "Multipotent progenitor cells can be isolated from postnatal murine bone marrow, muscle, and brain", Experimental Hematology, Aug. 2002, vol. 30, No. 8, pp. 896-904.

Jiang Y. et al., "Pluripotency of mesenchymal stem cells derived from adult marrow," Nature, Jul. 4, 2002, vol. 418, No. 6893, pp. 41-49.

Jo, D.-Y. et al., "Chemotaxis of primitive hematopoietic cells in response to stromal cell—derived factor-1", Journal of Clinical Investigation, Jan. 2000, vol. 105, No. 1, pp. 101-111.

Kamihata, H. et al., "Implantation of bone marrow mononuclear cells into ischemic myocardium enhances collateral perfusion and regional function via side supply of angioblasts, angiogenic ligands, and cytokines", Circulation, Aug. 28, 2001, vol. 104, No. 9, pp. 1046-1052.

Kang, H. -J. et al., "Effects of intracoronary infusion of peripheral blood stem-cells mobilised with granulocyte-colony stimulating factor on left ventricular systolic function and restenosis after coronary stenting in myocardial infarction: the MAGIC cell randomised clinical trial", The Lancet, Mar. 6, 2004, vol. 363, pp. 751-756; 1732-1738.

Kawamoto, A. et al., "Therapeutic potential of ex vivo expanded endothelial progenitor cells for myocardial ischemia", Circulation, Feb. 6, 2001, vol. 103, No. 5, pp. 634-637.

Pecora, A. L. et al., Bone marrow derived CD34(+) CXCR4(+) cells maintain viability, motility and sterility up to 72 hours and are compatible with balloon dilatation catheters used for intra coronary artery infusion; Pre-clinical development of a pharmaceutical grade cell therapy for acute myocardial infarction (AMR-001), Blood, 2007, vol. 110, No. 11, p. 368, Abstract 1214.

Waller, N. et al., "CD34+ CXCR4+ cell therapy (AMR-001) for myocardial infarction: Preliminary processing and product results of a phase I dose escalation study," Blood, 2007, vol. 110, No. 11, p. 238, Abstract No. 773.

Waller, et al. 2007 "CD34+CXCR4+ Cell Therapy (AMR-0001) for Myocardial Infarction: Preliminary Processing and Product Results of a Phase I Dose Escalation Study".

Wojakowski et al. 2006, "Abstract 3162: Mobilization of CXCR4+ Stem Cells in Acute Myocardial Infarction Is correlated With Left Ventricular Ejection Fraction and Myocardial Perfusion Assessed by MRI in 3 Year Follow-Up (Regent Trial)".

Yeh et al. 2006, "A novel approach to studying transformation of human stem cells into cardiac cells in in vivo.".

Gottlieb RA et al. 1994. Reperfusion injury induces apoptosis in rabbit cardiomyocytes. J Clin Invest 94: 1621-1628.

Toldo S et al. 2011. The role of PDI as a survival factor in cardiomyocyte ischemia. Meth Enzymol 489: 48-47-66; pp. 47 and 48.

Liu, X, et al., "Neuregulin-1/erbB-Activation improves cardiac function and survival in models of ischemic, dilated, and viral cardiomyopathy", Journal of the American College of Cardiology, 2006, vol. 48, pp. 1-10, Elsevier, Inc.

\* cited by examiner

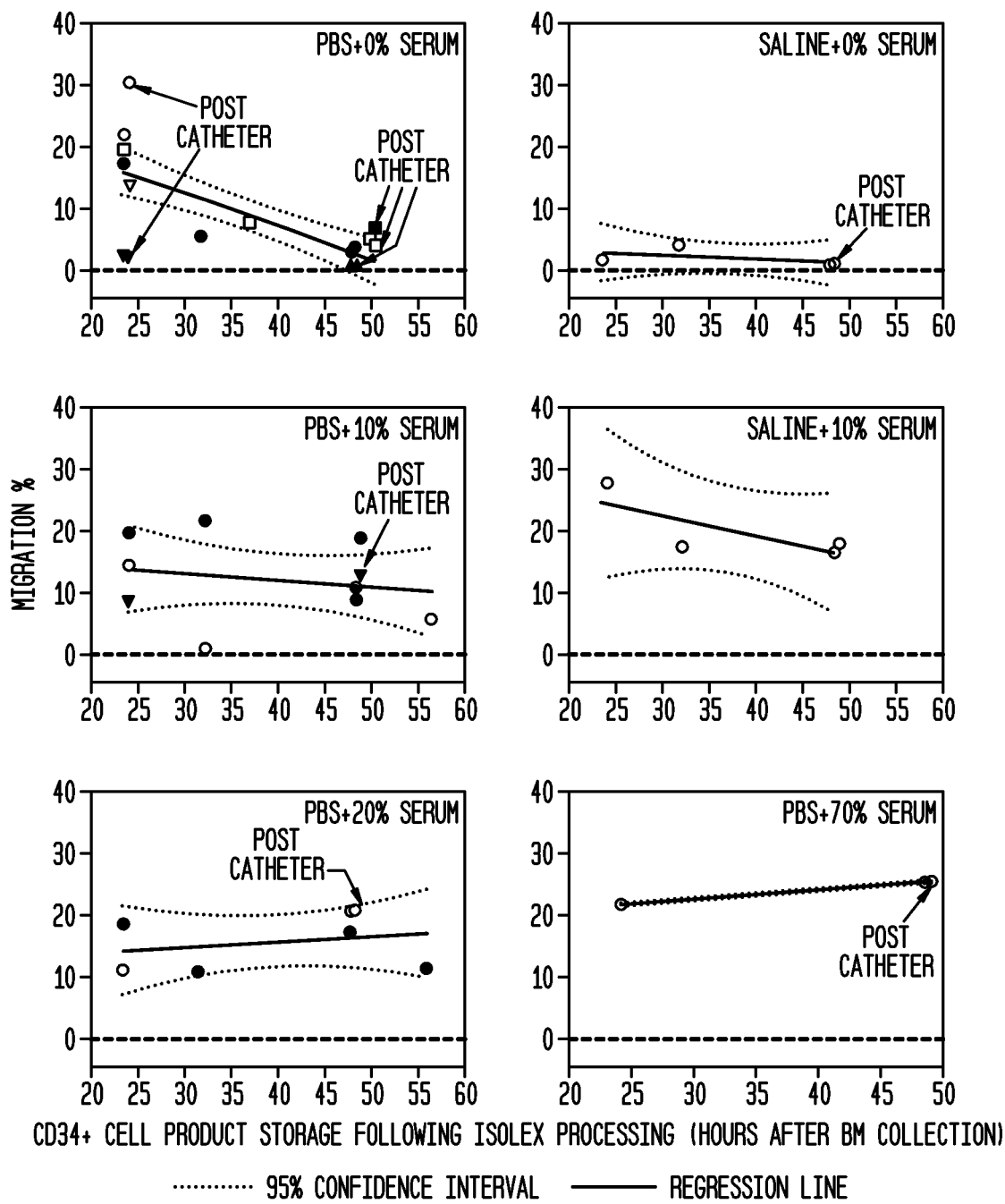

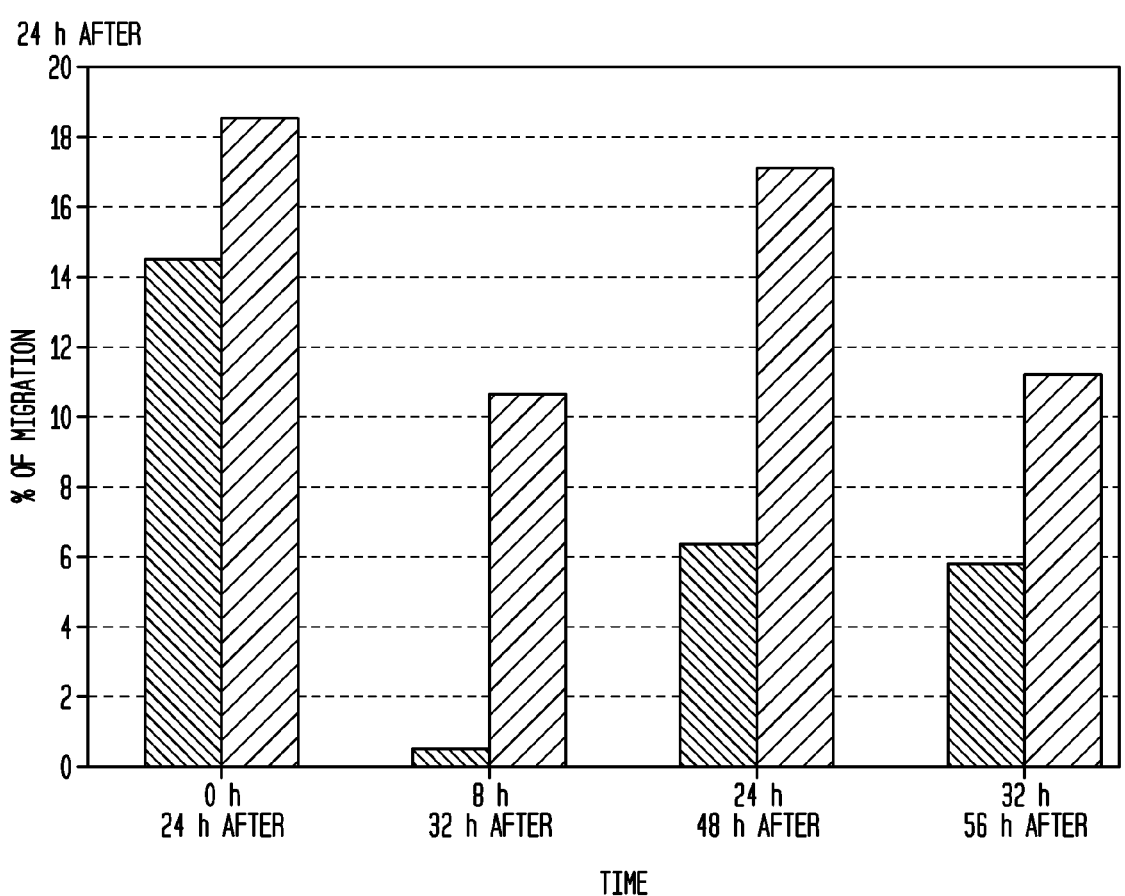

COMPOSITIONS AND METHODS FOR TREATING PROGRESSIVE MYOCARDIAL INJURY DUE TO A VASCULAR INSUFFICIENCY

CROSS REFERENCE TO RELATED APPLICATIONS

This application is a continuation of U.S. application Ser. No. 12/910,328 (filed Oct. 22, 2010) now abandoned, which claims the benefit of priority to U.S. Provisional Application No. 61/254,539 (filed Oct. 23, 2009) and is a continuation-in-part of U.S. application Ser. No. 12/629,361 (filed Dec. 2, 2009), which claims the benefit of priority to U.S. Provisional Application No. 61/119,552 (filed Dec. 3, 2008) and U.S. 61/169,850 (filed Apr. 16, 2009) and a continuation-in-part of U.S. Ser. No. 11/552,396 (filed Oct. 24, 2006), which issued as U.S. Pat. No. 7,794,705, which claims the benefit of priority to U.S. Provisional Application No. 60/734,151 (filed Nov. 7, 2005). U.S. application Ser. No. 12/910,328 is also a continuation-in-part of U.S. application Ser. No. 12/401,291 (filed Mar. 10, 2009), which issued as U.S. Pat. No. 8,088,370, which is a division of U.S. application Ser. No. 11/552,396 filed Oct. 24, 2006, which issued as U.S. Pat. No. 7,794,705. Each of these applications is incorporated herein by reference in its entirety.

FIELD OF THE INVENTION

The described invention relates to compositions comprising a chemotactic hematopoietic stem cell product and methods of use thereof for treating early or late adverse consequences of vascular insufficiency.

BACKGROUND OF THE INVENTION

The Cardiac Cycle

The term "cardiac cycle" is used to refer to all or any of the mechanical events related to the coronary blood flow or blood pressure that occurs from the beginning of one heartbeat to the beginning of the next. Blood pressure increases and decreases throughout the cardiac cycle. The frequency of the cardiac cycle is the heart rate. Every single 'beat' of the heart involves five major stages: (1) "late diastole," which is when the semilunar valves close, the atrioventricular (Av) valves open and the whole heart is relaxed; (2) "atrial systole," which is when the myocardium of the left and right atria are contracting, AV valves open and blood flows from atrium to ventricle; (3) "isovolumic ventricular contraction," which is when the ventricles begin to contract, AV and semilunar valves close, and there is no change in volume; (4) "ventricular ejection," which is when the ventricles are empty but still contracting and the semilunar valves are open; and (5) "isovolumic ventricular relaxation," when pressure decreases, no blood is entering the ventricles, the ventricles stop contracting and begin to relax, and the semilunar valves are shut because blood in the aorta is pushing them shut. The cardiac cycle is coordinated by a series of electrical impulses that are produced by specialized heart cells found within the sino-atrial node and the atrio-ventricular node.

Coronary Blood Flow

The flow of blood through the coronary arteries is pulsatile, with characteristic phasic systolic and diastolic flow components. Systolic flow, which relates to the contraction or pumping phase of the heart cycle, has rapid, brief, retrograde responses. Diastolic flow, which relates to the relaxation or filling phase of the heart cycle, occurs during the relaxation phase after myocardial contraction, with an abrupt increase above systolic levels and a gradual decline parallel with that of aortic diastolic pressures. Intramural coronary blood volume changes during each heartbeat, with the myocardium accommodating the volume change brought about by muscular contraction. Coronary venous flow is out of phase with coronary arterial flow, occurring predominantly in systole and nearly absent during diastole.

For each heartbeat, blood pressure varies between systolic and diastolic pressures. The term "systolic pressure" refers to the peak pressure in the arteries, which occurs near the end of the cardiac cycle when the ventricles are contracting. The term "diastolic pressure" refers to the minimum pressure in the arteries, which occurs near the beginning of the cardiac cycle when the ventricles are filled with blood.

Coronary blood flow not only is phasic but also varies with the type of vessel and location in the myocardium. Coronary arterioles appear to have specialized regulatory elements along their length that operate "in series" in an integrated manner. A system of multiple functional "valves" permits fine control of the coronary circulation. The smallest arterioles dilate during metabolic stress, resulting in reduced microvascular resistance and increased myocardial perfusion. Stenosis or narrowing of a blood vessel produces resistance to blood flow related directly to the morphologic features of the stenosis. As the upstream arteriolar pressure decreases due to a fall in distending pressure across the stenosis, myogenic dilation of slightly larger arterioles upstream occurs and causes an additional decrease in resistance. Increased flow in the largest arterioles augments shear stress and triggers flow-mediated dilation, further reducing the resistance of this network.

The arterial and venous pulsatile flow characteristics of the heart are dependent on intramyocardial compliance. The term "compliance" refers to a measure of the tendency of a hollow organ to resist recoil toward its original dimensions upon removal of a distending or compressing force. The higher the compliance the more elastic the material. Compliance is calculated using the following equation, where $\Delta V$ is the change in volume, and $\Delta P$ is the change in pressure:

$$C = \Delta V / \Delta P$$

The capacity of the heart as a reservoir is controlled by resistance arterioles to coronary vascular inflow. Outlet resistance is related to intramural cardiac veins. The intramyocardial capillary resistance influences both arterial and venous responses but predominantly acts in concert with outlet resistance.

Approximately 75% of total coronary resistance occurs in the arterial system, which comprises conductance (R1), prearteriolar (R2) and arteriolar and intramyocardial capillary vessels (R3). Normal epicardial coronary arteries in humans typically are 0.3 to 5 mm in diameter, and do not offer appreciable resistance to blood flow. Normally, large epicardial vessel resistance (R1) is trivial until atherosclerotic obstructions compromise the lumen. Precapillary arterioles (R2), 100 to 500 µm in size) are resistive vessels connecting epicardial to myocardial capillaries and are the principal controllers of coronary blood flow. They contribute approximately 25% to 35% of total coronary resistance. Distal precapillary arteriolar vessels (<100 µm in diameter), the main site of metabolic regulation of coronary blood flow, are responsible for 40-50% of coronary flow resistance. The dense network of about 4000 capillaries per square millimeter ensures that each myocyte is adjacent to a capillary. Capillaries are not uniformly patent (meaning open; affording free passage), because precapillary sphincters regulate flow according to the needs of the myocardium.

Several conditions, such as left ventricular hypertrophy, myocardial ischemia, or diabetes, can impair the microcirculatory resistance (R3), blunting the maximal absolute increase in coronary flow in times of increased oxygen demand.

Ischemia

The myocardium depends almost entirely on aerobic metabolism, since oxygen stores in the heart are meager. Myocardial oxygen supply rises and falls in response to the oxygen (energy) demands of the myocardium. The term "autoregulation" refers to the ability to maintain myocardial perfusion at constant levels in the face of changing driving forces. Autoregulation maintains coronary perfusion at relatively constant levels over a wide range of mean aortic pressure. When aortic pressure exceeds its upper or lower limits, coronary blood flow precipitously declines or increases proportionately.

The heart needs to be supplied with a sufficient quantity of oxygen to prevent underperfusion. When reduced perfusion pressure distal to stenoses is not compensated by autoregulatory dilation of the resistance vessels, ischemia, meaning a lack of blood supply and oxygen, occurs. Because the zone least supplied generally is the farthest out, ischemia generally appears in areas farthest away from the blood supply.

After total or near-total occlusion of a coronary artery, myocardial perfusion occurs by way of collaterals, meaning vascular channels that interconnect epicardial arteries. Collateral channels may form acutely or may preexist in an under-developed state before the appearance of coronary artery disease. Preexisting collaterals are thin-walled structures ranging in diameter from 20 µm to 200 µm, with a variable density among different species. Preexisting collaterals normally are closed and nonfunctional, because no pressure gradient exists to drive flow between the arteries they connect. After coronary occlusion, the distal pressure drops precipitously and preexisting collaterals open virtually instantly.

The term "myocardial ischemia" refers to a decrease in blood supply and oxygen to the cells of the myocardium. The development of myocardial ischemia has been attributed to two mechanisms: (1) increased myocardial oxygen demand, and (2) decreased myocardial perfusion and oxygen delivery. (Willerson, J. T. et al., J. Am. Coll. Cardiol. 8(1): 245-50 (1986)). Myocardial ischemia generally appears first and is more extensive in the subendocardial region, since these deeper myocardial layers are farthest from the blood supply, with greater need for oxygen.

Transient ischemia, hibernating myocardium, and myocardial infarction are clinically different conditions.

Transient Ischemia.

The term "transient ischemia" as used herein refers to a reversible (meaning that the myocytes survive the insult) narrowing of a coronary artery at rest or with exercise where there is no thrombus or plaque rupture but where blood supply cannot be met. Every time the heart's oxygen demand increases, an imbalance between oxygen demand and supply is created. Transient ischemia produces a cascade of events beginning with metabolic and biochemical alterations leading to impaired ventricular relaxation and diastolic dysfunction, impaired systolic function, and electrocardiographic abnormalities with ST segment alterations, followed by increased end-diastolic pressure with left ventricular dyssynchrony, hypokineses, akinesis, and dyskinesis, and lastly painful symptoms of angina. Even though ischemic myocytes experience physiological and metabolic changes within seconds of the cessation of coronary flow, resulting in T wave and sometimes ST segment abnormalities (but without serum enzyme elevation), no cell death results from the ischemia. Kloner, R. A. and Jennings, R B, Circulation 104: 2981-89 (2001). Once blood flow is re-established, a complete recovery of myocyte contractile function takes place.

Although angina pectoris (chest pain) may be a symptom of transient ischemia, by and large transient ischemia is silent (meaning ST-segment depression of at least 1 mm is present without associated symptoms, e.g., chest pain) in 79% of subjects. In most patients with stable angina, for example, physical effort or emotion, with a resultant increase in heart rate, blood pressure, or contractile state, or any combination thereof, increases myocardial oxygen demand without an adequate delivery in oxygen delivery through tightly narrowed (stenosed) coronary arteries. More than 40% of patients with stable angina treated with one or more antianginal drugs have frequent episodes of silent ischemia, which has been shown to predict a higher risk of coronary events and cardiac death. Deedwania, P C, Carbajal, E V, Arch. Intern. Med. 150: 2373-2382 (1991).

Chronic Myocardial Ischemia.

The term "chronic myocardial ischemia (CMI)" as used herein refers to a prolonged subacute or chronic state of myocardial ischemia due to narrowing of a coronary blood vessel in which the myocardium "hibernates", meaning that the myocardium downregulates or reduces its contractility, and hence its myocardial oxygen demand, to match reduced perfusion, thereby preserving cellular viability and preventing myocardial necrosis. This hibernating myocardium is capable of returning to normal or near-normal function on restoration of an adequate blood supply. Once coronary blood flow has been restored to normal or near normal and ischemia is resolved, however, the hibernating myocardium still does not contract. This flow-function mismatch resulting in a slow return of cardiac function after resolution of ischemia has been called stunning. The length of time for function to return is quite variable, ranging from days to months, and is dependent on a number of parameters, including the duration of the original ischemic insult, the severity of ischemia during the original insult, and the adequacy of the return of the arterial flow. A number of studies have provided evidence for inflammation in hibernating myocardium. Heusch, G. et al., Am. J. Physiol. Heart Circ. Physiol. 288: 984-99 (2005). A study conducted in a porcine model of myocardial hibernation in which the mean rest (left anterior descending coronary artery (LAD) coronary blood flow was reduced to about 60% of baseline for a period of 24 hours to four weeks, detected apoptotic myocytes in all experimental pigs in the hibernating regions supplied by the stenotic LAD, suggesting that functional downregulation may not be adequate to prevent gradual, ongoing myocyte death through apoptosis in hibernating myocardium. Chen, C, et al., J. Am. Coll. Cardiol. 30: 1407-12 (1997).

Acute Myocardial Infarction (AMI).

Another type of insult occurs during AMI. AMI is an abrupt change in the lumen of a coronary blood vessel which results in ischemic infarction, meaning that it continues until heart muscle dies. On gross inspection, myocardial infarction can be divided into two major types: transmural infarcts, in which the myocardial necrosis involves the full or nearly full thickness of the ventricular wall, and subendocardial (nontransmural) infarcts, in which the myocardial necrosis involves the subendocardium, the intramural myocardium, or both, without extending all the way through the ventricular wall to the epicardium. There often is total occlusion of the vessel with ST segment elevation because of thrombus formation within the lumen as a result of plaque rupture. The prolonged ischemic insult results in apoptotic and necrotic cardiomyocyte cell death. See Kajstura, J., et al., Lab Invest. 74: 86-107 (1996). Necrosis compromises the integrity of the sarcolemmal membrane and intracellular macromolecules such that serum cardiac markers, such as cardiac-specific troponins and enzymes, such as serum creatine kinase (CK), are released. In addition, the patient may have electrocardiogram (ECG) changes because of full thickness damage to the muscle. An ST-Elevation Myocardial Infarction (STEMI) is a larger injury than a non-ST-elevation myocardial infarction. ST-segment elevation and Q waves on the ECG, two features highly indicative of myocardial infarction, are seen in only about half of myocardial infarction cases on presentation.

AMI remains common with a reported annual incidence of 1.1 million cases in the United States alone (Antman, E. M., Braunwald, E., Acute Myocardial Infarction, in Principles of Internal Medicine, 15th Ed., Braunwald, E. et al., Eds., New York: McGraw-Hill (2001)). Preclinical and clinical data demonstrate that following a myocardial infarction, the acute loss of myocardial muscle cells and the accompanying peri-infarct border zone hypo-perfusion result in a cascade of events causing an immediate diminution of cardiac function, with the potential for long term persistence. The extent of myocardial cell loss is dependent on the duration of coronary artery occlusion, existing collateral coronary circulation and the condition of the cardiac microvasculature. Paul et al., Am. Heart J. 131: 710-15 (1996); Pfeffer, M. A., Braunwald, E., Circulation 81: 1161-72 (1990); Sheilban, I. e. al., J. Am. Coll. Cardiol. 38: 464-71 (2001); Braunwald E., Bristow, M. R., Circulation 102: IV-14-23 (2000); Rich et al., Am. J. Med. 92:7-13 (1992); Ren et al., J. Histochem. Cytochem. 49: 71-79 (2002); Hirai, T. et al., Circulation 79: 791-96 (1989); Ejiri, M. et al., J. Cardiology 20: 31-37 (1990). Because myocardial cells have virtually no ability to regenerate, myocardial infarction leads to permanent cardiac dysfunction due to contractile-muscle cell loss and replacement with nonfunctioning fibrotic scarring. Frangogiannis, N. G., et al., Cardiovascular Res. 53(1): 31-47 (2002). Moreover, compensatory hypertrophy of viable cardiac muscle leads to microvascular insufficiency that results in further demise in cardiac function by causing myocardial muscle hibernation and apoptosis of hypertrophied myocytes in the peri-infarct border zone.

Among survivors of myocardial infarction, residual cardiac function is influenced by the extent of ventricular remodeling (meaning changes in size, shape, and function, typically a progressive decline in function, of the heart after injury). Alterations in ventricular topography (meaning the shape, configuration, or morphology of a ventricle) occur in both infarcted and healthy cardiac tissue after myocardial infarction. Pfeffer, M. A., Braunwald, E., Circulation 81: 1161-72 (1990). Ventricular dilatation (meaning a stretching, enlarging or spreading out of the ventricle) causes a decrease in global cardiac function and is affected by the infarct size, infarct healing and ventricular wall stresses. Recent efforts to minimize remodeling have been successful by limiting infarct size through rapid reperfusion (meaning restoration of blood flow) using thrombolytic agents, and mechanical interventions, including, but not limited to, placement of a stent, along with reducing ventricular wall stresses by judicious use of pre-load therapies and proper after-load management. Id. Regardless of these interventions, a substantial percentage of patients experience clinically relevant and long-term cardiac dysfunction after myocardial infarction. Sheiban, I. et al., J. Am. Coll. Cardiol. 38: 464-71 (2001). Despite revascularization of the infarct related artery circulation and appropriate medical management to minimize ventricular wall stresses, a significant percentage of these patients experience ventricular remodeling, permanent cardiac dysfunction, and consequently remain at an increased lifetime risk of experiencing adverse cardiac events, including death. Paul et al., Am. Heart J. 131: 710-15 (1996); Pfeffer, M. A., Braunwald, E., Circulation 81: 1161-72 (1990).

At the cellular level, immediately following a myocardial infarction, transient generalized cardiac dysfunction uniformly occurs. In the setting of a brief (i.e., lasting three minutes to five minutes) coronary artery occlusion, energy metabolism is impaired, leading to demonstrable cardiac muscle dysfunction that can persist for up to 48 hours despite immediate reperfusion. This so-called "stunned myocardium phenomenon" occurs subsequent to or after reperfusion and is thought to be a result of reactive oxygen species. The process is transient and is not associated with an inflammatory response. Frangogiannis, N. G., et al., Cardiovascular Res. 53(1): 31-47 (2002). After successful revascularization, significant recovery from stunning occurs within three to four days, although complete recovery may take much longer. Boli, R., Prog. Cardiovascular Disease 40(6): 477-515 (1998); Sakata, K. et al., Ann. Nucleic Med. 8: 153-57 (1994); Wollert, K. C. et al., Lancet 364: 141-48 (2004).

Coronary artery occlusion of more significant duration, i.e., lasting more than five minutes, leads to myocardial ischemia (i.e. an insufficient blood flow to the heart's muscle mass) and is associated with a significant inflammatory response that begins immediately after reperfusion and can last for up to several weeks. Frangogiannis, N. G., et al., Cardiovascular Res. 53(1): 31-47 (2002); Frangogiannis, N. G. et al., Circulation 98: 687-798 (1998).

The inflammatory process following reperfusion is complex. Initially it contributes to myocardial damage but later leads to healing and scar formation. This complex process appears to occur in two phases. In the first so-called "hot" phase (within the first five days), reactive oxygen species (in the ischemic myocardial tissue) and complement activation generate a signal chemotactic for leukocytes (chemotaxis is the directed motion of a motile cell, organism or part towards environmental conditions it deems attractive and/or away from surroundings it finds repellent) and initiate a cytokine cascade. Lefer, D. J., Granger, D. N., Am. J. Med. 4:315-23 (2000); Frangogiannis, N. G., et al., Circulation 7:699-710 (1998). Mast cell degranulation, tumor necrosis factor alpha (TNFα) release, and increased interleukin-6 (IL-6), intercellular adhesion molecule 1 ("ICAM-1" or CD-54, a receptor typically expressed on endothelial cells and cells of the immune system), selectin (L, E and P) and integrin (CD11a, CD11b and CD18) expression all appear to contribute to neutrophil accumulation and degranulation in ischemic myocardium. Frangogiannis, N. G. et al., Circulation 7: 699-710 (1998), Kurrelmeyer, K. M, et al., Proc. Natl. Acad. Sci. USA. 10: 5456-61 (2000); Lasky, L. A., Science 258: 964-69 (1992); Ma, X. L., et al., Circulation 88(2): 649-58 (1993); Simpson, P. J. et al., J. Clin. Invest. 2: 624-29 (1998). Neutrophils contribute significantly to myocardial cell damage and death through microvascular obstruction and activation of neutrophil respiratory burst pathways after ligand-specific adhesion to cardiac myocytes.

Entman, M. L., et al., J. Clin. Invest. 4: 1335-45 (1992). During the "hot" phase, angiogenesis is inhibited due to the release of angiostatic substances, including interferon gamma-inducible protein (IP 10). Frangogiannis, N. G., et al., FASEB J. 15: 1428-30 (2001).

In the second phase, the cardiac repair process begins (about day 6 to about day 14), which eventually leads to scar formation (about day 14 to about day 21) and subsequent ventricular remodeling (about day 21 to about day 90). Soon after reperfusion, monocytes infiltrate the infarcted myocardium. Attracted by complement (C5a), transforming growth factor B1 ("TGF-B1") and monocyte chemotactic protein 1 ("MCP-1"), monocytes differentiate into macrophages that initiate the healing process by scavenging dead tissue, regulating extracellular matrix metabolism, and inducing fibroblast proliferation. Birdshall, H. H., et al., Circulation 3: 684-92 (1997). Secretion of interleukin 10 (IL-10) by infiltrating lymphocytes also promotes healing by down-regulating inflammatory cytokines and influencing tissue remodeling. Frangogiannis, N. G. et al., J. Immunol. 5:2798-2808 (2000). Mast cells also appear to be involved in the later stages of myocardial repair by participating in the formation of fibrotic scar tissue. Stem Cell Factor (SCF) is a potent attractor of mast cells. SCF mRNA has been shown to be up-regulated in ischemic myocardial segments in a canine model of myocardial infarction and thus may contribute to mast cell accumulation at ischemic myocardial sites. Franigogiannis, N. G. et al., Circulation 98: 687-798 (1998). Mast cell products (including TGF-B, basic fibroblast growth factor (bFGF), vascular endothelial growth factor (VEGF) and gelatinases A and B) induce fibroblast proliferation, influence extracellular matrix metabolism, and induce angiogenesis. Fang, K. C., et al., J. Immunol. 162: 5528-35 (1999); Takeshi, S., et al., Cardiology 93: 168-74 (2000).

Following a myocardial infarction, neoangiogenesis occurs after the "hot" phase of the inflammatory process subsides (about day 5) coincident with rising levels of VEGF (VEGF peaks at about day 7 and gradually subsides to baseline at about day 14 to about day 21). During this phase of the healing process, endothelial precursor cells (EPCs) are mobilized and recruited to the infarct site. Shinitani, S., et al., Circulation 103: 2776-79 (2001). Without being limited by theory, it has been suggested that the chemokine stromal cell derived factor-1 (SDF-1), which is the ligand for the CXCR-4 chemokine receptor expressed by CD34+ cells, also plays a role in horning of cells to areas of ischemic damage. Ceredini, D. I, et al., Nature Medicine 10: 858-63 (2004); Askari, A., et al., Lancet 362: 697-703 (2003); Yamaguchi, J. et al., Circulation 107: 1322-34 (2003). While it is known that SDF-1 plays a role in hematopoiesis and is involved in migration, homing and survival of hematopoietic progenitors, and while SDF-1 has been implicated in ischemic neovascularization in vivo by augmenting EPC recruitment to ischemic sites (Yamaguchi et al. Circulation 107:1322-1328 (2003), SDF-1's role in neoangiogenesis is not certain. There is suggestive evidence implicating SDF-1. For example, SDF-1 gene expression is upregulated during hypoxia, a deficiency of oxygen in the tissues, by hypoxia inducible factor-1. Furthermore, CD34+ cells are capable of homing to areas of ischemia, rich in SDF-1, including infarcted myocardium. Askari et al., Lancet 362: 697-703 (2003). Moreover, virtually all CD34+ CXCR-4+ cells co-express VEGF-2 and therefore migrate in response to VEGF as well as SDF-1. Peichev M., et al., Blood 95: 952-58 (2000). CD34+CXCR-4+VEGF-1 cells, once recruited, are capable of contributing to neoangiogenesis. Yamaguchi, J. et al., Circulation 107: 1322-34 (2003).

The Peri-Infarct Border Zone

The zone of dysfunctional myocardium produced by coronary artery occlusion extends beyond the infarct region to include a variable boundary of adjacent normal appearing tissue. (Hu, Q., et al., Am. J. Physiol. Heart Circ. Physiol. 291: H648-657 (2006)). This ischemic, but viable, perinfarct zone of tissue separates the central zone of progressive necrosis from surrounding normal myocardium. The peri-infarct zone does not correlate with enzymatic parameters of infarct size and is substantially larger in small infarcts. Stork, A., et al., European Radiol. 16(10): 2350-57 (2006).

Ischemia due to edema and compression of the blood vessels in the border zone may be very important to outcome after an AMI. It is known, for example, that after an AMI, transient ischemia occurs in the border zones, and that percutaneous coronary interventions, which open up the infarct-related artery, can adversely affect the health of the peri-infarct border zones. It has been suggested that intermediate levels of mean blood flow can exist as the result of admixture of peninsulas of ischemic tissue intermingled with regions of normally perfused myocardium at the border of an infarct. (Hu, Q., et al., Am. J. Physiol. Heart Circ Physiol. 291: H648-657 (2006)). However, the boundary of the intermingled coronary microvessels, which in dogs is no more than 3 mm in width, cannot explain the relatively broad region of dysfunctional myocardium surrounding an infarct. Murdock, R H, Jr., et al., Cir. Res. 52: 451-59 (1983); Buda, A J, et al., J. Am. Coll. Cardiol. 8: 150-58 (1986). Progressive dysfunction of this peri-infarct myocardium over time may contribute to the transition from compensated remodeling to progressive heart failure after an AMI.

Heart Failure

Heart failure is a complex clinical syndrome that arises secondary to abnormalities of cardiac structure and/or function that impair the ability of the left ventricle to fill or eject blood. See Hunt, S. J. Am. Coll. Cardiol. 46: e1-e82 (2005). It is a progressive condition where the heart muscle weakens and cannot pump blood efficiently. Patients may be categorized as having heart failure with depressed ejection fraction ("EF")(referred to as "systolic failure"), or having heart failure with a normal EF or heart failure with a preserved EF (referred to as "diastolic failure"). Patients may have significant abnormalities of left ventricle (LV) contraction and relaxation and yet have no symptoms, in which case they are referred to as having "asymptomatic heart failure". When a patient with chronic heart failure deteriorates, the patient is referred to as having "decompensated heart failure", or, if the symptoms arise abruptly, as having "acute decompensated heart failure".

The various diagnostic criteria used to determine the presence of heart failure are shown in the following Table (V. L. Roger, Intl. J. Environ. Res. Public Health 7(4): 1807-30 (2010)):

| Framingham[1] | Boston[2] | European Society of Cardiology[3] n | Gothenburg Score[4] Criteria/method of assessment | |
|---|---|---|---|---|
| MAJOR CRITERIA: Paroxysmal nocturnal dyspnea or orthopnea | CATEGORY I: History Rest dyspnea (4 pts) Orthopnea (4 pts) | 1. Symptoms of heart failure (at rest or during exercise) and 2. Objective | CARDIAC SCORE History of heart disease (1-2 pts) Angina (1-2 pts) | Self-report Self-report |

-continued

| Framingham[1] | Boston[2] | European Society of Cardiology[3] n | Gothenburg Score[4] | Criteria/method of assessment |
|---|---|---|---|---|
| Neck vein distension | Paroxysmal nocturnal dyspnea (3 pts) | evidence of cardiac dysfunction (at rest) and | Edema (1 pt) | Self-report |
| Rales | Dyspnea on walking on level (2 pts) | 3. Response to treatment directed towards heart failure (in cases where diagnosis is in doubt). Criteria 1 and 2 should be fulfilled in all cases | Nocturnal Dyspnea (1 pt) | Self-report |
| Cardiomegaly | | | Rales (1 pt) | Physical exam |
| Acute pulmonary edema S3 gallop | | | | |
| Increased venous pressure ≥16 cm water | Dyspnea on climbing (1 pt) | | Atrial fibrillation (1 pt) | ECG |
| Circ. time ≥25 sec | CATEGORY II: Physical examination | | PULMONARY SCORE | |
| Hepatojugular reflux | | | History of Chronic bronchitis/asthma (1-2 pts) | Self-report |
| MINOR CRITERIA: | Heart rate abnormality (1-2 pts) | | | |
| Ankle edema | Jugular venous pressure elevation (1-2 pts) | | Cough, phlegm, or wheezing (1 pt) | Self-report |
| Night cough | | | Rhonchi (2 pts) | Physical exam |
| Dyspnea on exertion | | | Cardiac and pulmonary score are calculated and used to differentiate Cardiac form pulmonary dyspnea | |
| Hepatomegaly | Lung crackles (1-2 pts) | | | |
| Pleural effusion | | | | |
| Vital capacity decreased ⅓ from maximum | Wheezing (3 pts) | | | |
| Tachycardia rate of ≥120/min) | Third heart sound (3 pts) | | | |
| MAJOR OR MINOR CRITERION: | CATEGORY III: Chest radiography | | | |
| Weight loss ≥4.5 kg in 5 days in response to treatment | Alveolar pulmonary edema (4 pts) | | | |
| HEART FAILURE: present with 2 major or 1 major and 2 minor criteria | Interstitial pulmonary edema (3 pts) | | | |
| | Bilateral pleural effusions (3 pts) | | | |
| | Cardiothoracic ratio ≥0.50 (3 pts) | | | |
| | Upper-zone flow redistribution (2 pts) | | | |
| | HEART FAILURE: Definite 8-12 pts, possible 5-7 pts, unlikely 4 pts or less | | | |

[1] McKee P A, Castelli W P, McNamara P M, Kannel W B. The natural history of congestive heart failure: the Framingham study. N. Engl. J. Med. 285: 1441-1446 (1971)
[2] Carlson K J, Lee D C Goroll A H, Lehy M, Johnson R A, an analysis of physicians' reasons for prescribing long-term digitalis therapy in outpatients. J. Chronic Dis. 38: 733-39 (1985)
[3] Guidelines for the diagnosis of heart failure The Task Force on Heart Failure of the European Society of Cardiology. Eur. Heart J. 16: 741-751 (1995)
[4] Eriksson H, Caidahl K, Larsson B, Ohlson L O, Welin L, Wilhelmsen L, Svardsudd K. Cardiac and pulmonary causes of dyspnoea-validation of a scoring test for clinical-epidemiological use: the Study of Men Born in 1913. Eur. Heart J. 8: 1007-1014 (1987)[

The prognosis of heart failure is poor with reported survival estimates of 50% at 5 years and 10% at 10 years; left ventricular dysfunction is associated with an increase in the risk of sudden death. Id.

To date, no ideal therapy exists for preventing the long term adverse consequences of vascular insufficiency, particularly vascular insufficiency after myocardial infarction. Large vessel revascularization (meaning the successful placement of a stent) is insufficient in addressing increased demands posed by compensatory myocardial hypertrophy. As a result, infarct extension and fibrous replacement commonly occur, regardless of large vessel revascularization, appropriate medical management of ventricular wall stresses, and potential natural, albeit suboptimal, CD34+ cell-mediated neoangiogenesis (one of theories relating to the underlying cause of myocardial infarction is that the ability to mobilize these cells may be biologically limited).

Intense interest has developed in evaluating the ability of endothelial and myocardial precursor cells to limit damage to the myocardium after infarction and to limit or prevent ventricular remodeling. Significant preclinical data and some clinical data demonstrate the safety and potential of cell therapy using a variety of cell precursors (particularly hematopoietic cells) to contribute to neoangiogenesis, limited cardiac myogenesis (principally by fusion), and muscle preservation in the myocardial infarct zone. See, e.g., Jackson, et al., J. Clin. Invest. 107: 1395-1402 (2001); Edelberg, J. M., et al., Cir. Res. 90: e89-e93 (2002); Schichinger, V. et al., New Engl. J. Med. 355 (12): 1210-21 (2006) (using bone marrow-derived progenitor cells); Assmus, B. et al., New Engl. J. Med. 355 (12) 1222-32 (2006) (using bone marrow-derived progenitor cells), but see Lunde, K. et al., New Eng. J. Med. 355 (12): 1199-209 (2006) (using bone marrow-derived progenitor cells).

Bone marrow consists of a variety of precursor and mature cell types, including hematopoietic cells (the precursors of mature blood cells) and stromal cells (the precursors of a broad spectrum of connective tissue cells), both of which appear to be capable of differentiating into other cell types. Wang, J. S. et al., J. Thorac. Cardiovasc. Surg. 122: 699-705 (2001); Tomita, S. et al., Circulation 100 (Suppl. II): 247-256 (1999); Saito, T. et al., Tissue Eng. 1: 327-43 (1995). Unmodified (i.e., not fractionated) marrow or blood-derived cells have been used in several clinical studies, for example, Hamano, K. et al., Japan Cir. J. 65: 845-47 (2001); Strauer, B. E., et al., Circulation 106: 1913-18 (2002); Assmus, et al., Circulation 106: 3009-3017 (2002); Dobert, N. et al., Eur. J. Nuel. Med. Mol. Imaging, 8: 1146-51 (2004); Wollert, K. C. et al., Lancet 364: 141-48 (2004). Since the mononuclear fraction of bone marrow contains stromal cells, hematopoietic precursors, and endothelial precursors, the relative contribution of each of these populations to the observed effects, if any, remains unknown.

CD34 is a hematopoietic stem cell antigen selectively expressed on hematopoietic stem and progenitor cells derived from human bone marrow, blood and fetal liver. Yin et al., Blood 90: 5002-5012 (1997); Miaglia, S. et al., Blood 90: 5013-21 (1997). Cells that express CD34 are termed CD34+. Stromal cells do not express CD34 and are therefore termed CD34−. CD34+ cells isolated from human blood may be capable of differentiating into cardiomyocytes, endothelial cells, and smooth muscle cells in vivo. See Yeh, et al., Circulation 108: 2070-73 (2003). CD34+ cells represent approximately 1% of bone marrow derived nucleated cells; CD34 antigen also is expressed by immature endothelial cell precursors (mature endothelial cells do not express CD34). Peichev, M. et al., Blood 95: 952-58 (2000). In vitro, CD34+ cells derived from adult bone marrow give rise to a majority of the granulocyte/macrophage progenitor cells (CFU-GM), some colony-forming units-mixed (CFU-Mix) and a minor population of primitive erythroid progenitor cells (burst forming units, erythrocytes or BFU-E). Yeh, et al., Circulation 108: 2070-73 (2003). CD34+ cells also may have the potential to differentiate into, or to contribute to, the development of new myocardial muscle, albeit at low frequency.

Techniques have been developed using immunomagnetic bead separation to isolate a highly purified and viable population of CD34+ cells from bone narrow mononuclear cells. See U.S. Pat. Nos. 5,536,475, 5,035,994, 5,130,144, 4,965,205, the contents of each of which is incorporated herein by reference. Two clinical studies support the clinical application of bone marrow derived CD34+ cells after myocardial infarction. See C. Stamm, et al., Lancet 361: 45-46 (2003); Herenstein, B. et al., Blood Supplement, Abs. 2696 (2004).

Animal Models

Peripheral artery disease (PAD), also called peripheral vascular disease (PVD), is modeled by the hind limb model of ischemia in which the femoral artery of the mouse is tied off to simulate peripheral artery disease. PAD, which commonly affects the arteries supplying the leg and includes all diseases caused by the obstruction of large arteries in the arms and legs, can result from atherosclerosis, inflammatory processes leading to stenosis, an embolism or thrombus formation. Restriction of blood flow due to arterial stenosis or occlusion often leads patients to complain of muscle pain on walking (intermittent claudication). Any further reduction in blood flow causes ischemic pain at rest. This condition is called chronic limb ischemia, meaning the demand for oxygen cannot be sustained when resting. Ulceration and gangrene may then supervene in the toes, which are the furthest away from the blood supply, and can result in loss of the involved limb if not treated.

Therapies for limb ischemia have the goals of collateral development and blood supply replenishment. Bone marrow derived CD34+ mononuclear cells have been tested in such hindlimb ischemia models, but the hindlimb ischemia model does not model what takes place in the heart. A preferred therapy after AMI would stop cells from dying during recovery that leads to reverse remodeling and failure, or replace the dying cells with cardiomyocytes.

The closest animal model, the pig model, is not a good model of human disease because (i) all experiments generally are done in nonatherosclerotic animals, (ii) the animals are not treated with angioplasty, (iii) normal pigs do not embolize blood vessels; (iv) circulation of the pig is not exactly the same as human; and (iv) the peri-infarct border zone may not be the same.

A marginal improvement in angina symptoms recently was reported when CD34+ cells were mobilized with G-CSF, apheresed after 5 days, and then injected into an ischemic area of the heart based on Noga mapping. [Northwestern University (2009, Apr. 1). Adult Stem Cell Injections May Reduce Pain And Improve Walking In Severe Angina Patients. ScienceDaily. Retrieved Oct. 21, 2010, from http://www.sciencedaily.com/-/releases/2009/03/090330091706.htm] Data from a phase I trial conducted by the present inventors has provided evidence that subjects treated with at least $10 \times 10^6$ isolated autologous CD34+ hematopoietic stem cells containing a subpopulation of at least $0.5 \times 10^6$ potent CD34+ cells expressing CXCR-4 and having CXCR-4 mediated chemotactic activity (n=9) experienced significant improvement in resting perfusion rates at 6 months compared to subjects receiving 5 million cells (n=6) and control (n=15), as measured by the SPECT Total Severity Score (−256 versus +13, p=0.01). U.S. Patent Applications 61/169,850 and 61/119,552, incorporated herein by reference.

The described invention is a therapy for preventing the long-term adverse consequences of vascular insufficiency, particularly vascular insufficiency that produces expansion of the myocardial infarct area after an AMI progressing to heart failure. It is proposed that administration of a potent dose of a nonexpanded, isolated population of autologous mononuclear cells enriched for CD34+ cells, which further contain a subpopulation of potent CD34+ cells expressing CXCR-4 and having CXCR-4-mediated chemotactic activity administered early or late after occurrence of an AMI can result in a reduction in major adverse cardiac events, including, but not limited to, premature death, recurrent myocardial infarction, the development of congestive heart failure, significant arrhythmias, and acute coronary syndrome, and the worsening of congestive heart failure, significant arrhythmias, and acute coronary syndrome.

SUMMARY OF THE INVENTION

The described invention provides progressive compositions and methods to treat adverse consequences of a progressive myocardial injury due to a vascular insufficiency. According to some embodiments, the vascular insufficiency occurs early after an acute myocardial infarction resulting from underlying disease. According to some embodiments, the vascular insufficiency occurs late after an acute myocardial infarction resulting from underlying disease.

According to one aspect, the described invention provides a method of treating a progressive myocardial injury due to a vascular insufficiency, the method comprising the steps: (a) acquiring a sterile nonexpanded, isolated population of autologous mononuclear cells comprising CD34+ cells, which further contain a subpopulation of potent CD34+/CXCR-4+ cells that have CXCR-4-mediated chemotactic activity from a subject under sterile conditions; (b) sterilely enriching the CD34+ cells which further contain a subpopulation of potent CD34+/CXCR-4+ cells that have CXCR-4-mediated chemotactic activity from the sterile nonexpanded, isolated population of autologous mononuclear cells comprising CD34+ cells, wherein the enriched CD34+ cells which further contain a subpopulation of potent CD34+/CXCR-4+ cells that have CXCR-4-mediated chemotactic activity are a chemotactic hematopoietic stem cell product; (c) administering parenterally through a catheter on a plurality of infusion dates during lifetime of subject a sterile pharmaceutical composition, the sterile pharmaceutical composition comprising: (i) a therapeutically effective amount of the sterile chemotactic hematopoietic stem cell product, wherein the therapeutically effective amount of the chemotactic hematopoietic stem cell product comprises at least $10 \times 10^6$ CD34+ cells which further contain a subpopulation of at least $0.5 \times 10^6$ potent CD34+ cells expressing CXCR-4 and having CXCR-4 mediated chemotactic activity; and (ii) a stabilizing amount of serum, wherein the stabilizing amount of serum is greater than 20% (v/v), wherein the chemotactic hematopoietic stem cell product is further characterized as having the following properties for at least 24 hours when tested in vitro after passage through a catheter: (1) retains the CXCR-4-mediated activity of the chemotactic hematopoietic stem cell product; (2) at least 70% of the cells are CD34+ cells; (3) is at least 70% viable; and (4) is able to form hematopoietic colonies in vitro; (d) optionally administering the chemotactic hematopoietic stem cell product at a plurality of infusion dates during the subject's lifetime; and (e) treating at least one adverse consequence of the progressive vascular insufficiency.

According to one embodiment, step (a) further comprises freezing at least one aliquot of the nonexpanded, isolated population of autologous mononuclear cells containing CD34+ cells, which further contain a subpopulation of potent CD34+/CXCR-4+ cells that have CXCR-4-mediated chemotactic activity at −86° C. and cryostoring the at least one aliquot in the vapor phase of a liquid nitrogen freezer.

According to another embodiment, step (a) further comprises (i) thawing the at least one aliquot of the frozen sterile nonexpanded, isolated population of autologous mononuclear cells containing CD34+ cells which further contain a subpopulation of potent CD34+/CXCR-4+ cells that have CXCR-4-mediated chemotactic activity; (ii) enriching the sterile nonexpanded, isolated population of autologous mononuclear cells for CD34+ cells, which further contain a subpopulation of potent CD34+/CXCR-4+ cells that have CXCR-4-mediated chemotactic activity, wherein the sterile nonexpanded, isolated population of autologous mononuclear cells enriched for CD34+ cells, which further contain a subpopulation of potent CD34+/CXCR-4+ cells that have CXCR-4-mediated chemotactic activity, is a thawed sterile chemotactic hematopoietic stem cell product; and (iii) administering to the subject on a second infusion date a therapeutically effective amount of the sterile thawed sterile chemotactic hematopoietic stem cell product, comprising (a) at least $10 \times 10^6$ CD34+ cells, which further contain a subpopulation of at least $0.5 \times 10^6$ potent CD34+ cells expressing CXCR-4 and having CXCR-4 mediated chemotactic activity; and (b) a stabilizing amount of serum, wherein the stabilizing amount of serum is greater than 20% (v/v), wherein the sterile thawed chemotactic hematopoietic stem cell product is further characterized as having the following properties for at least 24 hours following thawing of the nonexpanded, isolated population of autologous mononuclear cells comprising CD34+ cells, which further contain a subpopulation of potent CD34+/CXCR-4-+ cells that have CXCR-4-mediated chemotactic activity when tested in vitro after passage through a catheter: (1) retains the CXCR-4-mediated activity of the subpopulation of potent CD34+/CXCR-4+ cells that have CXCR-4-mediated chemotactic activity; (2) at least 70% of the cells are CD34+ cells; (3) is at least 70% viable; and (4) is able to form hematopoietic colonies in vitro.

According to another embodiment, enriching step (ii) occurs from at least 1 day to at least 40 years after acquisition of the sterile nonexpanded, isolated population of autologous mononuclear cells comprising CD34+ cells from the subject.

According to another embodiment, the sterile chemotactic hematopoietic stem cell product is administered parenterally through a catheter to the subject within about 48 hours to about 72 hours of thawing step (i).

According to another embodiment, the nonexpanded, isolated population of autologous mononuclear cells comprising CD34+ cells, which further contain a subpopulation of CD34+/CXCR-4+ cells that have CXCR-4-mediated chemotactic activity, is acquired early after an acute myocardial infarction.

According to another embodiment, the nonexpanded, isolated population of autologous mononuclear cells comprising CD34+ cells, which further contain a subpopulation of CD34+/CXCR-4+ cells that have CXCR-4-mediated chemotactic activity, is acquired after peak inflammatory cytokine cascade production in an infarcted area.

According to another embodiment, the nonexpanded, isolated population of autologous mononuclear cells comprising CD34+ cells, which further contain a subpopulation of CD34+/CXCR-4+ cells that have CXCR-4-mediated chemotactic activity, is acquired late after an acute myocardial infarction.

According to another embodiment, the nonexpanded, isolated population of autologous mononuclear cells comprising CD34+ cells, which further contain a subpopulation of CD34+/CXCR-4+ cells that have CXCR-4-mediated chemotactic activity, is acquired from at least 15 days to at least 40 years after occurrence of an acute myocardial infarction.

According to another embodiment, the sterile thawed chemotactic hematopoietic stem cell product is further characterized as having the following properties for at least 48 hours following thawing of the nonexpanded, isolated population of autologous mononuclear cells when tested in vitro after passage through a catheter: (i) is able to form hematopoietic colonies; and (ii) retains at least 2% of the CXCR-4-mediated activity of the subpopulation of potent CD34+/CXCR-4+ cells that have CXCR-4-mediated chemotactic activity.

According to another embodiment, the sterile thawed chemotactic hematopoietic stem cell product is further characterized as having the following properties for at least 72 hours following thawing of the nonexpanded, isolated population of autologous mononuclear cells when tested in vitro after passage through a catheter: (i) is able to form hematopoietic colonies; and (ii) retains at least 2% of the CXCR-4-mediated activity of the subpopulation of potent CD34+/CXCR-4+ cells that have CXCR-4-mediated chemotactic activity.

According to another embodiment, the vascular insufficiency is an ischemia. According to another embodiment, the ischemia is a myocardial ischemia. According to another embodiment, the ischemia is a transient ischemia. According to another embodiment, the ischemia is a chronic myocardial ischemia. According to another embodiment, the vascular insufficiency is a vascular insufficiency after an acute myocardial infarction resulting from underlying disease. According to another embodiment, the ischemia is a peri-infarct border zone ischemia.

According to another embodiment, a first infusion date comprises a specific time interval defined by a first time and a second time, wherein the first time is after peak inflammatory cytokine cascade production in an infarcted area and the second time is before myocardial scar formation in the infarcted area. According to another embodiment, the first time of the first infusion date is at least about 5 days post-infarction. According to another embodiment, the first time of the first infusion date is about 5 days post-infarction and the second time is about 14 days post-infarction.

According to another embodiment, the method treats cardiomyocyte cell death in the peri-infarct border zone, relative to controls. According to another embodiment, the method treats hypoperfusion in the peri-infarct border zone, relative to controls. According to another embodiment, the method treats myocardial hibernation in the peri-infarct border zone, relative to controls. According to another embodiment, the method decreases infarct area, relative to controls. According to another embodiment, wherein the method decreases infarct mass, relative to controls.

According to another embodiment, the progressive myocardial injury is a progressive decline in heart muscle function following the acute myocardial infarction.

According to another embodiment, step (e) comprises treating at least one adverse consequence of an acute myocardial infarction selected from premature death, recurrent myocardial infarction, development of congestive heart failure, development of significant arrhythmias, development of acute coronary syndrome, worsening of congestive heart failure, worsening of significant arrhythmias, and worsening of acute coronary syndrome.

According to another embodiment, the progressive myocardial injury is heart failure.

According to another embodiment, the catheter is a flow control catheter.

According to another embodiment, the catheter is a balloon dilatation catheter.

According to another embodiment, the catheter has an internal diameter of at least about 0.36 mm.

According to another embodiment, administering step (c) is through the catheter into myocardium. According to another embodiment, administering step (c) is through the catheter intravascularly.

According to another embodiment, the pharmaceutical composition further includes at least one compatible active agent. According to another embodiment, the active agent is selected from the group consisting of an angiotensin converting enzyme inhibitor, a beta-blocker, a diuretic, an anti-arrhythmic agent, a hematopoietic stem cell mobilizing agent, a tyrosine kinase receptor agonist, an anti-anginal agent, a vasoactive agent, an anticoagulant agent, a fibrinolytic agent, and a hypercholesterolemic agent.

According to another embodiment, the tyrosine kinase receptor agonist is human neuregulin 1.

According to another aspect, the described invention provides a regimen for treating a progressive myocardial injury due to a vascular insufficiency in a revascularized subject, which comprises (a) administering parenterally through a catheter on a plurality of infusion dates during lifetime of the subject a sterile pharmaceutical composition comprising a sterile chemotactic hematopoietic stem cell product, wherein the sterile chemotactic hematopoietic stem cell product comprises (i) a nonexpanded, isolated population of autologous mononuclear cells enriched for CD34+ cells, which further contain a subpopulation of potent CD34+/CXCR-4+ cells that have CXCR-4-mediated chemotactic activity, wherein the therapeutically effective amount of the chemotactic hematopoietic stem cell product comprises at least $10 \times 10^6$ CD34+ cells which further contain a subpopulation of at least $0.5 \times 10^6$ potent CD34+ cells expressing CXCR-4 and having CXCR-4 mediated chemotactic activity; and (ii) a stabilizing amount of serum, wherein the stabilizing amount of serum is greater than 20% (v/v), wherein the chemotactic hematopoietic stem cell product is further characterized as having the following properties for at least 24 hours following acquisition of the chemotactic hematopoietic stem cell product when tested in vitro after passage through a catheter: (1) retains the CXCR-4-mediated activity of the subpopulation of potent CD34+/CXCR-4+ cells that have CXCR-4-mediated chemotactic activity; (2) at least 70% of the cells are CD34+ cells; (3) is at least 70% viable; and (4) is able to form hematopoietic colonies in vitro; and (b) treating at least one adverse consequence of the progressive vascular insufficiency.

According to one embodiment, the vascular insufficiency is an ischemia. According to another embodiment, the ischemia is a myocardial ischemia. According to another embodiment, the ischemia is a transient ischemia. According to another embodiment, the ischemia is a chronic myocardial ischemia. According to another embodiment, the vascular insufficiency is a vascular insufficiency after an acute myocardial infarction resulting from underlying disease.

According to another embodiment, the nonexpanded, isolated population of autologous mononuclear cells comprising CD34+ cells, which further contain a subpopulation of CD34+/CXCR-4+ cells that have CXCR-4-mediated chemotactic activity, is acquired early after occurrence of an acute myocardial infarction.

According to another embodiment, the nonexpanded, isolated population of autologous mononuclear cells comprising CD34+ cells, which further contain a subpopulation of CD34+/CXCR-4+ cells that have CXCR-4-mediated chemotactic activity, is acquired after peak inflammatory cytokine cascade production in an infarcted area.

According to another embodiment, the nonexpanded, isolated population of autologous mononuclear cells comprising CD34+ cells, which further contain a subpopulation of CD34+/CXCR-4+ cells that have CXCR-4-mediated chemotactic activity, is acquired late after occurrence of an acute myocardial infarction.

According to another embodiment, the nonexpanded, isolated population of autologous mononuclear cells comprising CD34+ cells, which further contain a subpopulation of CD34+/CXCR-4+ cells that have CXCR-4-mediated chemotactic activity, is acquired from at least 15 days to at least 40 years after occurrence of an acute myocardial infarction.

According to another embodiment, a first infusion date comprises a specific time interval defined by a first time and a second time, and wherein the first time is after peak inflammatory cytokine cascade production in an infarcted area and the second time is before myocardial scar formation in the infarcted area.

According to another embodiment, the first time of the first infusion date is at least about 5 days post-infarction. According to another embodiment, the first time of the first infusion date is about 5 days post-infarction and the second time is about 14 days post-infarction. According to another embodiment, the first infusion date is at least 5 days after occurrence of an acute myocardial infarction. According to another embodiment, a second infusion date is at least 30 days after occurrence of an acute myocardial infarction.

According to another embodiment, the ischemia is a peri-infarct border zone ischemia. According to another embodiment, step (b) comprises treating cardiomyocyte cell death in the peri-infarct border zone, relative to controls. According to another embodiment, step (b) comprises treating hypoperfusion in the peri-infarct border zone, relative to controls.

According to another embodiment, step (b) comprises treating myocardial hibernation in the peri-infarct border zone, relative to controls. According to another embodiment, step (b) comprises decreasing infarct area, relative to controls. According to another embodiment, step (b) comprises decreasing infarct mass, relative to controls.

According to another embodiment, step (b) comprises treating at least one adverse consequence of the acute myocardial infarction selected from premature death, recurrent myocardial infarction, development of congestive heart failure, development of significant arrhythmias, development of acute coronary syndrome, worsening of congestive heart failure, worsening of significant arrhythmias, and worsening of acute coronary syndrome.

According to another embodiment, the progressive myocardial injury is a progressive decline in heart muscle function following the acute myocardial infarction. According to another embodiment, the progressive myocardial injury is heart failure.

According to another embodiment, the catheter is a flow control catheter. According to another embodiment, the catheter is a balloon dilatation catheter. According to another embodiment, the catheter has an internal diameter of at least about 0.36 mm.

According to another embodiment, the composition is administered through the catheter into myocardium. According to another embodiment, the composition is administered through the catheter intravascularly.

According to another embodiment, the pharmaceutical composition further includes at least one compatible active agent. According to another embodiment, the active agent is selected from the group consisting of an angiotensin converting enzyme inhibitor, a beta-blocker, a diuretic, an anti-arrhythmic agent, a hematopoietic stem cell mobilizing agent, a tyrosine kinase receptor agonist, an anti-anginal agent, a vasoactive agent, an anticoagulant agent, a fibrinolytic agent, and a hypercholesterolemic agent.

According to another embodiment, the tyrosine kinase receptor agonist is human neuregulin 1.

BRIEF DESCRIPTION OF THE FIGURES

FIG. 2 shows the migratory efficiency of the formulated chemotactic hematopoietic stem cell product comprising CD34+ cells of the invention.

FIG. 3 shows the improved stability of CD34+ cells formulated in human serum.

DETAILED DESCRIPTION

Figure 1:
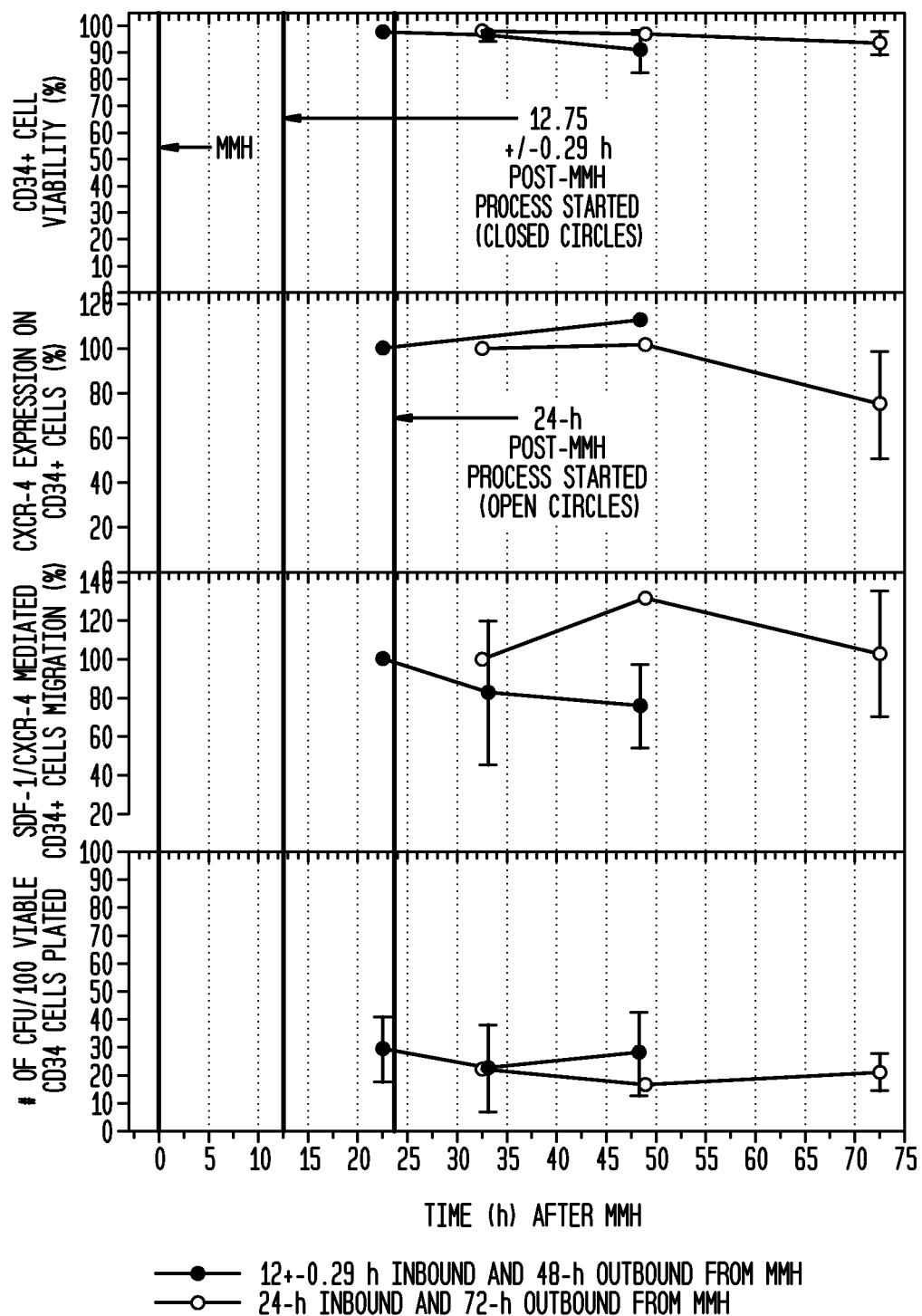
FIG. 1 shows that the functional viability of the chemotactic hematopoietic cell product of the invention at 72 hours is equivalent to that at 48 hours.

The present invention describes compositions and methods for preventing early or late adverse consequences of vascular insufficiency, including, but not limited to, vascular insufficiency that occurs early or late after an acute myocardial infarction resulting from underlying disease.

GLOSSARY

The term "administer" and its various grammatical forms as used herein means to give or to apply. The term "administering" as used herein includes in vivo administration, as well as administration directly to tissue ex vivo. Generally, compositions may be administered systemically either parenterally or topically in dosage unit formulations containing conventional nontoxic pharmaceutically acceptable carriers, adjuvants, and vehicles as desired, or may be locally administered by means such as, but not limited to, injection, implantation, grafting, topical application, or parenterally. A means of administering cells may include, but is not limited to, infusion.

As used herein, the term "aliquot" refers to a portion of a total amount.

As used herein, the term "angiogenesis" refers to the process of formation and development of blood vessels.

The terms "apoptosis" or "programmed cell death" refer to a highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

The term "c-kit" refers to a protein on the surface of some cells that binds to stem cell factor (a substance that causes certain types of cells to grow). Altered forms of this receptor may be associated with some types of cancer.

The term "cardiac biomarkers" refers to enzymes, proteins and hormones associated with heart function, damage or failure that are used for diagnostic and prognostic purposes. Different biomarkers have different times that their levels rise, peak, and fall within the body, allowing them to be used not only to track the progress of a heart attack but to estimate when it began and to monitor for recurrence. Some of the tests are specific for the heart while others also are elevated by skeletal muscle damage. Current cardiac biomarkers include, but are not limited to CK (creatine phosphokinase or creatine kinase) and CK-MB (creatine kinase-myoglobin levels (to help distinguish between skeletal and heart muscle)), troponin (blood levels of troponin I or T will remain high for 1-2 weeks after a heart attack; troponin generally is not affected by damage to other muscles), myoglobin (to determine whether muscle, particularly heart muscle, has been injured), and BNP (brain natriuretic peptide) or NT-proBNP (N-terminal prohormone brain natriuretic peptide (to help diagnose heart failure and grade the severity of that heart failure).

The term "cardiac catheterization" refers to a procedure in which a catheter is passed through an artery to the heart, and into a coronary artery. This procedure produces angiograms (i.e., x-ray images) of the coronary arteries and the left ventricle, the heart's main pumping chamber, which can be used to measure pressures in the pulmonary artery, and to monitor heart function.

The term "CD34+ cells" as used herein refers to hematopoietic stem and progenitor cells derived from human bone marrow that "are positive for" i.e., "express", a hematopoietic stem cell antigen, at least a subpopulation of which express CXCR-4, and that can migrate to areas of injury. The chemotactic hematopoietic stem cell product of the described invention that is enriched for CD34+ cells does not co-express VEGF-2 (<1%).

The term "CD38" refers to a protein marker present on macrophages, dendritic cells, and activated B and NK cells, which may mediate the adhesion between lymphocytes and endothelial cells.

The terms "CD45" and "common leukocyte antigen" refer to a protein tyrosine phosphatase (PTP) located in hematopoietic cells except erythrocytes and platelets.

The term "CD59" refers to a glycosylphosphatidylinositol (GPI)-linked membrane glycoprotein which protects human cells from complement-mediated lysis.

The term "CXCR-4" as used herein refers to a G-protein-linked chemokine receptor.

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The term "colony stimulating factor" refers to a cytokine responsible for controlling the production of white blood cells. Types of colony stimulating factors include granulocyte colony stimulating factor (G-CSF), macrophage colony stimulating factor (M-CSF), and granulocyte macrophage colony stimulating factor (GM-CSF).

The term "hematopoietic stem cell" refers to a cell isolated from the blood or from the bone marrow that can renew itself, differentiate to a variety of specialized cells, mobilize out of the bone marrow into the circulating blood, and can undergo programmed cell death (apoptosis). In some embodiments of the described invention, hematopoietic stem cells derived from human subjects express at least one type of cell surface marker, including, but not limited to, CD34, CD38, HLA-DR, c-kit, CD59, Sca-1, Thy-1, and/or CXCR-4, or a combination thereof.

"HLA-DR" refers to a human class II histocompatibility antigen present on several cell types, including antigen-presenting cells, B cells, monocytes, macrophages, and activated T cells.

The term "interleukin" as used herein refers to a cytokine secreted by white blood cells as a means of communication with other white blood cells.

The terms "VEGF-1" or "vascular endothelial growth factor-1" are used interchangeably herein to refer to a cytokine that mediates numerous functions of endothelial cells including proliferation, migration, invasion, survival, and permeability. VEGF is believed to be critical for angiogenesis.

The term "chemokine" as used herein refers to a class of chemotactic cytokines that signal leukocytes to move in a specific direction. The terms "chemotaxis" or "chemotactic" refer to the directed motion of a motile cell or part along a chemical concentration gradient towards environmental conditions it deems attractive and/or away from surroundings it finds repellent.

The term "complete blood count" (CBC) refers to a laboratory test that provides detailed information about the amount and the quality of each of the blood cell types. It usually includes a measurement of each of the three major blood cells (red blood cells, white blood cells, and platelets) and a measure of the hemoglobin and hematocrit. "Hemoglobin" (HOB) refers to the number of grams of hemoglobin in a deciliter of blood (g/dL). Normal hemoglobin levels in healthy adult human subjects are about 14 g/dL to about 18 g/dL for men and about 12 g/dL to about 16 g/dL for women. As a rough guideline, hemoglobin generally should be about one-third the hematocrit. "Red Blood Cell Count" (RBC) refers to the total number of red blood cells in a quantity of blood. Normal ranges in human subjects are about 4.5 million cells/mm$^3$ to about 6.0 million cells/mm$^3$ for men and about 4.0 million cells/mm$^3$ to about 5.5 million cells/mm$^3$ for women. "White Blood Cell Count" (WBC) refers to the total number of while blood cells or leukocytes in a quantity of blood. Normal ranges in human subjects are about $4.3 \times 10^3$ cells/mm$^3$ to about $10.8 \times 10^3$ cells/mm$^3$. "Hematocrit" (HCT) refers to the proportion of red blood cells as a percentage of total blood volume. A normal hematocrit for human subjects is about 40% to about 55% for men and about 35% to about 45% for women.

The term "disease" or "disorder", as used herein, refers to an impairment of health or a condition of abnormal functioning. The term "syndrome," as used herein, refers to a pattern of symptoms indicative of some disease or condition. The term "condition", as used herein, refers to a variety of health states and is meant to include disorders or diseases caused by any underlying mechanism or disorder, injury, and the promotion of healthy tissues and organs.

As used herein, the term "early" refers to being or occurring at or near the beginning of a period of time or series of events. As used herein, the term "late" refers to being or occurring at an advanced period of time or stage of a series of events.

As used herein, the term "enriching" or "purifying" refers to increasing the fraction of cells of one type over the fraction of that type in a starting preparation. Cells may be enriched using any of the various markers expressed, or not expressed, on certain cells in combination with suitable separation techniques. Suitable separation techniques include, but are not limited to, immunomagnetic bead separation, affinity chromatography, density gradient centrifugation, and flow cytometry.

As used herein, the term "nonexpanded" refers to not being increased or amplified in number of cells by in vitro culture.

As used herein, the term "inflammation" refers to a response to infection and injury in which cells involved in detoxification and repair are mobilized to the compromised site by inflammatory mediators. Inflammation often is characterized by a strong infiltration of leukocytes at the site of inflammation, particularly neutrophils (polymorphonuclear cells). These cells promote tissue damage by releasing toxic substances at the vascular wall or in uninjured tissue.

Regardless of the initiating agent, the physiologic changes accompanying acute inflammation encompass four main features: (1) vasodilation, which results in a net increase in blood flow, is one of the earliest s physical responses to acute tissue injury; (2) in response to inflammatory stimuli, endothelial cells lining the venules contract, widening the intracellular junctions to produce gaps, leading to increased vascular permeability, which permits leakage of plasma proteins and blood cells out of blood vessels; (3) inflammation often is characterized by a strong infiltration of leukocytes at the site of inflammation, particularly neutrophils (polymorphonuclear cells). These cells promote tissue damage by releasing toxic substances at the vascular wall or in uninjured tissue; and (4) fever, produced by pyrogens released from leukocytes in response to specific stimuli.

During the inflammatory process, soluble inflammatory mediators of the inflammatory response work together with cellular components in a systemic fashion in the attempt to contain and eliminate the agents causing physical distress. The terms "inflammatory" or immuno-inflammatory" as used herein with respect to mediators refers to the molecular mediators of the inflammatory process. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, proinflammatory cytokines, including, but not limited to, interleukin-1, interleukin-4, interleukin-6, interleukin-S, tumor necrosis factor (TNF), interferon-gamma, and interleukin 12.

The term "in-date" refers to the time interval between completion of acquiring a preparation comprising an enriched population of potent CD34+ cells from a subject under sterile conditions and initiating sterilely purifying potent CD34+ cells from the preparation. The term "out-date" refers to the time interval between completion of acquiring a preparation comprising an enriched population of potent CD34+ cells from a subject under sterile conditions and infusing the formulated pharmaceutical composition comprising a chemotactic hematopoietic cell product into the subject.

The terms "infuse" or "infusion" as used herein refer to the introduction of a fluid other than blood into a blood vessel of a subject, including humans, for therapeutic purposes.

The "infusion solution" of the described invention without autologous serum contains phosphate buffered saline (PBS) supplemented with 25 USP units/ml of heparin and 1% human serum albumin (HSA). In some embodiments, the infusion solution is supplemented with serum. In some embodiments, the serum is autologous.

The term "injury" refers to damage or harm caused to the structure or function of the body of a subject caused by an agent or force, which may be physical or chemical. The term "vascular injury" refers to injury to the vasculature (i.e., the vascular network, meaning the network of blood vessels or ducts that convey fluids, such as, without limitation, blood or lymph). The term "myocardial injury" refers to injury to the myocardium of the heart.

The term "macrophage" as used herein refers to a mononuclear, actively phagocytic cell arising from monocytic stem cells in the bone marrow. These cells are widely distributed in the body and vary in morphology and motility. Phagocytic activity typically is mediated by serum recognition factors, including certain immunoglobulins and components of the complement system, but also may be nonspecific. Macrophages also are involved in both the production of antibodies and in cell-mediated immune responses, particularly in presenting antigens to lymphocytes. They secrete a variety of immunoregulatory molecules.

The terms "microbe" or "microorganism" are used interchangeably herein to refer to an organism too small to be seen clearly with the naked eye, including, but not limited to, microscopic bacteria, fungi (molds), algae, protozoa, and viruses.

The term "modulate" as used herein means to regulate, alter, adapt, or adjust to a certain measure or proportion.

The term "myocardial infarction" refers to death or permanent damage to heart muscle. Most heart attacks are caused by blockage of coronary arteries that interrupts flow of blood and oxygen to the heart muscle, leading to death of heart cells in that area. The damaged heart muscle loses its ability to contract, leaving the remaining heart muscle to compensate for the weakened area. The described invention includes steps related to evaluating the suitability of subjects for treatment according to the described invention by using tests to look at the size, shape, and function of the heart as it is beating, to detect changes to the rhythm of the heart, and to detect and evaluate damaged tissues and blocked arteries. Examples of such tests include, but are not limited to, electrocardiography, echocardiography, coronary angiography, and nuclear ventriculography. Cardiac biomarkers also are used to evaluate the suitability of subjects for treatment according to the described invention.

The term "necrosis" refers to the premature death of cells and living tissue induced by external factors, such as infection, toxins or trauma. Necrotic tissue undergoes chemical reactions different from those of apoptotic tissue. Necrosis typically begins with cell swelling, chromatin digestion, disruption of the plasma membrane and of organelle membranes. Damage to the lysosome membrane can trigger release of lysosomal enzymes, destroying other parts of the cell. Late necrosis is characterized by extensive DNA hydrolysis, vacuolation of the endoplasmic reticulum, organelle breakdown and cell lysis. The release of intracellular content after plasma membrane rupture is the cause of inflammation in necrosis. Released lysosomal enzymes can trigger a chain reaction of further cell death. Necrosis of a sufficient amount of contiguous tissue can result in tissue death or gangrene.

The term "perfusion" as used herein refers to the process of nutritive delivery of arterial blood to a capillary bed in biological tissue. Perfusion ("F") can be calculated with the formula $F=((PA-Pv)/R)$ wherein PA is mean arterial pressure, Pv is mean venous pressure, and R is vascular resistance. Tissue perfusion can be measured in vivo, by, for example, but not limited to, magnetic resonance imaging (MRI) techniques. Such techniques include using an injected contrast agent and arterial spin labeling (ASL) (wherein arterial blood is magnetically tagged before it enters into the tissue of interest and the amount of labeling is measured and compared to a control recording).

The term "persisting" as used herein refers to that which is never-ceasing or indefinitely continuous.

As used herein, the term "potent" or "potency" refers to the necessary biological activity of the chemotactic hematopoietic stem cell product of the described invention, i.e., potent cells of the described invention remain viable, are capable of mediated mobility, and are able to grow, i.e., to form hematopoietic colonies in an in vitro CFU assay.

The term "progenitor cell" as used herein refers to an immature cell in the bone marrow that may be isolated by growing suspensions of marrow cells in culture dishes with added growth factors. Progenitor cells mature into precursor cells that mature into blood cells. Progenitor cells are referred to as colony-forming units (CFU) or colony-forming cells (CFC). The specific lineage of a progenitor cell is indicated by a suffix, such as, but not limited to, CFU-E (erythrocytic), CFU-GM (granulocytic/macrophage), and CFU-GEMM (pluripotent hematopoietic progenitor).

The term "progressive" as used herein refers to that which gradually advances in extent.

The term "repair" as used herein as a noun refers to any correction, reinforcement, reconditioning, remedy, making up for, making sound, renewal, mending, patching, or the like that restores function. When used as a verb, it means to correct, to reinforce, to recondition, to remedy, to make up for, to make sound, to renew, to mend, to patch or to otherwise restore function. In some embodiments "repair" includes full repair and partial repair.

The term "reverse" as used herein refers to a change to the contrary, or to a turning backward in nature or effect.

The term "Sca-1" or "stem cell antigen-1" refers to a surface protein component in a signaling pathway that affects the self-renewal ability of mesenchymal stem cells.

The term "stem cells" refers to undifferentiated cells having high proliferative potential with the ability to self-renew that can generate daughter cells that can undergo terminal differentiation into more than one distinct cell phenotype.

The term "stent" is used to refer to a small tube used to prop open an artery. The stent is collapsed to a small diameter, put over a balloon catheter, inserted through a main artery in the groin (femoral artery) or arm (brachial artery) and threaded up to the narrowed/blocked section of the artery. When it reaches the right location, the balloon is inflated slightly to push any plaque out of the way and to expand the artery (balloon angioplasty). When the balloon is inflated, the stent expands, locks in place and forms a scaffold to hold the artery open. The stent stays in the artery permanently. In certain subjects, a stent reduces the renarrowing that occurs after balloon angioplasty or other procedures that use catheters. A stent also may help restore normal blood flow and keep an artery open if it has been torn or injured by the balloon catheter. Reclosure (restenosis) may be a problem with the stent procedure. Drug-eluting stents are stents coated with drugs that are slowly released. These drugs may help keep the blood vessel from redosing.

The terms "subject" and "patients" are used interchangeably herein and include animal species of mammalian origin, including humans.

The term "Thy-1" refers to the Ig superfamily cell surface glycoprotein Thy-1 expressed on immune cells and neurons of rodents and humans, which is hypothesized to function in cell adhesion and signal transduction in T cell differentiation, proliferation, and apoptosis.

As used herein the terms "treat" or "treating" are used interchangeably to include abrogating, substantially inhibiting, slowing or reversing the progression of a condition, substantially ameliorating clinical or aesthetical symptoms of a condition, substantially preventing the appearance of clinical or aesthetical symptoms of a condition, and protecting from harmful or annoying stimuli. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "vascular insufficiency" refers to insufficient blood flow.

The described invention provides progressive myocardial injury-preventing pharmaceutical compositions and methods to treat or prevent a progressive myocardial injury due to a vascular insufficiency that occurs early or late. The terms "formulation" and "composition" are used interchangeably herein to refer to a product of the described invention that comprises all active and inert ingredients. The term "active" refers to the ingredient, component or constituent of the compositions of the described invention responsible for the intended therapeutic effect. The terms "pharmaceutical formulation" or "pharmaceutical composition" as used herein refer to a formulation or composition that is employed to prevent, reduce in intensity, cure or otherwise treat a target condition or disease.

In one aspect of the described invention, the hematopoietic stem cells of the described invention can migrate, meaning that they can move from one place, location or area to another. In one embodiment, hematopoietic stem cell migration is driven by CXCR-4 chemotaxis.

Compositions

The progressive myocardial injury-preventing pharmaceutical composition of the described invention comprises a chemotactic hematopoietic stem cell product, the chemotactic hematopoietic stem cell product comprising a nonexpanded, isolated population of autologous mononuclear cells enriched for CD34+ cells, which further contain a subpopulation of potent CD34+CXCR-4+ cells that have chemotactic activity. In some embodiments, this chemotactic activity is mediated by SDF-1, and/or CXCR-4. According to some embodiments, the chemotactic hematopoietic stem cell product is prepared by isolating or purifying CD34+ hematopoietic stem cells from bone marrow, umbilical cord blood, peripheral blood, mobilized peripheral blood, umbilical cord, or adipose tissue harvested from the subject. According to some embodiments, the chemotactic hematopoietic stem cell product is prepared by isolating or purifying CD34+ hematopoietic stem cells from mobilized peripheral blood. Treatment with hematopoietic growth factors has been shown to cause a marked rise in the number of hematopoietic progenitor cells in the peripheral blood as measured by the presence of CD34+ cells or as measured in a colony formation assay as CFUs. Such mobilized-peripheral blood hematopoietic stem cells (HSCs) have been used for transplantation, immunotherapy, and cardiovascular regenerative medicine. Colony stimulating factors, for example, are agents used for hematopoietic stem cell mobilization. Examples of colony stimulating factors include, without limitation, G-CSF, GM-CSF, and pharmaceutically acceptable analogs and derivatives thereof. For example, filgrastim, a G-CSF analog produced by recombinant technology, is marketed under the brand names Neupogen®

(Amgen); Religrast® (Reliance Life Sciences), Nugraf® (Zenotech Laboratories, Ltd., and Neukine® (Intas Biopharmaceuticals).

According to some embodiments, the nonexpanded, isolated population of autologous mononuclear cells comprising CD34+ cells which further contain a subpopulation of potent CD34+/CXCR-4+ cells that have CXCR-4-mediated chemotactic activity can be acquired from the subject at any time. According to some embodiments, the nonexpanded, isolated population of autologous mononuclear cells is acquired early after an AMI. According to some such embodiments, the nonexpanded, isolated population of autologous mononuclear cells is acquired 4 days, 5 days, 6 days, 7 days, 8 days, 9 days, 10 days, 11 days, 12 days, 13 days, 14 days or more after the occurrence of an AMI. According to some embodiments, the nonexpanded, isolated population of autologous mononuclear cells comprising CD34+ cells which further contain a subpopulation of potent CD34+/CXCR-4+ cells that have CXCR-4-mediated chemotactic activity is acquired late after the occurrence of an AMI. According to some such embodiments, the nonexpanded, isolated population of autologous mononuclear cells is acquired at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 60 days, at least 90 days, at least 120 days, at least 150 days, at least 180 days, or more from the AMI. According to some embodiments, the nonexpanded, isolated population of autologous mononuclear cells comprising CD34+ cells which further contain a subpopulation of potent CD34+/CXCR-4+ cells that have CXCR-4-mediated chemotactic activity is acquired at least 1 month, at least 2 months, at least 3 months, at least 4 months, at least 5 months, at least 6 months, at least 7 months, at least 8 months, at least 9 months, at least 10 months, at least 11 months, at least 12 months, at least 16 months, at least 24 months, at least 30 months, at least 36 months, at least 42 months, at least 48 months, at least 54 months, at least 60 months, at least 66 months, at least 72 months, at least 78 months, at least 84 months, at least 90 months, at least 96 months, at least 102 months, at least 108 months, at least 114 months, at least 120 months, at least 126 months, at least 132 months, at least 138 months, at least 144 months, at least 150 months, at least 156 months, at least 162 months, at least 168 months, at least 174 months, at least 180 months, at least 186 months, at least 192 months, at least 198 months, at least 204 months, at least 210 months, at least 216 months, at least 222 months, at least 228 months, at least 234 months, at least 240 months or more after occurrence of an AMI. According to some such embodiments, the nonexpanded, isolated population of autologous mononuclear cells comprising CD34+ cells which further contain a subpopulation of potent CD34+/CXCR-4+ cells that have CXCR-4-mediated chemotactic activity is acquired at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI. According to some embodiments, the nonexpanded, isolated population of autologous mononuclear cells comprising CD34+ cells which further contain a subpopulation of potent CD34+/CXCR-4+ cells that have CXCR-4-mediated chemotactic activity, once acquired, is frozen at −86° C. and cryostored in the vapor phase of a liquid nitrogen freezer as a plurality of aliquots for later usage.

According to the described invention, at least 70% of potent cells in the nonexpanded, isolated population of autologous mononuclear cells enriched for CD34+ cells, which further contain a subpopulation of potent CD34+ cells expressing CXCR-4 and having chemotactic activity are CD34+ cells. In some embodiments, at least 75% of cells in the nonexpanded, isolated population of autologous mononuclear cells enriched for CD34+ cells containing a subpopulation of potent CD34+ cells expressing CXCR-4 and having chemotactic activity are CD34+ cells. In some embodiments, at least 80% of potent cells in the nonexpanded, isolated population of autologous mononuclear cells enriched for CD34+ cells, which further contain a subpopulation of potent CD34+ cells expressing CXCR-4 and having chemotactic activity are CD34+ cells. In some embodiments, at least 85% of potent cells in the nonexpanded, isolated population of autologous mononuclear cells enriched for CD34+ cells, which further contain a subpopulation of potent CD34+ cells expressing CXCR-4 and having chemotactic activity are CD34+ cells. In some embodiments, at least 90% of potent cells in the nonexpanded, isolated population of autologous mononuclear cells enriched for CD34+ cells, which further contain a subpopulation of potent CD34+ cells expressing CXCR-4 and having chemotactic activity are CD34+ cells. In some embodiments, at least 95% of potent cells in the nonexpanded, isolated population of autologous mononuclear cells enriched for CD34+ cells, which further contain a subpopulation of potent CD34+ cells expressing CXCR-4 and having chemotactic activity are CD34+ cells.

According to another embodiment, at least about 70% of the nonexpanded, isolated population of autologous mononuclear cells enriched for CD34+ cells, which further contain a subpopulation of potent CD34+ cells expressing CXCR-4 and having chemotactic activity are viable for at least about 24 hours following acquisition of the chemotactic hematopoietic stem cell product. According to another embodiment, at least about 75% of the nonexpanded, isolated population of autologous mononuclear cells enriched for CD34+ cells, which further contain a subpopulation of potent CD34+ cells expressing CXCR-4 and having chemotactic activity are viable for at least about 24 hours following acquisition of the chemotactic hematopoietic stem cell product. According to another embodiment, at least about 80% of the nonexpanded, isolated population of autologous mononuclear cells enriched for CD34+ cells, which further contain a subpopulation of potent CD34+ cells expressing CXCR-4 and having chemotactic activity are viable for at least 24 hours following acquisition of the chemotactic hematopoietic stem cell product. According to another embodiment, at least about 85% of the nonexpanded, isolated population of autologous mononuclear cells enriched for CD34+ cells, which further contain a subpopulation of potent CD34+ cells expressing CXCR-4 and having chemotactic activity are viable for at least 24 hours following acquisition of the chemotactic hematopoietic stem cell product. In some embodiments, at least about 90% of the nonexpanded, isolated population of autologous mononuclear cells enriched for CD34+ cells, which further contain a subpopulation of potent CD34+ cells expressing CXCR-4 and having chemotactic activity are viable for at least 24 hours following acquisition of the chemotactic hematopoietic stem cell product. In some embodiments, at least about 95% of the nonexpanded, isolated population of autologous mononuclear cells enriched for CD34+ cells, which further contain a subpopulation of potent CD34+ cells expressing CXCR-4 and having chemotactic activity are viable for at least about 24 following acquisition of the chemotactic hematopoietic stem cell product.

According to another embodiment, at least about 70% of the nonexpanded, isolated population of autologous mononuclear cells enriched for CD34+ cells, which further contain a subpopulation of potent CD34+ cells expressing CXCR-4 and having chemotactic activity are viable for at least about 48 hours following acquisition of the chemotactic hematopoietic stem cell product. According to another embodiment, at least about 75% of the nonexpanded, isolated population of autologous mononuclear cells enriched for CD34+ cells, which further contain a subpopulation of potent CD34+ cells expressing CXCR-4 and having chemotactic activity are viable for at least about 48 hours following acquisition of the chemotactic hematopoietic stem cell product. According to another embodiment, at least about 80% of the nonexpanded, isolated population of autologous mononuclear cells enriched for CD34+ cells, which further contain a subpopulation of potent CD34+ cells expressing CXCR-4 and having chemotactic activity are viable for at least 48 hours following acquisition of the chemotactic hematopoietic stem cell product. According to another embodiment, at least about 85% of the nonexpanded, isolated population of autologous mononuclear cells enriched for CD34+ cells, which further contain a subpopulation of potent CD34+ cells expressing CXCR-4 and having chemotactic activity are viable for at least 48 hours following acquisition of the chemotactic hematopoietic stem cell product. In some embodiments, at least about 90% of the nonexpanded, isolated population of autologous mononuclear cells enriched for CD34+ cells containing a subpopulation of potent CD34+ cells expressing CXCR-4 and having chemotactic activity are viable for at least 48 hours following acquisition of the chemotactic hematopoietic stem cell product. In some embodiments, at least about 95% of the nonexpanded, isolated population of autologous mononuclear cells enriched for CD34+ cells, which further contain a subpopulation of potent CD34+ cells expressing CXCR-4 and having chemotactic activity are viable for at least about 48 following acquisition of the chemotactic hematopoietic stem cell product.

According to another embodiment, at least about 70% of the nonexpanded, isolated population of autologous mononuclear cells enriched for CD34+ cells, which further contain a subpopulation of potent CD34+ cells expressing CXCR-4 and having chemotactic activity are viable for at least about 72 hours following acquisition of the chemotactic hematopoietic stem cell product. According to another embodiment, at least about 75% of the nonexpanded, isolated population of autologous mononuclear cells enriched for CD34+ cells, which further contain a subpopulation of potent CD34+ cells expressing CXCR-4 and having chemotactic activity are viable for at least about 72 hours following acquisition of the chemotactic hematopoietic stem cell product. According to another embodiment, at least about 80% of the nonexpanded, isolated population of autologous mononuclear cells enriched for CD34+ cells, which further contain a subpopulation of potent CD34+ cells expressing CXCR-4 and having chemotactic activity are viable for at least 72 hours following acquisition of the chemotactic hematopoietic stem cell product. According to another embodiment, at least about 85% of the nonexpanded, isolated population of autologous mononuclear cells enriched for CD34+ cells, which further contain a subpopulation of potent CD34+ cells expressing CXCR-4 and having chemotactic activity are viable for at least 72 hours following acquisition of the chemotactic hematopoietic stem cell product. In some embodiments, at least about 90% of the nonexpanded, isolated population of autologous mononuclear cells enriched for CD34+ cells, which further contain a subpopulation of potent CD34+ cells expressing CXCR-4 and having chemotactic activity are viable for at least 72 hours following acquisition of the chemotactic hematopoietic stem cell product. In some embodiments, at least about 95% of the nonexpanded, isolated population of autologous mononuclear cells enriched for CD34+ cells, which further contain a subpopulation of potent CD34+ cells expressing CXCR-4 and having chemotactic activity are viable for at least about 72 following acquisition of the chemotactic hematopoietic stem cell product.

According to another embodiment, the nonexpanded, isolated population of autologous mononuclear cells enriched for CD34+ cells, which further contain a subpopulation of potent CD34+ cells having chemotactic activity can form hematopoietic colonies in vitro for at least about 24 hours following acquisition from the subject of the chemotactic hematopoietic stem cell product. According to another embodiment, the nonexpanded, isolated population of autologous mononuclear cells enriched for CD34+ cells, which further contain a subpopulation of potent CD34+ cells expressing CXCR-4 and having chemotactic activity can form hematopoietic colonies in vitro for at least about 48 hours following acquisition from the subject of the chemotactic hematopoietic stem cell product. According to another embodiment, the nonexpanded, isolated population of autologous mononuclear cells enriched for CD34+ cells, which further contain a subpopulation of potent CD34+ cells expressing CXCR-4 and having chemotactic activity can form hematopoietic colonies in vitro for at least about 72 hours following acquisition from the subject of the chemotactic hematopoietic stem cell product.

According to another embodiment, the progressive myocardial injury-preventing composition further comprises at least about 10 million isolated CD34+ cells acquired from the subject, which further contain a subpopulation of potent CD34+ cells expressing CXCR-4 and having CXCR-4-mediated chemotactic activity. According to another embodiment, the progressive myocardial injury-preventing composition further comprises at least about 11 million isolated CD34+ cells acquired from the subject, which further contain a subpopulation of potent CD34+ cells expressing CXCR-4 and having CXCR-4-mediated chemotactic activity. According to another embodiment, the progressive myocardial injury-preventing composition further comprises at least about 12 million isolated CD34+ cells acquired from the subject, which further contain a subpopulation of potent CD34+ cells expressing CXCR-4 and having CXCR-4-mediated chemotactic activity. According to another embodiment, the progressive myocardial injury-preventing composition further comprises at least about 13 million isolated CD34+ cells acquired from the subject, which further contain a subpopulation of potent CD34+ cells expressing CXCR-4 and having CXCR-4-mediated chemotactic activity. According to another embodiment, the progressive myocardial injury-preventing composition further comprises at least about 14 million isolated CD34+ cells acquired from the subject, which further contain a subpopulation of potent CD34+ cells expressing CXCR-4 and having CXCR-4-mediated chemotactic activity. According to another embodiment, the progressive myocardial injury-preventing composition further comprises at least about 15 million isolated CD34+ cells acquired from the subject, which further contain a subpopulation of potent CD34+ cells expressing CXCR-4 and having CXCR-4-mediated chemotactic activity. According to another embodiment, the progressive myocardial injury-preventing composition further comprises at least about 20 million isolated CD34+ cells acquired from the subject, which further contain a subpopulation of potent CD34+ cells expressing CXCR-4 and having CXCR-4-mediated chemotactic activity. According to another embodiment, the progressive myocardial injury-preventing composition further comprises at least about 30 million isolated CD34+ cells acquired from the subject, which further contain a subpopulation of potent CD34+ cells expressing CXCR-4 and having CXCR-4-mediated chemotactic activity. According to another embodiment, the progressive myocardial injury-preventing composition further comprises at least about 40 million isolated CD34+ cells acquired from the subject, which further contain a subpopulation of potent CD34+ cells expressing CXCR-4 and having CXCR-4-mediated chemotactic activity. According to another embodiment, the progressive myocardial injury-preventing composition further comprises at least about 50 million isolated CD34+ cells acquired from the subject, which further contain a subpopulation of potent CD34+ cells expressing CXCR-4 and having CXCR-4-mediated chemotactic activity. According to another embodiment, the progressive myocardial injury-preventing composition further comprises at least about 60 million isolated CD34+ cells acquired from the subject, which further contain a subpopulation of potent CD34+ cells expressing CXCR-4 and having CXCR-4-mediated chemotactic activity. According to another embodiment, the progressive myocardial injury-preventing composition further comprises at least about 70 million isolated CD34+ cells acquired from the subject, which further contain a subpopulation of potent CD34+ cells expressing CXCR-4 and having CXCR-4-mediated chemotactic activity. According to another embodiment, the progressive myocardial injury-preventing composition further comprises at least about 80 million isolated CD34+ cells acquired from the subject, which further contain a subpopulation of potent CD34+ cells expressing CXCR-4 and having CXCR-4-mediated chemotactic activity. According to another embodiment, the progressive myocardial injury-preventing composition further comprises at least about 90 million isolated CD34+ cells acquired from the subject, which further contain a subpopulation of potent CD34+ cells expressing CXCR-4 and having CXCR-4-mediated chemotactic activity. According to another embodiment, the progressive myocardial injury-preventing composition further comprises at least about 100 million isolated CD34+ cells acquired from the subject, which further contain a subpopulation of potent CD34+ cells expressing CXCR-4 and having CXCR-4-mediated chemotactic activity.

For use in the present invention, CD34+ cells may be enriched/selected by any techniques known to the skilled artisan. For example, in some embodiments, the isolated population of autologous mononuclear cells comprising CD34+ cells is enriched for cells expressing CD34 cell antigen and CXCR-4 cell antigen by fluorescence activated cell sorting (FACS). In some embodiments, the isolated population of autologous mononuclear cells comprising CD34+ cells are enriched/selected by positive or negative immunoseparation techniques. In some embodiments, isolation and/or purification of hematopoietic stem cells from the isolated population of autologous mononuclear cells comprising CD34+ cells is based on cell fractionation methods based on size and cell density, efflux of metabolic dyes, or resistance to cytotoxic agents. In one embodiment, for example, the isolated population of autologous mononuclear cells comprising CD34+ cells in is enriched for CD34+ cells/selected using a monoclonal anti-CD34 antibody and an immunomagnetic separation technique.

The isolated CD34+ cells may be identified, quantified and characterized by techniques known in the art. For example, in some embodiments, the percentage of CD34+ cells in the isolated population of autologous mononuclear cells comprising CD34+ cells and in the chemotactic hematopoietic stem cell product can be determined by FACS analysis. According to another embodiment, CD34 protein expression is quantified by Western blot. The term "Western blot" refers to a method for identifying proteins in a complex mixture; proteins are separated electrophoretically in a gel medium; transferred from the gel to a protein binding sheet or membrane; and the sheet or membrane containing the separated proteins exposed to specific antibodies which bind to, locate, and enable visualization of protein(s) of interest. For example, monoclonal anti-CD34 antibody can be used to detect CD34 protein adhered to a membrane in situ.

According to another embodiment, the expression of CD34 mRNA and DNA in the isolated CD34+ cells may be quantified. The term "Northern blot" as used herein refers to a technique in which RNA from a specimen is separated into its component parts on a gel by electrophoresis and transferred to a specifically modified paper support so that the mRNA is fixed in its electrophoretic positions. CD34 related sequences are identified using probes comprising a reporter molecule, such as, without limitation, a radioactive label. According to another embodiment, the level of CD34 and/or CXCR-4 expression is/are determined by quantitative or semi-quantitative PCR or real time PCR ("RT-PCR") techniques. The abbreviation "PCR" refers to polymerase chain reaction, which is a technique for amplifying the quantity of DNA, thus making the DNA easier to isolate, clone and sequence. See, e.g., U.S. Pat. Nos. 5,656,493, 5,333,675, 5,234,824, and 5,187,083, each of which is incorporated herein by reference. Real-time PCR is a method of simultaneous DNA quantification and amplification, whereby DNA is specifically amplified by polymerase chain reaction (PCR), and after each round of amplification, the DNA is quantified.

According to another embodiment, the isolated CD34+ hematopoietic stem cells of the chemotactic hematopoietic stem cell product of the described invention contain a subpopulation of CD34+ cells expressing CXCR-4 and having CXCR-4 mediated chemotactic activity. According to another embodiment, the hematopoietic stem cell product of the described invention comprises a minimum number of isolated CD34+ hematopoietic stem cells such that a subpopulation of at least $0.5 \times 10^6$ CD34+ cells expressing CXCR-4 and having CXCR-4 mediated chemotactic activity is present. According to another embodiment, at least about 2% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 3% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 4% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 5% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 6% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 7% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 8% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 9% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 10% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 11% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 12% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 13% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 14% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 15% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 16% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 17% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 18% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 19% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 20% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 21% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 22% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 23% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 24% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 25% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 26% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 27% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 28% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 29% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 30% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 31% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 32% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 33% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least about 34% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product.

According to another embodiment, at least about 2% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 3% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 4% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 5% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 6% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 7% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 8% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 9% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 10% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 11% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 12% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 13% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 14% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 15% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 16% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 17% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 18% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 19% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 20% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 21% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 22% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 23% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 24% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 25% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 26% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 27% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 28% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 29% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 30% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 31% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 32% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 33% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells. According to another embodiment, at least about 34% of the CXCR-4 mediated chemotactic activity of the isolated CD34+ cells containing a subpopulation of potent CD34+ cells expressing CXCR-4 and having chemotactic activity is retained for at least 48 hours following acquisition of the enriched population of CD34+ cells.

According to another embodiment, at least about 2% of the CXCR-4 mediated chemotactic activity of the isolated $CD34^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 3% of the CXCR-4 mediated chemotactic activity of the isolated $CD34^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 4% of the CXCR-4 mediated chemotactic activity of the isolated $CD34^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 5% of the CXCR-4 mediated chemotactic activity of the isolated $CD34^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 6% of the CXCR-4 mediated chemotactic activity of the isolated $CD34^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 7% of the CXCR-4 mediated chemotactic activity of the isolated $CD34^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 8% of the CXCR-4 mediated chemotactic activity of the isolated $CD34^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 9% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 10% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 11% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 12% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 13% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 14% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 15% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 16% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 17% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 18% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 19% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 20% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 21% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 22% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 23% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 24% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 25% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 26% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 27% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 28% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 29% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 30% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 31% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 32% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 33% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product. According to another embodiment, at least about 34% of the CXCR-4 mediated chemotactic activity of the isolated CD34$^+$ cells containing a subpopulation of potent CD34+ cells expressing CXCR-4 and having chemotactic activity is retained for at least 72 hours following acquisition of the chemotactic hematopoietic stem cell product.

According to another embodiment, at least an average of about 17% of the CXCR-4 mediated chemotactic activity of the isolated CD34+ cells containing a subpopulation of potent CD34+ cells expressing CXCR-4 and having chemotactic activity is retained for at least 24 hours following acquisition of the chemotactic hematopoietic stem cell product. According to another embodiment, at least an average of about 17% of the CXCR-4 mediated chemotactic activity of the isolated CD34+ cells containing a subpopulation of potent CD34+ cells expressing CXCR-4 and having chemotactic activity is retained for at least 48 hours following acquisition of the chemotactic hematopoietic stem cell product. According to another embodiment, at least an average of about 17% of the CXCR-4 mediated chemotactic activity of the isolated CD34+ cells containing a subpopulation of potent CD34+ cells expressing CXCR-4 and having chemotactic activity is retained for at least 72 hours following acquisition of the chemotactic hematopoietic stem cell product. According to another embodiment, the isolated CD34+ cells containing a subpopulation of potent CD34+ cells expressing CXCR-4 and having chemotactic activity in the chemotactic hematopoietic cell product retain at least about 2% of the CXCR-4 mediated chemotactic activity for at least 72 hours following acquisition of the chemotactic hematopoietic stem cell product.

According to another embodiment, the pharmaceutical composition of the invention further comprises serum at a concentration of at least 10% expressed as ml/100 cc final volume of the progressive myocardial injury-preventing composition. According to another embodiment, the pharmaceutical composition of the invention further comprises serum at a concentration of at least 11% expressed as ml/100 cc final volume of the progressive myocardial injury-preventing composition. According to another embodiment, the pharmaceutical composition of the invention further comprises serum at a concentration of at least 12% expressed as ml/100 cc final volume of the progressive myocardial injury-preventing composition. According to another embodiment, the pharmaceutical composition of the invention further comprises serum at a concentration of at least 13% expressed as ml/100 cc final volume of the progressive myocardial injury-preventing composition. According to another embodiment, the pharmaceutical composition of the invention further comprises serum at a concentration of at least 14% expressed as ml/100 cc final volume of the progressive myocardial injury-preventing composition. According to another embodiment, the pharmaceutical composition of the invention further comprises serum at a concentration of at least 15% expressed as ml/100 cc final volume of the progressive myocardial injury-preventing composition. According to another embodiment, the pharmaceutical composition of the invention further comprises serum at a concentration of at least 16% expressed as ml/100 cc final volume of the progressive myocardial injury-preventing composition. According to another embodiment, the pharmaceutical composition of the invention further comprises serum at a concentration of at least 17% expressed as ml/100 cc final volume of the progressive myocardial injury-preventing composition. According to another embodiment, the pharmaceutical composition of the invention further comprises serum at a concentration of at least 18% expressed as ml/100 cc final volume of the progressive myocardial injury-preventing composition. According to another embodiment, the pharmaceutical composition of the invention further comprises serum at a concentration of at least 19% expressed as ml/100 cc final volume of the progressive myocardial injury-preventing composition. According to another embodiment, the pharmaceutical composition of the invention further comprises serum at a concentration of at least 20% expressed as ml/100 cc final volume of the progressive myocardial injury-preventing composition. According to another embodiment, the minimum concentration of serum present in the progressive myocardial injury-preventing composition is at least about 21% expressed as ml/100 cc final volume of the composition. According to another embodiment, the minimum concentration of serum present in the progressive myocardial injury-preventing composition is at least about 22% expressed as ml/100 cc final volume of the composition. According to another embodiment, the minimum concentration of serum present in the progressive myocardial injury-preventing composition is at least about 23% expressed as ml/100 cc final volume of the composition. According to another embodiment, the minimum concentration of serum present in the progressive myocardial injury-preventing composition is at least about 24% expressed as ml/100 cc final volume of the composition. According to another embodiment, the minimum concentration of serum present in the progressive myocardial injury-preventing composition is at least about 25% expressed as ml/100 cc final volume of the composition. According to another embodiment, the minimum concentration of serum present in the progressive myocardial injury-preventing composition is at least about 26% expressed as ml/100 cc final volume of the composition. According to another embodiment, the minimum concentration of serum present in the progressive myocardial injury-preventing composition is at least about 27% expressed as ml/100 cc final volume of the composition. According to another embodiment, the minimum concentration of serum present in the progressive myocardial injury-preventing composition is at least about 28% expressed as ml/100 cc final volume of the composition. According to another embodiment, the minimum concentration of serum present in the progressive myocardial injury-preventing composition is at least about 29% expressed as ml/100 cc final volume of the composition. According to another embodiment, the minimum concentration of serum present in the progressive myocardial injury-preventing composition is at least about 30% expressed as ml/100 cc final volume of the composition. According to another embodiment, the minimum concentration of serum present in the progressive myocardial injury-preventing composition is at least about 31% expressed as ml/100 cc final volume of the composition.

According to another embodiment, the minimum concentration of serum present in the progressive myocardial injury-preventing composition is at least about 32% expressed as ml/100 cc final volume of the composition. According to another embodiment, the minimum concentration of serum present in the progressive myocardial injury-preventing composition is at least about 33% expressed as ml/100 cc final volume of the composition. According to another embodiment, the minimum concentration of serum present in the progressive myocardial injury-preventing composition is at least about 34% expressed as ml/100 cc final volume of the composition. According to another embodiment, the minimum concentration of serum present in the progressive myocardial injury-preventing composition is at least about 35% expressed as ml/100 cc final volume of the composition. According to another embodiment, the minimum concentration of serum present in the progressive myocardial injury-preventing composition is at least about 36% expressed as ml/100 cc final volume of the composition. According to another embodiment, the minimum concentration of serum present in the progressive myocardial injury-preventing composition is at least about 37% expressed as ml/100 cc final volume of the composition. According to another embodiment, the minimum concentration of serum present in the progressive myocardial injury-preventing composition is at least about 38% expressed as ml/100 cc final volume of the composition. According to another embodiment, the minimum concentration of serum present in the progressive myocardial injury-preventing composition is at least about 39% expressed as ml/100 cc final volume of the composition. According to another embodiment, the minimum concentration of serum present in the progressive myocardial injury-preventing composition is at least about 40% expressed as ml/100 cc final volume of the composition. According to another embodiment, the minimum concentration of serum present in the progressive myocardial injury-preventing composition is at least about 41% expressed as ml/100 cc final volume of the composition. According to another embodiment, the minimum concentration of serum present in the progressive myocardial injury-preventing composition is at least about 42% expressed as ml/100 cc final volume of the composition. According to another embodiment, the minimum concentration of serum present in the progressive myocardial injury-preventing composition is at least about 43% expressed as ml/100 cc final volume of the composition. According to another embodiment, the minimum concentration of serum present in the progressive myocardial injury-preventing composition is at least about 44% expressed as ml/100 cc final volume of the composition. According to another embodiment, the minimum concentration of serum present in the progressive myocardial injury-preventing composition is at least about 45% expressed as ml/100 cc final volume of the composition. According to another embodiment, the minimum concentration of serum present in the progressive myocardial injury-preventing composition is at least about 46% expressed as ml/100 cc final volume of the composition. According to another embodiment, the minimum concentration of serum present in the progressive myocardial injury-preventing composition is at least about 47% expressed as ml/100 cc final volume of the composition. According to another embodiment, the minimum concentration of serum present in the progressive myocardial injury-preventing composition is at least about 48% expressed as ml/100 cc final volume of the composition. According to another embodiment, the minimum concentration of serum present in the progressive myocardial injury-preventing composition is at least about 49% expressed as ml/100 cc final volume of the composition. According to another embodiment, the minimum concentration of serum present in the progressive myocardial injury-preventing composition is at least about 50% expressed as ml/100 cc final volume of the composition. According to another embodiment, the minimum concentration of serum present in the progressive myocardial injury-preventing composition is at least about 51% expressed as ml/100 cc final volume of the composition. According to another embodiment, the minimum concentration of serum present in the progressive myocardial injury-preventing composition is at least about 52% expressed as ml/100 cc final volume of the composition. According to another embodiment, the minimum concentration of serum present in the progressive myocardial injury-preventing composition is at least about 53% expressed as ml/100 cc final volume of the composition. According to another embodiment, the minimum concentration of serum present in the progressive myocardial injury-preventing composition is at least about 54% expressed as ml/100 cc final volume of the composition. According to another embodiment, the minimum concentration of serum present in the progressive myocardial injury-preventing composition is at least about 55% expressed as ml/100 cc final volume of the composition. According to another embodiment, the minimum concentration of serum present in the progressive myocardial injury-preventing composition is at least about 56% expressed as ml/100 cc final volume of the composition. According to another embodiment, the minimum concentration of serum present in the progressive myocardial injury-preventing composition is at least about 57% expressed as ml/100 cc final volume of the composition. According to another embodiment, the minimum concentration of serum present in the progressive myocardial injury-preventing composition is at least about 58% expressed as ml/100 cc final volume of the composition. According to another embodiment, the minimum concentration of serum present in the progressive myocardial injury-preventing composition is at least about 59% expressed as ml/100 cc final volume of the composition. According to another embodiment, the minimum concentration of serum present in the progressive myocardial injury-preventing composition is at least about 60% expressed as ml/100 cc final volume of the composition. According to another embodiment, the minimum concentration of serum present in the progressive myocardial injury-preventing composition is at least about 61% expressed as ml/100 cc final volume of the composition. According to another embodiment, the minimum concentration of serum present in the progressive myocardial injury-preventing composition is at least about 62% expressed as ml/100 cc final volume of the composition. According to another embodiment, the minimum concentration of serum present in the progressive myocardial injury-preventing composition is at least about 63% expressed as ml/100 cc final volume of the composition. According to another embodiment, the minimum concentration of serum present in the progressive myocardial injury-preventing composition is at least about 64% expressed as ml/100 cc final volume of the composition. According to another embodiment, the minimum concentration of serum present in the progressive myocardial injury-preventing composition is at least about 65% expressed as ml/100 cc final volume of the composition. According to another embodiment, the minimum concentration of serum present in the progressive myocardial injury-preventing composition is at least about 66% expressed as ml/100 cc final volume of the composition. According to another embodiment, the minimum concentration of serum present in the progressive myocardial injury-preventing composition is at least about 67% expressed as ml/100 cc final volume of the composition. According to another embodiment, the minimum concentration of serum present in the progressive myocardial injury-preventing composition is at least about 68% expressed as ml/100 cc final volume of the composition. According to another embodiment, the minimum concentration of serum present in the progressive myocardial injury-preventing composition is at least about 69% expressed as ml/100 cc final volume of the composition. According to another embodiment, the minimum concentration of serum present in the composition is at least about 70% expressed as ml/100 cc final volume of the composition.

According to another embodiment, the serum is autologous. According to another embodiment, the serum is a synthetic or recombinant serum.

According to another embodiment, the maximum concentration of serum present in the progressive myocardial injury-preventing composition of the described invention is about 70% expressed as ml/100 cc final volume of the composition. According to another embodiment, the maximum concentration of serum present in the progressive myocardial injury-preventing composition of the described invention is about 69% expressed as ml/100 cc final volume of the composition. According to another embodiment, the maximum concentration of serum present in the progressive myocardial injury-preventing composition of the described invention is about 68% expressed as ml/100 cc final volume of the composition. According to another embodiment, the maximum concentration of serum present in the progressive myocardial injury-preventing composition of the described invention is about 67% expressed as ml/100 cc final volume of the composition. According to another embodiment, the maximum concentration of serum present in the progressive myocardial injury-preventing composition of the described invention is about 66% expressed as ml/100 cc final volume of the composition. According to another embodiment, the maximum concentration of serum present in the progressive myocardial injury-preventing composition of the described invention is about 65% expressed as ml/100 cc final volume of the composition. According to another embodiment, the maximum concentration of serum present in the progressive myocardial injury-preventing composition of the described invention is about 64% expressed as ml/100 cc final volume of the composition. According to another embodiment, the maximum concentration of serum present in the progressive myocardial injury-preventing composition of the described invention is about 63% expressed as ml/100 cc final volume of the composition. According to another embodiment, the maximum concentration of serum present in the progressive myocardial injury-preventing composition of the described invention is about 62% expressed as ml/100 cc final volume of the composition. According to another embodiment, the maximum concentration of serum present in the progressive myocardial injury-preventing composition of the described invention is about 61% expressed as ml/100 cc final volume of the composition. According to another embodiment, the maximum concentration of serum present in the progressive myocardial injury-preventing composition of the described invention is about 60% expressed as ml/100 cc final volume of the composition. According to another embodiment, the maximum concentration of serum present in the progressive myocardial injury-preventing composition of the described invention is about 59% expressed as ml/100 cc final volume of the composition. According to another embodiment, the maximum concentration of serum present in the progressive myocardial injury-preventing composition of the described invention is about 58% expressed as ml/100 cc final volume of the composition. According to another embodiment, the maximum concentration of serum present in the progressive myocardial injury-preventing composition of the described invention is about 57% expressed as ml/100 cc final volume of the composition. According to another embodiment, the maximum concentration of serum present in the progressive myocardial injury-preventing composition of the described invention is about 56% expressed as ml/100 cc final volume of the composition. According to another embodiment, the maximum concentration of serum present in the progressive myocardial injury-preventing composition of the described invention is about 55% expressed as ml/100 cc final volume of the composition. According to another embodiment, the maximum concentration of serum present in the progressive myocardial injury-preventing composition of the described invention is about 54% expressed as ml/100 cc final volume of the composition. According to another embodiment, the maximum concentration of serum present in the progressive myocardial injury-preventing composition of the described invention is about 53% expressed as ml/100 cc final volume of the composition. According to another embodiment, the maximum concentration of serum present in the progressive myocardial injury-preventing composition of the described invention is about 52% expressed as ml/100 cc final volume of the composition. According to another embodiment, the maximum concentration of serum present in the progressive myocardial injury-preventing composition of the described invention is about 51% expressed as ml/100 cc final volume of the composition. According to another embodiment, the maximum concentration of serum present in the progressive myocardial injury-preventing composition of the described invention is about 50% expressed as ml/100 cc final volume of the composition.

According to another embodiment, the maximum concentration of serum present in the progressive myocardial injury-preventing composition of the described invention is about 49% expressed as ml/100 cc final volume of the composition. According to another embodiment, the maximum concentration of serum present in the progressive myocardial injury-preventing composition of the described invention is about 48% expressed as ml/100 cc final volume of the composition. According to another embodiment, the maximum concentration of serum present in the progressive myocardial injury-preventing composition of the described invention is about 47% expressed as ml/100 cc final volume of the composition. According to another embodiment, the maximum concentration of serum present in the progressive myocardial injury-preventing composition of the described invention is about 46% expressed as ml/100 cc final volume of the composition. According to another embodiment, the maximum concentration of serum present in the progressive myocardial injury-preventing composition of the described invention is about 45% expressed as ml/100 cc final volume of the composition. According to another embodiment, the maximum concentration of serum present in the progressive myocardial injury-preventing composition of the described invention is about 44% expressed as ml/100 cc final volume of the composition. According to another embodiment, the maximum concentration of serum present in the progressive myocardial injury-preventing composition of the described invention is about 43% expressed as ml/100 cc final volume of the composition. According to another embodiment, the maximum concentration of serum present in the progressive myocardial injury-preventing composition of the described invention is about 42% expressed as ml/100 cc final volume of the composition. According to another embodiment, the maximum concentration of serum present in the progressive myocardial injury-preventing composition of the described invention is about 41% expressed as ml/100 cc final volume of the composition. According to another embodiment, the maximum concentration of serum present in the progressive myocardial injury-preventing composition of the described invention is about 40% expressed as ml/100 cc final volume of the composition.

According to another embodiment, the maximum concentration of serum present in the progressive myocardial injury-preventing composition of the described invention is about 39% expressed as ml/100 cc final volume of the composition. According to another embodiment, the maximum concentration of serum present in the progressive myocardial injury-preventing composition of the described invention is about 38% expressed as ml/100 cc final volume of the composition. According to another embodiment, the maximum concentration of serum present in the progressive myocardial injury-preventing composition of the described invention is about 37% expressed as ml/100 cc final volume of the composition. According to another embodiment, the maximum concentration of serum present in the progressive myocardial injury-preventing composition of the described invention is about 36% expressed as ml/100 cc final volume of the composition. According to another embodiment, the maximum concentration of serum present in the progressive myocardial injury-preventing composition of the described invention is about 35% expressed as ml/100 cc final volume of the composition. According to another embodiment, the maximum concentration of serum present in the progressive myocardial injury-preventing composition of the described invention is about 34% expressed as ml/100 cc final volume of the composition. According to another embodiment, the maximum concentration of serum present in the progressive myocardial injury-preventing composition of the described invention is about 33% expressed as ml/100 cc final volume of the composition. According to another embodiment, the maximum concentration of serum present in the progressive myocardial injury-preventing composition of the described invention is about 32% expressed as ml/100 cc final volume of the composition. According to another embodiment, the maximum concentration of serum present in the progressive myocardial injury-preventing composition of the described invention is about 31% expressed as ml/100 cc final volume of the composition. According to another embodiment, the maximum concentration of serum present in the progressive myocardial injury-preventing composition of the described invention is about 30% expressed as ml/100 cc final volume of the composition. According to another embodiment, the maximum concentration of serum present in the progressive myocardial injury-preventing composition of the described invention is about 29% expressed as ml/100 cc final volume of the composition. According to another embodiment, the maximum concentration of serum present in the progressive myocardial injury-preventing composition of the described invention is about 28% expressed as ml/100 cc final volume of the composition. According to another embodiment, the maximum concentration of serum present in the progressive myocardial injury-preventing composition of the described invention is about 27% expressed as ml/100 cc final volume of the composition. According to another embodiment, the maximum concentration of serum present in the progressive myocardial injury-preventing composition of the described invention is about 26% expressed as ml/100 cc final volume of the composition. According to another embodiment, the maximum concentration of serum present in the progressive myocardial injury-preventing composition of the described invention is about. 25% expressed as ml/100 cc final volume of the composition. According to another embodiment, the maximum concentration of serum present in the progressive myocardial injury-preventing composition of the described invention is about 24% expressed as ml/100 cc final volume of the composition. According to another embodiment, the maximum concentration of serum present in the progressive myocardial injury-preventing composition of the described invention is about 23% expressed as ml/100 cc final volume of the composition. According to another embodiment, the maximum concentration of serum present in the progressive myocardial injury-preventing composition of the described invention is about 22% expressed as ml/100 cc final volume of the composition. According to another embodiment, the maximum concentration of serum present in the progressive myocardial injury-preventing composition of the described invention is about 21% expressed as ml/100 cc final volume of the composition. According to another embodiment, the maximum concentration of serum present in the progressive myocardial injury-preventing composition of the described invention is about 20% expressed as ml/100 cc final volume of the composition. According to another embodiment, the maximum concentration of serum present in the progressive myocardial injury-preventing composition of the described invention is about 15% expressed as ml/100 cc final volume of the composition. According to another embodiment, the maximum concentration of serum present in the progressive myocardial injury-preventing composition of the described invention is about 10% expressed as ml/100 cc final volume of the composition.

In some embodiments, the progressive myocardial injury-preventing composition may be formulated with an excipient, carrier or vehicle including, but not limited to, a solvent. The terms "excipient", "carrier", or "vehicle" as used herein refers to carrier materials suitable for formulation and administration of the chemotactic hematopoietic stem cell product described herein. Carriers and vehicles useful herein include any such materials know in the art which are nontoxic and do not interact with other components. As used herein the phrase "pharmaceutically acceptable carrier" refers to any substantially non-toxic carrier useable for formulation and administration of the composition of the described invention in which the chemotactic hematopoietic stem cell product of the described invention will remain stable and bioavailable.

The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition. For example, the pharmaceutically acceptable carrier may be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions of the described invention include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like. Such carrier solutions also can contain buffers, diluents and other suitable additives. The term "buffer" as used herein refers to a solution or liquid whose chemical makeup neutralizes acids or bases without a significant change in pH. Examples of buffers envisioned by the described invention include, but are not limited to, Dulbecco's phosphate buffered saline (PBS), Ringer's solution, 5% dextrose in water (D5W), and normal/physiologic saline (0.9% NaCl). In some embodiments, the infusion solution is isotonic to subject tissues. In some embodiments, the infusion solution is hypertonic to subject tissues. Compositions of the described invention that are for parenteral administration may include pharmaceutically acceptable carriers such as sterile aqueous solutions, non-aqueous solutions in common solvents such as alcohols, or solutions in a liquid oil base.

In some embodiments, the carrier of the progressive myocardial injury-preventing composition of the described invention may include a release agent such as a sustained release or delayed release carrier. In such embodiments, the carrier may be any material capable of sustained or delayed release of the active to provide a more efficient administration, e.g., resulting in less frequent and/or decreased dosage of the composition, improve ease of handling, and extend or delay effects on diseases, disorders, conditions, syndromes, and the like, being treated, prevented or promoted. Non-limiting examples of such carriers include liposomes, microsponges, microspheres, or microcapsules of natural and synthetic polymers and the like. Liposomes may be formed from a variety of phospholipids such as cholesterol, stearylamines or phosphatidylcholines.

The progressive myocardial injury-preventing compositions of the described invention may be administered parenterally in the form of a sterile injectable aqueous or oleaginous suspension. The term "parenteral" or "parenterally" as used herein refers to introduction into the body by way of an injection (i.e., administration by injection), including, but not limited to, infusion techniques. In some embodiments, the progressive myocardial injury-preventing composition of the described invention comprising a chemotactic hematopoietic stem cell product is delivered to the subject by means of a balloon catheter adapted for delivery of the fluid compositions (i.e., compositions capable of flow) into a selected anatomical structure.

The sterile progressive myocardial injury-preventing composition of the described invention may be a sterile solution or suspension in a nontoxic parenterally acceptable diluent or solvent. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it does not rapidly settle out. In everyday life, the most common suspensions are those of solids in liquid water. Among the acceptable vehicles and solvents that may be employed are water, Ringer's solution, and isotonic sodium chloride (saline) solution. In some embodiments, hypertonic solutions are employed. In addition, sterile, fixed oils conventionally are employed as a solvent or suspending medium. For parenteral application, suitable vehicles consist of solutions, e.g., oily or aqueous solutions, as well as suspensions, emulsions, or implants. Aqueous suspensions may contain substances, which increase the viscosity of the suspension and include, for example, sodium carboxymethyl cellulose, sorbitol and/or dextran.

Additional progressive myocardial injury-preventing compositions of the described invention readily may be prepared using technology, which is known in the art, such as described in Remington's Pharmaceutical Sciences, 18th or 19th editions, published by the Mack Publishing Company of Easton, Pa., which is incorporated herein by reference.

As used herein the terms "therapeutically effective", "myocardial injury preventing amount", "vascular insufficiency repairing amount", "adverse consequence preventing amount", "adverse consequence-reversing amount", or "pharmaceutically effective amount" refer to the amount of the compositions of the invention that result in a therapeutic or beneficial effect following its administration to a subject. The vascular insufficiency repairing, myocardial injury repairing, therapeutic, adverse consequence reversing or pharmaceutical effect may be curing, minimizing, preventing or ameliorating a disease or disorder, or may have any other vascular insufficiency-repairing, myocardial injury-repairing, adverse consequence reversing, or pharmaceutical beneficial effect. The concentration of the substance is selected so as to exert its vascular insufficiency-repairing, myocardial injury-repairing, adverse consequence reversing, therapeutic, or pharmaceutical effect, but low enough to avoid significant side effects within the scope and sound judgment of the physician. The effective amount of the composition may vary with the age and physical condition of the biological subject being treated, the severity of the condition, the duration of the treatment, the nature of concurrent therapy, the timing of the infusion, the specific compound, composition or other active ingredient employed, the particular carrier utilized, and like factors.

A skilled artisan may determine a pharmaceutically effective amount of the inventive compositions by determining the dose in a dosage unit (meaning unit of use) that elicits a given intensity of effect, hereinafter referred to as the "unit dose." The term "dose-intensity relationship" refers to the manner in which the intensity of effect in an individual recipient relates to dose. The intensity of effect generally designated is 50% of maximum intensity. The corresponding dose is called the 50% effective dose or individual ED50. The use of the term "individual" distinguishes the ED50 based on the intensity of effect as used herein from the median effective dose, also abbreviated ED50, determined from frequency of response data in a population. "Efficacy" as used herein refers to the property of the compositions of the described invention to achieve the desired response, and "maximum efficacy" refers to the maximum achievable effect. The amount of the chemotactic hematopoietic stem cell product in the pharmaceutical compositions of the described invention that will be effective in the treatment of a particular disorder or condition will depend on the nature of the disorder or condition, and may be determined by standard clinical techniques. (See, for example, Goodman and Gilman's THE PHARMACOLOGICAL BASIS OF THERAPEUTICS, Joel G. Harman, Lee E. Limbird, Eds.; McGraw Hill, New York, 2001; THE PHYSICIAN'S DESK REFERENCE, Medical Economics Company, Inc., Oradell, N.J., 1995; and DRUG FACTS AND COMPARISONS, FACTS AND COMPARISONS, INC., St. Louis, Mo., 1993), each of which is incorporated by reference herein. The precise dose to be employed in the formulations of the described invention also will depend on the route of administration and the seriousness of the disease or disorder, and should be decided according to the judgment of the practitioner and each subject's circumstances.

According to another embodiment, the pharmaceutical compositions according to the described invention contain a minimum number of CD34+ hematopoietic stem cells having a subpopulation of at least $0.5 \times 10^6$ CD34+ cells expressing CXCR-4 and having CXCR-4 mediated chemotactic activity per dosage unit for parenteral administration at the physician's discretion. According to another embodiment, it is envisioned that subjects can benefit from multiple administrations of the pharmaceutical compositions according to the described invention comprising a minimum number of CD34+ hematopoietic stem cells having a subpopulation of at least $0.5 \times 10^6$ CD34+ cells expressing CXCR-4 and having CXCR-4 mediated chemotactic activity.

In another aspect of the described invention, the progressive myocardial injury-preventing pharmaceutical compositions of the described invention may further include one or more compatible active ingredients, which are aimed at providing the progressive myocardial injury-preventing composition with another pharmaceutical effect in addition to that provided by the sterile chemotactic hematopoietic stem cell product of the described invention. "Compatible" as used herein means that the active ingredients of such a composition are capable of being combined with each other in such a manner so that there is no interaction that would substantially reduce the efficacy of each active ingredient or the composition under ordinary use conditions. In some embodiments, the combination therapy comprises administering to a subject in need thereof a progressive myocardial injury-preventing pharmaceutical composition comprising a sterile chemotactic hematopoietic stem cell product of the described invention combined with an agent selected from the group consisting of an angiotensin converting enzyme (ACE) inhibitor, a beta-blocker, a diuretic, an anti-arrhythmic agent, a hematopoietic stem cell mobilizing agent, a tyrosine kinase receptor agonist, an anti-anginal agent, a vasoactive agent or inotrope, an anticoagulant agent, a fibrinolytic agent, and a hypercholesterolemic agent. According to some embodiments, the tyrosine kinase receptor agonist is neuregulin 1. According to some embodiments, the neuregulin 1 is a recombinant protein. According to some embodiments, the hematopoietic stem cell mobilizing agent is a colony stimulating factor. According to some such embodiments, the hematopoietic stem cell mobilizing agent comprises G-CSF, GM-CSF, or a pharmaceutically acceptable analog or derivative thereof. According to some embodiments, the hematopoietic stem cell mobilizing agent is a recombinant analog or derivative of a colony stimulating factor. According to some embodiments, the hematopoietic stem cell mobilizing agent is filgrastim.

In some embodiments, the composition of the described invention further comprises about 0.5% to about 5% albumin. In some embodiments, the minimum amount of albumin is about 0.5% expressed as ml/100 cc volume of the composition. In some embodiments, the minimum amount of albumin is about 0.75% expressed as ml/100 cc volume of the composition. In some embodiments, the minimum amount of albumin is about 1.0% expressed as ml/100 cc volume of the composition. In some embodiments, the minimum amount of albumin is about 1.25% expressed as ml/100 cc volume of the composition. In some embodiments, the minimum amount of albumin is about 1.5% expressed as ml/100 cc volume of the composition. In some embodiments, the minimum amount of albumin is about 1.75% expressed as ml/100 cc volume of the composition. In some embodiments, the minimum amount of albumin is about 2.0% expressed as ml/100 cc volume of the composition. In some embodiments, the minimum amount of albumin is about 2.5% expressed as ml/100 cc volume of the composition. In some embodiments, the minimum amount of albumin is about 2.75% expressed as ml/100 cc volume of the composition. In some embodiments, the minimum amount of albumin is about 3.0% expressed as ml/100 cc volume of the composition. In some embodiments, the minimum amount of albumin is about 3.5% expressed as ml/100 cc volume of the composition. In some embodiments, the minimum amount of albumin is about 4.0% expressed as ml/100 cc volume of the composition. In some embodiments, the minimum amount of albumin is about 4.5% expressed as ml/100 cc volume of the composition. In some embodiments, the minimum amount of albumin is about 5.0% expressed as ml/100 cc volume of the composition.

In some embodiments, the maximum amount of albumin in the compositions of the described invention is about 5.0% expressed as ml/100 cc volume of the composition. In some embodiments, the maximum amount of albumin in the compositions of the described invention is about 4.75% expressed as ml/100 cc volume of the composition. In some embodiments, the maximum amount of albumin in the compositions of the described invention is about 4.5% expressed as ml/100 cc volume of the composition. In some embodiments, the maximum amount of albumin in the compositions of the described invention is about 4.0% expressed as ml/100 cc volume of the composition. In some embodiments, the maximum amount of albumin in the compositions of the described invention is about 4.25% expressed as ml/100 cc volume of the composition. In some embodiments, the maximum amount of albumin in the compositions of the described invention is about 4.0% expressed as ml/100 cc volume of the composition. In some embodiments, the maximum amount of albumin in the compositions of the described invention is about 3.75% expressed as ml/100 cc volume of the composition. In some embodiments, the maximum amount of albumin in the compositions of the described invention is about 3.5% expressed as ml/100 cc volume of the composition. In some embodiments, the maximum amount of albumin in the compositions of the described invention is about 3.25% expressed as ml/100 cc volume of the composition. In some embodiments, the maximum amount of albumin in the compositions of the described invention is about 3.0% expressed as ml/100 cc volume of the composition. In some embodiments, the maximum amount of albumin in the compositions of the described invention is about 2.75% expressed as ml/100 cc volume of the composition. In some embodiments, the maximum amount of albumin in the compositions of the described invention is about 2.0% expressed as ml/100 cc volume of the composition. In some embodiments, the maximum amount of albumin in the compositions of the described invention is about 1.75% expressed as ml/100 cc volume of the composition. In some embodiments, the maximum amount of albumin in the compositions of the described invention is about 1.5% expressed as ml/100 cc volume of the composition. In some embodiments, the maximum amount of albumin in the compositions of the described invention is about 1.25% expressed as ml/100 cc volume of the composition. In some embodiments, the maximum amount of albumin in the compositions of the described invention is about 1% expressed as ml/100 cc volume of the composition. In some embodiments, the albumin is human albumin. In some embodiments the albumin is recombinant human albumin.

Methods of the Described Invention

In another aspect, the described invention provides a method of preparing a progressive myocardial injury-preventing pharmaceutical composition comprising a sterile chemotactic hematopoietic stem cell product for treating a subject in need thereof. The method comprises the steps of (1) acquiring a sterile nonexpanded, isolated population of autologous mononuclear cells comprising CD34+ cells, which further contain a subpopulation of potent CD34+/CXCR-4+ cells that have CXCR-4-mediated chemotactic activity from the subject under sterile conditions by a chemotactic cell acquisition process;

(2) optionally freezing at least one aliquot of the nonexpanded, isolated population of autologous mononuclear cells of step (1) at −86° C. and cryostoring the at least one aliquot in the vapor phase of a liquid nitrogen freezer; and thawing the at least one aliquot of step (2) when needed;

(3) sterilely purifying the CD34+ cells from the sterile nonexpanded, isolated population of autologous mononuclear cells comprising CD34+ cells of (1) or (2) so as to yield a chemotactic hematopoietic stem cell product comprising the nonexpanded, isolated population of autologous mononuclear cells enriched for CD34+ cells, which further contain a subpopulation of potent CD34+ cells that express CXCR-4 and that have CXCR-4-mediated chemotactic activity;

(4) sterilely formulating the sterile chemotactic hematopoietic stem cell product to form a sterile pharmaceutical composition;

(5) confirming sterility of the pharmaceutical composition;

(6) releasing the sterile pharmaceutical composition as eligible for infusion into the subject;

(7) loading a therapeutically effective amount of the pharmaceutical composition into a chemotactic hematopoietic stem cell product delivery apparatus; and (8) optionally transporting the delivery apparatus containing the therapeutically effective amount of the sterile pharmaceutical composition comprising the sterile chemotactic hematopoietic stem cell product to a cardiac catheterization facility for infusion into the subject.

According to some embodiments, the nonexpanded, isolated population of autologous mononuclear cells can be acquired from the subject at any time. According to some embodiments, the nonexpanded, isolated population of autologous mononuclear cells is acquired early after an AMI. According to some such embodiments, the nonexpanded, isolated population of autologous mononuclear cells is acquired 5 days, 6 days, 7 days, 8 days, 9 days, 10 days, 11 days, 12 days, 13 days, 14 days or more after the occurrence of an AMI. According to some embodiments, the nonexpanded, isolated population of autologous mononuclear cells is acquired late after the occurrence of an AMI. According to some such embodiments, the nonexpanded, isolated population of autologous mononuclear cells is acquired at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 60 days, at least 90 days, at least 120 days, at least 150 days, at least 180 days or more after the occurrence of the AMI. According to some embodiments, the nonexpanded, isolated population of autologous mononuclear cells is acquired at least 1 month, at least 2 months, at least 3 months, at least 4 months, at least 5 months, at least 6 months, at least 7 months, at least 8 months, at least 9 months, at least 10 months, at least 11 months, at least 12 months, at least 16 months, at least 24 months, at least 30 months, at least 36 months, at least 42 months, at least 48 months, at least 54 months, at least 60 months, at least 66 months, at least 72 months, at least 78 months, at least 84 months, at least 90 months, at least 96 months, at least 102 months, at least 108 months, at least 114 months, at least 120 months, at least 126 months, at least 132 months, at least 138 months, at least 144 months, at least 150 months, at least 156 months, at least 162 months, at least 168 months, at least 174 months, at least 180 months, at least 186 months, at least 192 months, at least 198 months, at least 204 months, at least 210 months, at least 216 months, at least 222 months, at least 228 months, at least 234 months, at least 240 months or more after occurrence of an AMT. According to some embodiments, the nonexpanded, isolated population of autologous mononuclear cells is acquired at least at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI.

According to one embodiment, step (3) is initiated within about 12 hours to about 24 hours of completion of acquiring step (1). According to some embodiments, releasing step (6) proceeds only if the sterile formulated cell product is to be infused into the subject within about 48 hours to about 72 hours of completion of acquiring step (1). According to another embodiment, step (3) is initiated within about 12 hours to about 24 hours of completion of acquiring step (1), and releasing step (6) proceeds only if the sterile formulated cell product is to be infused into the subject within about 48 hours to about 72 hours of completion of acquiring step (1).

According to some embodiments, releasing step (6) proceeds only if the sterile formulated cell product is to be infused into the subject within about 48 hours to about 72 hours of thawing of the at least one frozen aliquot of optional step (2). According to another embodiment, step (3) is initiated within about 12 hours to about 24 hours of thawing of the at least one frozen aliquot of optional step (2), and releasing step (6) proceeds only if the sterile formulated cell product is to be infused into the subject within about 48 hours to about 72 hours of thawing of the at least one frozen aliquot of optional step (2).

According to some embodiments, a frozen aliquot of step (2) is thawed at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 60 days, at least 90 days, at least 120 days, at least 150 days, or at least 180 days, from the date the nonexpanded, isolated population of autologous mononuclear cells is acquired from the subject in step (1). According to some embodiments, the frozen aliquot of step (4) is thawed at least 1 month, at least 2 months, at least 3 months, at least 4 months, at least 5 months, at least 6 months, at least 7 months, at least 8 months, at least 9 months, at least 10 months, at least 11 months, at least 12 months, at least 16 months, at least 24 months, at least 30 months, at least 36 months, at least 42 months, at least 48 months, at least 54 months, at least 60 months, at least 66 months, at least 72 months, at least 78 months, at least 84 months, at least 90 months, at least 96 months, at least 102 months, at least 108 months, at least 114 months, at least 120 months, at least 126 months, at least 132 months, at least 138 months, at least 144 months, at least 150 months, at least 156 months, at least 162 months, at least 168 months, at least 174 months, at least 180 months, at least 186 months, at least 192 months, at least 198 months, at least 204 months, at least 210 months, at least 216 months, at least 222 months, at least 228 months, at least 234 months or at least 240 months from the date the nonexpanded, isolated population of autologous mononuclear cells is acquired from the subject in step (1). According to some embodiments, the frozen aliquot of step (2) is thawed at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more from the date the nonexpanded, isolated population of autologous mononuclear cells is acquired from the subject in step (1).

According to such embodiments, the chemotactic hematopoietic stem cell product produced from the frozen aliquot is further characterized as having the following properties for at least 24 hours following thawing when tested in vitro after passage through a catheter: (1) retains at least 10%, at least 20%, at least 30%, at least 40%, at least 50%, at least 60%, at least 70,%, at least 80%, at least 90%, or 100% of the CXCR-4-mediated activity of the of the subpopulation of potent CD34+/CXCR-4+ cells that have CXCR-4-mediated chemotactic activity; (2) at least 70% of the cells are CD34+ cells; (3) is at least 70% viable; and (4) is able to form hematopoietic colonies in vitro.

According to another embodiment, step (5), i.e., the step of assessing sterility of the pharmaceutical composition, further comprises the steps of (i) centrifuging the sterile chemotactic hematopoietic stem cell product comprising potent CD34+/CXCR-4+ cells to form a cell pellet and a supernatant, the cell pellet comprising the potent CD34+/CXCR-4+ cells; (ii) sterilely removing the supernatant without disturbing the cell pellet; and (iii) analyzing whether the supernatant is contaminated by a microbe thereby determining the sterility of the cell pellet.

According to one embodiment, in step (1), the chemotactic cell acquisition process is a mini-bone marrow harvest technique used to acquire the nonexpanded isolated population of autologous mononuclear cells comprising potent CD34+/CXCR-4+ cells from the bone marrow of the subject under sterile conditions. For the bone marrow harvest technique, step (1) of the method further comprises the steps: (i) preloading harvesting syringes with heparin prior to harvesting bone marrow from a subject; (ii) aspirating the bone marrow from a left posterior iliac crest and a right posterior iliac crest of the subject using the harvesting syringes and a mini-bone marrow harvest technique to form harvested bone marrow; and (iii) infusing the harvested bone marrow into a collecting bag. In one embodiment, the harvesting syringes in step (i) and the collecting bag in step (iii) contain a preservative free heparinized solution comprising 0.9% normal saline. The final concentration of heparin in the heparinized saline solution is about 20 units per ml to about 25 units per ml.

Optionally, according to one embodiment of the method, the harvested bone marrow is transported to a processing facility different from the facility from which the bone marrow was harvested. According to one embodiment, the method for transporting the harvested bone marrow to the processing facility comprises the steps (a) placing the harvested bone marrow in a collection bag; (b) placing the collection bag in a secondary bag; (c) placing the secondary bag containing the collection bag in a shipping container comprising an interior compartment containing frozen wet ice and at least one sheet of bubble wrap; (d) affixing a temperature tag monitor to the interior compartment of the shipping container; (e) sealing the shipping container; and (f) shipping the shipping container to the processing facility.

In another aspect, the described invention provides a method for treating or preventing progressive myocardial injury due to a vascular insufficiency that occurs early or late. The method comprising the steps: (a) evaluating whether the subject qualifies for therapy with the pharmaceutical composition of the described invention; (b) preparing the pharmaceutical composition comprising a chemotactic hematopoietic stem cell product; (c) loading the pharmaceutical composition into a chemotactic hematopoietic stem cell product delivery apparatus; (d) delivering a therapeutically effective amount of the pharmaceutical composition to the subject; and (e) monitoring the subject's cardiac function. According to one embodiment, in step (d) the therapeutically effective amount of the pharmaceutical composition is delivered to the subject intravascularly (meaning inside a blood vessel). According to another embodiment, the vascular insufficiency that occurs early or late is an ischemia. According to some such embodiments, the ischemia is a myocardial ischemia. According to some such embodiments, the ischemia is a transient myocardial ischemia. According to some such embodiments, the ischemia is a chronic myocardial ischemia. According to some such embodiments, the ischemia is a peri-infarct border zone ischemia. According to one embodiment, the vascular insufficiency that occurs early or late is a vascular insufficiency after an acute myocardial infarction resulting from underlying disease. According to some such embodiments, the progressive myocardial injury is heart failure.

According to one embodiment of the described invention, the subject in need thereof is a revascularized myocardial infarction patient. The term "revascularized" as used in this embodiment refers to the successful placement of a stent. Clinical evaluations, for example, of coronary insufficiency using non-laboratory tests, cardiac catheterization, measurement of inflammatory cytokines, and measurement of cardiac biomarkers may be used to determine the appropriate time to administer the pharmaceutical compositions in accordance with the methods of the described invention. According to n some embodiments, detection of peak inflammatory cytokine cascade production enables the administration to be tailored to the therapeutic window most crucial for the particular subject. According to some embodiments, peak inflammatory cytokine cascade production is determined by measuring the levels of the appropriate cytokine(s) in the plasma and or urine. According to other embodiments, the level(s) of the appropriate cytokine(s) is/are measured immunochemically, for example, by a sandwich enzyme immunoassay, by enzyme-linked immunosorbent assays (ELISA) or by multiplex bead kits.

According to some embodiments, the composition is administered at a first infusion date. According to one embodiment, the first infusion date is a time after an inflammatory cytokine cascade production peaks. According to some embodiments, the first infusion date at which the composition is administered to a revascularized myocardial infarction patient is about 5 days to about 14 days post-infarction. In some embodiments, the minimum first infusion date in which to administer the composition to a revascularized myocardial infarction patient is about 5, 6, 7, 8, 9, 10, 11, 12, 13, or 14 days post-infarction. According to some embodiments, the maximum first infusion date in which to administer the composition to a revascularized myocardial infarction patient is about 14, 12, 11, 10, 9, 8, 7, 6, or 5 days post-infarction.

According to some embodiments, the composition is administered multiple times, or as needed in the judgment of the treating physician. According to one such embodiment, the composition is administered at the first infusion date, and optionally at a second infusion date, a third infusion date, a fourth infusion date, a fifth infusion date, a sixth infusion date, a seventh infusion date, an eighth infusion date, a ninth infusion date, a tenth infusion date, and so on.

According to some embodiments, the first infusion date at which the composition is administered to a revascularized subject suffering from a vascular insufficiency that occurs early or late after a myocardial infarction resulting from underlying disease comprises a specific time interval defined by a first time and a second time, wherein the first time is after peak inflammatory cytokine cascade production in the infarcted area and the second time is before myocardial scar formation in the infarcted area.

According to some embodiments, the first infusion date is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after occurrence of an AMI. According to some embodiments, the second infusion date is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 42 months, at least about 48 months, at least about 54 months, at least about 60 months, at least about 66 months, at least about 72 months, at least about 78 months, at least about 84 months, at least about 90 months, at least about 96 months, at least about 102 months, at least about 108 months, at least about 114 months, at least about 120 months, at least about 126 months, at least about 132 months, at least about 138 months, at least about 144 months, at least about 150 months, at least about 156 months, at least about 162 months, at least about 168 months, at least about 174 months, at least about 180 months, at least about 186 months, at least about 192 months, at least about 198 months, at least about 204 months, at least about 210 months, at least about 216 months, at least about 222 months, at least about 228 months, at least about 234 months, at least about 240 months or more after occurrence of an AMI. According to some embodiments, the first infusion date is at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI.

According to some embodiments, the third infusion date is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after occurrence of an AMI. According to some embodiments, the third infusion date is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 42 months, at least about 48 months, at least about 54 months, at least about 60 months, at least about 66 months, at least about 72 months, at least about 78 months, at least about 84 months, at least about 90 months, at least about 96 months, at least about 102 months, at least about 108 months, at least about 114 months, at least about 120 months, at least about 126 months, at least about 132 months, at least about 138 months, at least about 144 months, at least about 150 months, at least about 156 months, at least about 162 months, at least about 168 months, at least about 174 months, at least about 180 months, at least about 186 months, at least about 192 months, at least about 198 months, at least about 204 months, at least about 210 months, at least about 216 months, at least about 222 months, at least about 228 months, at least about 234 months, at least about 240 months after occurrence of an AMI. According to some such embodiments, the third infusion date is at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI.

According to some embodiments, the fourth infusion date is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after occurrence of an AMI. According to some embodiments, the fourth infusion date is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 42 months, at least about 48 months, at least about 54 months, at least about 60 months, at least about 66 months, at least about 72 months, at least about 78 months, at least about 84 months, at least about 90 months, at least about 96 months, at least about 102 months, at least about 108 months, at least about 114 months, at least about 120 months, at least about 126 months, at least about 132 months, at least about 138 months, at least about 144 months, at least about 150 months, at least about 156 months, at least about 162 months, at least about 168 months, at least about 174 months, at least about 180 months, at least about 186 months, at least about 192 months, at least about 198 months, at least about 204 months, at least about 210 months, at least about 216 months, at least about 222 months, at least about 228 months, at least about 234 months, at least about 240 months or more after occurrence of an AMI. According to some such embodiments, the third infusion date is at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI.

According to some embodiments, the fifth infusion date is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after occurrence of an AMI. According to some embodiments, the fifth infusion date is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 42 months, at least about 48 months, at least about 54 months, at least about 60 months, at least about 66 months, at least about 72 months, at least about 78 months, at least about 84 months, at least about 90 months, at least about 96 months, at least about 102 months, at least about 108 months, at least about 114 months, at least about 120 months, at least about 126 months, at least about 132 months, at least about 138 months, at least about 144 months, at least about 150 months, at least about 156 months, at least about 162 months, at least about 168 months, at least about 174 months, at least about 180 months, at least about 186 months, at least about 192 months, at least about 198 months, at least about 204 months, at least about 210 months, at least about 216 months, at least about 222 months, at least about 228 months, at least about 234 months, at least about 240 months or more after occurrence of an AMI. According to some embodiments, the first infusion date is at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI.

According to some embodiments, the sixth infusion date is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after occurrence of an AMI. According to some embodiments, the sixth infusion date is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 42 months, at least about 48 months, at least about 54 months, at least about 60 months, at least about 66 months, at least about 72 months, at least about 78 months, at least about 84 months, at least about 90 months, at least about 96 months, at least about 102 months, at least about 108 months, at least about 114 months, at least about 120 months, at least about 126 months, at least about 132 months, at least about 138 months, at least about 144 months, at least about 150 months, at least about 156 months, at least about 162 months, at least about 168 months, at least about 174 months, at least about 180 months, at least about 186 months, at least about 192 months, at least about 198 months, at least about 204 months, at least about 210 months, at least about 216 months, at least about 222 months, at least about 228 months, at least about 234 months, at least about 240 months or more after occurrence of an AMI. According to some such embodiments, the third infusion date is at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI.

According to some such embodiments, the seventh infusion date is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after occurrence of an AMI. According to some embodiments, the seventh infusion date is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 42 months, at least about 48 months, at least about 54 months, at least about 60 months, at least about 66 months, at least about 72 months, at least about 78 months, at least about 84 months, at least about 90 months, at least about 96 months, at least about 102 months, at least about 108 months, at least about 114 months, at least about 120 months, at least about 126 months, at least about 132 months, at least about 138 months, at least about 144 months, at least about 150 months, at least about 156 months, at least about 162 months, at least about 168 months, at least about 174 months, at least about 180 months, at least about 186 months, at least about 192 months, at least about 198 months, at least about 204 months, at least about 210 months, at least about 216 months, at least about 222 months, at least about 228 months, at least about 234 months, at least about 240 months or more after occurrence of an AMI. According to some such embodiments, the third infusion date is at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI.

According to some such embodiments, the eighth infusion date is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after occurrence of an AMI. According to some embodiments, the eighth infusion date is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 42 months, at least about 48 months, at least about 54 months, at least about 60 months, at least about 66 months, at least about 72 months, at least about 78 months, at least about 84 months, at least about 90 months, at least about 96 months, at least about 102 months, at least about 108 months, at least about 114 months, at least about 120 months, at least about 126 months, at least about 132 months, at least about 138 months, at least about 144 months, at least about 150 months, at least about 156 months, at least about 162 months, at least about 168 months, at least about 174 months, at least about 180 months, at least about 186 months, at least about 192 months, at least about 198 months, at least about 204 months, at least about 210 months, at least about 216 months, at least about 222 months, at least about 228 months, at least about 234 months, at least about 240 months or more after occurrence of an AMI. According to some such embodiments, the third infusion date is at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI.

According to some such embodiments, the ninth infusion date is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after occurrence of an AMI. According to some embodiments, the ninth infusion date is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 42 months, at least about 48 months, at least about 54 months, at least about 60 months, at least about 66 months, at least about 72 months, at least about 78 months, at least about 84 months, at least about 90 months, at least about 96 months, at least about 102 months, at least about 108 months, at least about 114 months, at least about 120 months, at least about 126 months, at least about 132 months, at least about 138 months, at least about 144 months, at least about 150 months, at least about 156 months, at least about 162 months, at least about 168 months, at least about 174 months, at least about 180 months, at least about 186 months, at least about 192 months, at least about 198 months, at least about 204 months, at least about 210 months, at least about 216 months, at least about 222 months, at least about 228 months, at least about 234 months, at least about 240 months or more after occurrence of an AMI. According to some such embodiments, the third infusion date is at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI.

According to some such embodiments, the tenth infusion date is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after occurrence of an AMI. According to some embodiments, the tenth infusion date is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 42 months, at least about 48 months, at least about 54 months, at least about 60 months, at least about 66 months, at least about 72 months, at least about 78 months, at least about 84 months, at least about 90 months, at least about 96 months, at least about 102 months, at least about 108 months, at least about 114 months, at least about 120 months, at least about 126 months, at least about 132 months, at least about 138 months, at least about 144 months, at least about 150 months, at least about 156 months, at least about 162 months, at least about 168 months, at least about 174 months, at least about 180 months, at least about 186 months, at least about 192 months, at least about 198 months, at least about 204 months, at least about 210 months, at least about 216 months, at least about 222 months, at least about 228 months, at least about 234 months, at least about 240 months or more after occurrence of an AMI. According to some such embodiments, the third infusion date is at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI, and so on.

According to some embodiments, the chemotactic hematopoietic stem cell product of the composition administered at the second, third, fourth, fifth, sixth, seventh, eighth, ninth and/or tenth infusion date is prepared from a frozen and thawed aliquot of a nonexpanded, isolated population of autologous mononuclear cells containing CD34+ cells.

According to some embodiments, the chemotactic hematopoietic stem cell product delivery apparatus used to deliver the pharmaceutical composition of the described invention to a subject in need thereof comprises an infusion syringe, a flushing syringe, a four-way stopcock, and a balloon catheter. In one embodiment, the intravascular delivery comprises (a) an infusion device attached to a sterile four-way stopcock containing the pharmaceutical composition comprising the chemotactic hematopoietic stem cell product; (b) a flushing device attached to the sterile four-way stopcock, the flushing device containing a flushing solution, and (c) a catheter attached to the delivery apparatus by the sterile four-way stopcock. According to one embodiment, the infusion device is a syringe made of any suitable material. The body and handle of suitable four way stopcocks may be made of the same or a different material. Examples of suitable four-way stopcocks includes, without limitation, a stopcock having a polycarbonate body/polycarbonate handle, a stopcock having a polyethylene body/polyethylene handle, a stopcock having a polycarbonate body/polyethylene handle, or a disposable stopcock. According to some embodiments, a device is further attached to the stopcock to regulate the pressure exerted on the delivered solution. According to some embodiments, an integral flush device or syringe is attached to the stopcock. According to one embodiment, the catheter is a balloon catheter. The term "balloon catheter" refers to a type of "soft" thin flexible tube having an inflatable "balloon" at its tip, which is used during a catheterization procedure to enlarge a narrow opening or passage within the body. The deflated balloon catheter is positioned, inflated to perform the necessary procedure, and deflated again to be removed.

The viability and potential efficacy of the chemotactic hematopoietic stem cell product of the described invention comprising potent CD34+/CXCR-4+ cells depends on the cells maintaining their potency as they pass through a catheter. The catheter used in the methods of the described invention has an internal diameter of at least 0.36 mm. Any type of catheter having an internal diameter of at least 0.36 mm may be effective in delivering the pharmaceutical compositions of the described invention.

For example, a flow control catheter, which slows drainage of blood through the coronary artery vasculature, allows the cells time to transit through the blood vessel wall and into the tissue.

In some embodiments, the catheter is a balloon catheter. For example, without limitation, the following balloon dilatation catheters available from Cordis, Boston Scientific, Medtronic and Guidant having an internal diameter of about 0.36 mm have been validated (see Table 1).

TABLE 1

Balloon catheter validated for infusion of selected CD34+ cells through the IRA

| Manufacturer | Name and Model No. | Balloon Dimensions | Lumen Internal Diameter |
| --- | --- | --- | --- |
| Cordis | Raptor OTW 579-130 | 15 mm × 3.0 mm | 0.36 mm (0.14 in.) |
| Boston Scientific | OTW Maverick 20620-1530 | 15 mm × 3.0 mm | 0.36 mm (0.14 in.) |
| Medtronic | OTW Sprinter SPR 3015W | 15 mm × 3.0 mm | 0.36 mm (0.14 in.) |
| Guidant | Voyager OTW 1009443-15 | 15 mm × 3.0 mm | 0.36 mm (0.14 in.) |

In addition, catheters have been described having a fluid delivery port adjacent to the balloon such that the balloon may be inflated against a vessel wall to isolate the delivery site from hemodynamics opposite the balloon from the port, which may be located distally of the balloon. Additionally, balloon catheters have been disclosed having lumens ending in side ports disposed proximally to the balloon catheter; these balloon catheters generally may be referred to as "balloon/delivery" catheters, although particular references may use different descriptors. See, e.g., U.S. Pat. No. 5,415,636 to Forman, incorporated by reference herein.

According to some embodiments, the method of treating or preventing a progressive myocardial injury due to a vascular insufficiency that occurs early or late comprises administering the progressive myocardial injury-preventing pharmaceutical composition via balloon catheterization into an artery at a first infusion date. In some embodiments, following angioplasty, a delivery balloon catheter is inserted via a femoral artery into a desired coronary artery, such as the left anterior descending coronary artery. Some medical conditions may require both a balloon catheter and a fluid delivery catheter to facilitate treatment.

According to some embodiments, a catheter is used to directly inject cells into the myocardium.

Treatment Regimens

According to another aspect, the described invention provides a regimen for treating a progressive myocardial injury due to a vascular insufficiency that occurs early or late, which comprises:

(a) first administering to the subject on a first infusion date a first sterile pharmaceutical composition parenterally through a catheter, the first sterile pharmaceutical composition of (a) comprising: (i) a therapeutically effective amount of a first sterile chemotactic hematopoietic stem cell product, wherein the first chemotactic hematopoietic stem cell product comprises a nonexpanded, isolated population of autologous mononuclear cells enriched for CD34+ cells, which further contain a subpopulation of potent CD34+/CXCR-4+ cells that have CXCR-4-mediated chemotactic activity, wherein the therapeutically effective amount of the first chemotactic hematopoietic stem cell product comprises at least $10 \times 10^6$ CD34+ cells containing at least $0.5 \times 10^6$ potent CD34+ cells expressing CXCR-4 and having CXCR-4 mediated chemotactic activity; (ii) a stabilizing amount of serum, wherein the stabilizing amount of serum is greater than 20% (v/v), wherein the chemotactic hematopoietic stem cell product is further characterized as having the following properties for at least 24 hours following acquisition of the chemotactic hematopoietic stem cell product when tested in vitro after passage through a catheter: (1) retains the CXCR-4-mediated activity of the subpopulation of potent CD34+/CXCR-4+ cells that have CXCR-4-mediated chemotactic activity; (2) at least 70% of the cells are CD34+ cells; (3) is at least 70% viable; and (4) is able to form hematopoietic colonies in vitro;

(b) second, administering at a second infusion date a second sterile pharmaceutical composition comprising a therapeutic amount of a second chemotactic hematopoietic stem cell product; wherein the therapeutically effective amount of the second chemotactic hematopoietic stem cell product comprises at least $10 \times 10^6$ CD34+ cells which further contain a subpopulation of at least $0.5 \times 10^6$ potent CD34+ cells expressing CXCR-4 and having CXCR-4 mediated chemotactic activity; (ii) a stabilizing amount of serum, wherein the stabilizing amount of serum is greater than 20% (v/v), wherein the second chemotactic hematopoietic stem cell product is further characterized as having the following properties for at least 24 hours when tested in vitro after passage through a catheter: (1) retains the CXCR-4-mediated activity of the subpopulation of potent CD34+/CXCR-4+ cells that have CXCR-4-mediated chemotactic activity; (2) at least 70% of the cells are CD34+ cells; (3) is at least 70% viable; and (4) is able to form hematopoietic colonies in vitro; and (c) third, optionally administering at a third infusion date a sterile pharmaceutical composition comprising a third chemotactic hematopoietic stem cell product comprising at least $10 \times 10^6$ isolated CD34+ cells, which further contain a subpopulation of at least $0.5 \times 10^6$ potent CD34+ cells expressing CXCR-4 and having CXCR-4 mediated chemotactic activity; (ii) a stabilizing amount of serum, wherein the stabilizing amount of serum is greater than 20% (v/v), wherein the third chemotactic hematopoietic stem cell product is further characterized as having the following properties for at least 24 hours when tested in vitro after passage through a catheter: (1) retains the CXCR-4-mediated activity of the subpopulation of potent CD34+/CXCR-4+ cells that have CXCR-4-mediated chemotactic activity; (2) at least 70% of the cells are CD34+ cells; (3) is at least 70% viable; and (4) is able to form hematopoietic colonies in vitro, such that the regimen improves at least one measure of cardiac function.

According to some embodiments, at least one aliquot of the sterile nonexpanded, isolated population of autologous mononuclear cells comprising CD34+ cells, which further contain a subpopulation of potent CD34+/CXCR-4+ cells that have CXCR-4-mediated chemotactic activity acquired from the subject under sterile conditions is frozen at −86° C. and cryostored at least one aliquot in the vapor phase of a liquid nitrogen freezer until needed. At that time, the at least one aliquot of the frozen nonexpanded, isolated population of autologous mononuclear cells containing CD34+ cells which further contain a subpopulation of potent CD34+/CXCR-4+ cells that have CXCR-4-mediated chemotactic activity is thawed and enriched for CD34+ cells, which further contain a subpopulation of potent CD34+/CXCR-4+ cells that have CXCR-4-mediated chemotactic activity. This frozen and thawed nonexpanded, isolated population of autologous mononuclear cells enriched for CD34+ cells which further contain a subpopulation of potent CD34+/CXCR-4+ cells that have CXCR-4-mediated chemotactic activity constitutes a thawed sterile chemotactic hematopoietic stem cell product.

According to some embodiments, the thawed sterile chemotactic hematopoietic stem cell product can be used in step (b), step (c), or steps (b) and step (c) of the regimen.

The term "regimen" as used herein refers to a course or plan of treatment to preserve or restore the health of a subject suffering from a progressive myocardial injury due to a vascular insufficiency that occurs early or late.

According to one embodiment of the regimen, the thawed sterile chemotactic hematopoietic stem cell product, when passed through the catheter and tested in vitro, (i) is able to form hematopoietic colonies; and (ii) retains at least 2% of the CXCR-4-mediated activity of the subpopulation of potent CD34+/CXCR-4+ cells that have CXCR-4-mediated chemotactic activity, for at least 48 hours following thawing of the cryostored nonexpanded, isolated population of autologous mononuclear cells comprising CD34+ cells, which further contain a subpopulation of potent CD34+/CXCR-4-+ cells that have CXCR-4-mediated chemotactic activity. According to another embodiment, the thawed chemotactic hematopoietic stem cell product, when passed through the catheter and tested in vitro, (i) is able to form hematopoietic colonies; and (ii) retains at least 2% of the CXCR-4-mediated activity of the subpopulation of potent CD34+/CXCR-4+ cells that have CXCR-4-mediated chemotactic activity for at least 72 hours following thawing of nonexpanded, isolated population of autologous mononuclear cells comprising CD34+ cells, which further contain a subpopulation of potent CD34+/CXCR-4-+ cells that have CXCR-4-mediated chemotactic activity.

According to another embodiment, the first infusion date of (a) is at least is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after occurrence of an AMI. According to some embodiments, the first infusion date of (a) is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 42 months, at least about 48 months, at least about 54 months, at least about 60 months, at least about 66 months, at least about 72 months, at least about 78 months, at least about 84 months, at least about 90 months, at least about 96 months, at least about 102 months, at least about 108 months, at least about 114 months, at least about 120 months, at least about 126 months, at least about 132 months, at least about 138 months, at least about 144 months, at least about 150 months, at least about 156 months, at least about 162 months, at least about 168 months, at least about 174 months, at least about 180 months, at least about 186 months, at least about 192 months, at least about 198 months, at least about 204 months, at least about 210 months, at least about 216 months, at least about 222 months, at least about 228 months, at least about 234 months, at least about 240 months or more after occurrence of an AMI. According to some embodiments, the first infusion date is at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI.

According to another embodiment, the second infusion date of (b) is at least about is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after occurrence of an AMI. According to some embodiments, the third infusion date of (c) is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 42 months, at least about 48 months, at least about 54 months, at least about 60 months, at least about 66 months, at least about 72 months, at least about 78 months, at least about 84 months, at least about 90 months, at least about 96 months, at least about 102 months, at least about 108 months, at least about 114 months, at least about 120 months, at least about 126 months, at least about 132 months, at least about 138 months, at least about 144 months, at least about 150 months, at least about 156 months, at least about 162 months, at least about 168 months, at least about 174 months, at least about 180 months, at least about 186 months, at least about 192 months, at least about 198 months, at least about 204 months, at least about 210 months, at least about 216 months, at least about 222 months, at least about 228 months, at least about 234 months, at least about 240 months or more after occurrence of an AMI. According to some embodiments, the first infusion date is at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI.

According to another embodiment, the third infusion date of (c) is at least about is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, or at least about 30 days after occurrence of an AMI. According to some embodiments, the third infusion date of (c) is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 42 months, at least about 48 months, at least about 54 months, at least about 60 months, at least about 66 months, at least about 72 months, at least about 78 months, at least about 84 months, at least about 90 months, at least about 96 months, at least about 102 months, at least about 108 months, at least about 114 months, at least about 120 months, at least about 126 months, at least about 132 months, at least about 138 months, at least about 144 months, at least about 150 months, at least about 156 months, at least about 162 months, at least about 168 months, at least about 174 months, at least about 180 months, at least about 186 months, at least about 192 months, at least about 198 months, at least about 204 months, at least about 210 months, at least about 216 months, at least about 222 months, at least about 228 months, at least about 234 months, at least about 240 months or more after occurrence of an AMI. According to some embodiments, the first infusion date is at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI.

According to another embodiment, the vascular insufficiency that occurs early or late is an ischemia. According to another embodiment, the ischemia is a myocardial ischemia. According to another embodiment, the ischemia is a transient ischemia. According to another embodiment, the ischemia is a chronic myocardial ischemia. According to another embodiment, the ischemia is a pen-infarct border zone ischemia. According to another embodiment, the catheter is a flow control catheter. According to another embodiment, the catheter is a balloon dilatation catheter. According to another embodiment, the catheter has an internal diameter of at least about 0.36 mm. According to another embodiment, the composition is administered through the catheter into myocardium. According to another embodiment, the composition is administered through the catheter intravascularly. According to another embodiment, the pharmaceutical composition further includes at least one compatible active agent. According to another embodiment, the active agent is selected from the group consisting of an angiotensin converting enzyme inhibitor, a beta-blocker, a diuretic, an anti-arrhythmic agent, a hematopoietic stem cell mobilizing agent, a tyrosine kinase receptor agonist, an anti-anginal agent, a vasoactive agent, an anticoagulant agent, a fibrinolytic agent, and a hypercholesterolemic agent. According to another embodiment, the tyrosine kinase receptor agonist is human neuregulin 1. According to some embodiments, the hematopoietic stem cell mobilizing agent is a colony stimulating factor. According to some such embodiments, the hematopoietic stem cell mobilizing agent comprises G-CSF, GM-CSF, or a pharmaceutically acceptable analog or derivative thereof. According to some embodiments, the hematopoietic stem cell mobilizing agent is a recombinant analog or derivative of a colony stimulating factor. According to some embodiments, the hematopoietic stem cell mobilizing agent is filgrastim.

According to another embodiment, the vascular insufficiency that occurs early or late is a vascular insufficiency after an acute myocardial infarction resulting from underlying disease. According to some such embodiments, the first infusion date comprises a specific time interval defined by a first time and a second time, wherein the first time is after peak inflammatory cytokine cascade production in the infarcted area and the second time is before myocardial scar formation in the infarcted area. According to another embodiment, in step (a), the first time of the first infusion date is at least about 5 days post-infarction. According to another embodiment, in step (a) the first time of the first infusion date is about 5 days post-infarction and the second time is about 14 days post-infarction. According to another embodiment, the regimen treats cardiomyocyte cell death in the peri-infarct border zone, relative to controls. According to another embodiment, the regimen treats hypoperfusion in the peri-infarct border zone, relative to controls. According to another embodiment, the regimen treats myocardial hibernation in the peri-infarct border zone, relative to controls. According to another embodiment, the regimen decreases infarct area, relative to controls. According to another embodiment, the regimen decreases infarct mass, relative to controls. According to another embodiment, the progressive myocardial injury is a progressive decline in heart muscle function following the acute myocardial infarction. According to another embodiment, the progressive myocardial injury is heart failure.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges also is encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and describe the methods and/or materials in connection with which the publications are cited.

As used herein and in the appended claims, the singular forms "a", "and", and "the" include plural referents unless the context clearly dictates otherwise. All technical and scientific terms used herein have the same meaning.

The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be confirmed independently.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Phase I Clinical Trial

Example 1

Selection of Eligible Subjects

Subjects/patients presenting with symptoms and clinical findings suggestive of a myocardial infarction will receive emergency diagnostic and clinical management according to institutional guidelines. If a transmural (meaning through the wall) myocardial infarction is confirmed, the time of first symptoms and the time of successful stent placement will be recorded. Revascularized subjects will receive appropriate medical management to reduce ventricular wall stresses according to institutional guidelines. The term "revascularized" as used in this embodiment, refers to the successful placement of a stent.

All types of stents, including drug-eluting stents (e.g., paclitaxel or sirolimus) are acceptable for use in the revascularization of the infarct related artery ("IRA"). Previous studies employing balloon catheters to infuse cell products have reported no limits for reference vessel diameter for the placement of the stent. Since this study is designed to distribute the cell product into the IRA circulation, and in an attempt to limit the potential for damage to very small vessels, the described invention requires that stents be placed prior to infusion of the chemotactic hematopoietic stem cell product of the described invention.

Stent-related drug effects occur predominantly at the site of contact of the stent with the vessel wall. Consequent to balloon dilatation, there is limited blood flow across the stent during cell infusion, and therefore no significant adverse drug-mediated effect on the CD34+ cells in the chemotactic hematopoietic stem cell product is expected. Moreover, prior clinical studies have shown that by 96 hours after drug-eluting stent placement, whole blood levels of either paclitaxel or sirolimus are below the limits of detection. Therefore, tissue levels in the myocardial sites to which the infused CD34+ cells expressing CXCR-4 and having CXCR-4-mediated chemotactic activity are intended to migrate are expected to be inconsequential. See Sousa, J. et al., Circulation 107: 2274-79, 2383-89 (2003).

During revascularization, a subject's cardiac function and perfusion will be assessed by standard methods. Relevant measures of cardiac function include assessment of global and regional ejection fraction, ventricular volumes, resting and stress perfusion, segmented wall motion, and, following a myocardial infarction, infarct size.

The term "diastole" refers to the normal postsystolic dilation of the heart cavities during which they fill with blood. The term "systole" refers to contraction of the heart, especially of the ventricles, by which the blood is driven through the aorta and pulmonary artery to traverse the systemic and pulmonary circulations, respectively.

The term "ejection fraction" ("EF") refers to the percentage of blood emptied from the ventricle during contraction More specifically, it is the fraction of the end-diastolic volume that is ejected with each beat; that is, it is stroke volume (SV) divided by end-diastolic volume (EDV). The volume of blood within a ventricle immediately before a contraction is known as the end-diastolic volume, while the volume of blood left in a ventricle at the end of contraction is known as end-systolic volume. The difference between end-diastolic and end-systolic volumes is the stroke volume, the volume of blood ejected with each beat. In a healthy 70-kg (1544) male, the SV is approximately 70 ml and the left ventricular EDV is 120 ml, giving an ejection fraction of 70/120, or 0.58 (58%). An EF within the range of from 55-60% is considered normal. The ejection fraction of the right ventricle ("RVEF") normally is equal to that of the left ventricle ("LVEF") within narrow limits.

Other measures of cardiac function include assessment of the stroke volume index and velocity of circumferential fiber shortening. Strauer, et al., Circulation 106: 1913-18 (2002). Stroke volume (SV) is the amount of blood the left ventricle ejects in one beat, measured in milliliters per beat (ml/beat). SV can be indexed to a patient's body size by dividing SV by Body Surface Area (BSA) to yield the Stroke Index (SI).

Assessment of repair of infarcted myocardium also has included evaluation of peri-infarct region perfusion using thallium scintigraphy. Id. The term "perfusion" refers to the process of nutritive delivery of arterial blood to a capillary bed in biological tissue. Perfusion ("F") may be calculated using the formula $F=(Pa-Pv)/R$, where Pa is mean arterial pressure, Pv is mean venous pressure, and R is vascular resistance:

Magnetic resonance imaging (MRI) is a useful tool for assessing cardiac function and viability (infarct size) in this setting. See Yin, A, et al., Blood 90: 5002-5012 (1997).

The day after successful stenting, subjects will be assessed for study eligibility and, if appropriate, will be offered informed consent to participate in the study. Subjects exhibiting symptoms for no more than three (3) days prior to successful stent placement will be assessed, prior to discharge, for study eligibility. Subjects found to meet eligibility criteria (see infra) will be offered informed consent to participate.

Consented subjects will have a study entry SPECT no sooner than 96 hours after stent placement. Subjects are eligible to proceed on study if the LVEF is less than or equal to 50% on echocardiography and a segmental ventricular wall abnormality is observed in the IRA. Eligible subjects immediately can complete baseline cardiac function and perfusion assessment.

Specifically, baseline cardiac function includes:

Cardiac Perfusion. Perfusion will be assessed using a routine Technetium (Tc-99m) Sestamibi radionuclide scan at rest and after intravenous adenosine. The Emory Cardiac Toolbox will be used for image quantification. Evaluation will use a 17-segment model. A core review lab will assess the perfusion studies with the interpreter blinded to the study cohort. Improvements in perfusion will be expressed in semi-quantitative terms (yes/no). The percentage of patients observed to have improvement in perfusion will be compared between dose cohorts.

MRI. Regional and global wall motion, infarct size, and left ventricular ("LV") volumes will be measured using MRI. Subjects will receive Gadolinium contrast during scanning. MRI scan will use the breath holding technique. Steady state precession imaging to obtain global and regional LV function will be performed as will Gadolinium imaging. Left ventricular end systolic and diastolic volumes, LVEF, LV end diastolic dimension, wall thickness in systole and diastole of the infarcted region, and infarct size will be reported using the AHA/AVV 17-segment model with transmural extent of the infarct reported as <25%, 26%-50%, 51%-75% and >76%. A core review laboratory will assess MRI with the interpreter blinded to the study cohort.

To be selected for this study, subjects must meet all of the following clinical criteria ("inclusion criteria"):
  Age: 18-75 years;
  Acute ST segment elevation myocardial infarction meeting ACC/AHA criteria, with symptoms of chest pain within 3 days of admission. Criteria include (ST elevation >1 mm in limb leads or 2 mm in two or more precordial leads and increased levels of troponin, creatine kinase MB (CPK MB) or both), New York Heart Association (NYHA) heart failure class (to be recorded) of I, II or III;
  Eligible for percutaneous coronary intervention (PCI);
  Eligible for MRI;
  Eligible for Single Proton Emission Computed Tomography (SPECT) imaging;
  Subject must be able to provide informed written consent and must be willing to participate in all required study follow-up assessments;
  Subjects must have a hemoglobin content (Hgb)>10 grams/dL, white blood cell count (WBC)>3500 cells/mm$^3$, a platelet count>100,000 cells/mm$^3$ and an international normalized ratio (INR, a blood coagulation test)<2.0 the day before the bone marrow collection;
  Subjects must have a serum creatinine <2.5, total bilirubin <2.0 within 7 days of the bone marrow collection;
  IRA and target lesion must be clearly identifiable when disease is present in more than one vessel;
  Successful reperfusion and intracoronary stent placement, with Thrombolysis In Myocardial Infarction (TIMI) 2 or 3 flow and IRA with <20% stenosis after revascularization;
  Subjects must be deemed eligible to receive conscious sedation, mini-bone marrow harvest, and second catheterization for Chemotactic Hematopoietic Stem Cell Product infusion;
  The type of stent used and time and date inserted must be recorded;
  Drug eluting stents should be limited to paclitaxel or sirolimus types;
  Included subjects must have an expected survival of at least one year and must not have multiple vessel disease after revascularization, or be expected to require intervention within 6 months of study entry.

Subjects who satisfy any one of the following criteria do not qualify for, and will be excluded from, the study ("exclusion criteria"):
  Subjects who are not candidates for percutaneous intervention, conscious sedation, MRI, SPECT imaging or mini-bone marrow harvest;
  History of sustained chest pain unrelieved by nitrates, occurring 4 or more days before revascularization;
  Subjects who fail to re-perfuse the infarct related coronary artery or to have successful stent placement;
  Subjects presenting with cardiogenic shock (systolic pressure <80 on vasopressors or intra aortic counterpulsation);
  Subjects with a side branch of the target lesion >2 mm and with ostial narrowing >50% diameter stenosis after revascularization;
  Subjects unable to receive aspirin, clopidogrel or ticlopidine;
  Subjects receiving warfarin must have an INR less than or equal to 2; the term INR refers to INR International Normalized Ratio, which is a system established by the World Health Organization (WHO) and the International Committee on Thrombosis and Hemostasis for reporting the results of blood coagulation (clotting) tests;
  Subjects with severe aortic stenosis;
  Subjects with severe immunodeficiency states (e.g., AIDS);
  Subjects with cirrhosis requiring active medical management;
  Subjects with malignancy requiring active treatment (except basal cell skin cancer);
  Subjects with documented active alcohol and for other substance abuse;
  Females of child bearing potential unless a pregnancy test is negative within 7 days of the mini-bone marrow harvest;
  Subjects with ejection fractions greater than 50% on study entry by SPECT (96 to 144 hours after stent placement);
  Subjects with less than three months of planned antiplatelet therapy post index procedure;
  Subjects with multi vessel disease after revascularization requiring subsequent planned intervention during the next 6 months;
  Subjects with participation in an ongoing investigational trial;
  Subjects with active bacterial infection requiring systemic antibiotics.

Baseline assessments of cardiac function and cardiac perfusion will be obtained one day prior to the planned mini-bone marrow harvest and infusion of the chemotactic hematopoietic stem cell product (see infra). A mini-bone marrow harvest ("MMH") will be performed the day following baseline assessment of cardiac function and cardiac perfusion.

Example 2

Cardiac Catheterization

Sterile Preparation and Draping

The subject will be brought into the Cardiac Catheterization Laboratory after the investigator has obtained an informed consent. The subject will receive a sterile preparation and draping in the Cardiac Catheterization Laboratory.

Cardiac Catheterization

Vascular access will be obtained by standard technique using right or left groin. A sheath will be placed in the femoral artery or the right or left brachial artery. Coronary arteriographic examination will be performed by obtaining standard views of both right and left coronary arteries. Multiple views will be obtained to identify the previously stented infarct related artery. All subjects will receive standard medications during the catheterization procedure in accordance with routine practice.

Example 3

Acquisition Process for Acquiring Chemotactic Hematopoietic Stem Cell Product that is then Enriched for CD34+ Cells While it is contemplated that any acquisition process appropriate for acquiring the chemotactic hematopoietic stem cell product comprising potent CD34+ cells is within the scope of the described invention, the following example illustrates one such process referred to herein as a mini-bone marrow harvest technique.

Preparation of Harvesting Syringes

Prior to the bone marrow harvest, forty 10 cc syringes loaded with about 2-ml of a preservative free heparinized saline solution (about 100 units/ml to about 125 units/ml, APP Cat. No. 42592B or equivalent) will be prepared under sterile conditions. Heparin will be injected via a sterile port into each of two 100-ml bags of sterile 0.9% normal saline solution ("Normal Saline", Hospira Cat. No. 7983-09 or equivalent) following removal of 10 cc to 12.5 cc of normal saline from each bag, resulting in a final heparin concentration of about 100 units/ml (U/ml) to about 125 units/ml (U/ml). 2-ml of the preservative free heparin solution (about 100 U/ml to about 125 U/ml) will be loaded under sterile conditions into each of the forty 10 cc syringes, which then are capped and placed into a sterile bag for transport to the harvesting site.

Subjects will be prepared for bone marrow harvest after written informed consent is obtained as detailed in Example 1. Conscious sedation will be provided using standard institutional procedures and guidelines. Bone marrow harvest will be conducted under sterile conditions. The term "sterile conditions" as used herein includes proper scrubbing and gowning with a sterile mask and gloves worn by the harvesting attending and assistant. The harvesting procedure can be performed outside of an operating room as follows; after sterile prepping and draping, each iliac crest should be anaesthetized with a 1% lidocaine solution using a minimum of 10-ml for each crest. The area of anesthesia should be a circular area no less than 10 cm in diameter. The harvesting needle is inserted until the iliac crest is punctured. The cap and stylet is removed and 2-ml of marrow is harvested into the 10-ml harvesting syringe containing 2-ml of the heparin solution. The syringe then is removed and placed on the sterile field. After re-inserting the stylet, the harvesting needle is advanced slightly and then rotated 90'. The stylet is then removed and an additional 2-ml of marrow is drawn into the harvesting syringe retrieved from the sterile field. This procedure is repeated two more times until the harvesting syringe contains 8-ml of marrow for a total of 10-ml of heparinized marrow at a final heparin concentration of about 20 U/ml to about 25 U/ml. Finally the full harvesting syringe is handed to the harvesting assistant and shaken and infused in the sterile collecting bag as described below. The harvesting physician then takes the other harvesting needle that had been flushed previously with the heparin solution and repeats this process.

The full harvesting syringe is infused in the sterile collecting bag as follows. The harvesting assistant is handed the full harvesting syringe and empties it in the 500-ml collecting bag though the sterile adaptor attached to the bag. Then the harvesting needle is flushed with the heparin solution in the flushing syringe and returned to the sterile field.

The harvesting process is repeated on one iliac crest until about 19 syringes have been collected and emptied in the collecting bag. The same process is repeated on the other iliac crest until another about 19 syringes have been filled. A total of thirty-eight 8 ml aspirations from both iliac crest (ideally 19 from each iliac crest) will result in 302-ml of bone marrow harvested in a final volume of 380 ml at a heparin concentration of about 20 U/ml to about 25 U/ml.

The collecting bag is sealed by tying off the connecting tube three times and then clamped distal to the ties. The bag is appropriately labeled "Human Bone Marrow Collection" and the results of the harvesting procedure, including final volume collected and any procedure related complication, are recorded on the Mayo Clinical Risk Score (MCRS) case report form. The completed label is affixed to the bone marrow bag. The bag then is placed in a sterile carrying bag to be transported to the processing facility.

Example 4

Preparation of the Bone Marrow Product for Transportation

In one embodiment, the harvested bone marrow is transported to the processing facility as follows. When the clinical site is prepared to ship the bone marrow preparation, 24-hour notice will be provided to the processing facility. The processing laboratory will make shipping arrangements at the earliest possible time for pickup for same day delivery to the processing laboratory. Immediately after the bone marrow is collected, the bone marrow product will be placed in the supplied shipping container. The shipping container contains two small blocks of frozen wet ice on the bottom and a sheet of bubble wrap on top of the wet ice. The bone marrow product is placed into a secondary bag and the secondary bag is placed on top of the bubble wrap. A temperature tag monitor (a sensor used to monitor the internal temperature) is affixed to the interior of the box. Another layer of bubble wrap then is placed on top of the product before the shipping container is sealed off.

Example 5

Selection of CD34+ Cells from the Harvested Bone Marrow Product

CD34+ cells will be isolated from the harvested bone marrow product. In one embodiment, CD34+ cells will be isolated using the anti-CD34 monoclonal antibody (Mab), Dynabeads® M-450 Sheep anti-Mouse IgG, and PR34+™ Stem Cell Releasing Agent components of the Isolex 300i Magnetic Cell Selection System (Baxter Healthcare Corp. Cat. No. 4R9734) as described in U.S. Pat. Nos. 5,536,475, 5,035,994, 5,130,144, 4,965,204, 5,968,753, 6,017,719, 6,251,295, 5,980,887, 6,676,937, U.S. Published Application No. 2003/0232050, and the Isolex 300i Package Insert, each of which is incorporated herein by reference. This operating system has been adapted for isolation of CD34+ cells from bone marrow according to the described invention.

Upon arrival at the processing laboratory, the harvested bone marrow product (in the collecting bag) is inspected immediately and the bag checked for any leakage. The collection should be free flowing with no apparent clumps and should not be hemolyzed. The collection will not be used if the integrity of the bag has been breached in any way.

The bone marrow product should be processed within about 12 hours to about 24 hours of inspection. A 300-ml or 400-ml transfer pack container is obtained, and a plasma transfer set is attached to the sampling port of the container. The bone marrow product is transferred from the collecting bag to the transfer pack container. The pooled bone marrow collection product is mixed thoroughly by inverting the container twenty (20) times.

The pooled bone marrow collection product then is sampled for analysis. In one embodiment, a total volume of 2.0 ml of the product is removed and aliquoted as follows: 0.3 ml is used for a duplicate run of Complete Blood Count (CBC) using a hematology analyzer; 0.2-ml is dispensed into a 75×100-mm glass tube for the detection of Gram positive and Gram negative bacteria by Gram Stain (Gram Stain Kit, VWR, Cat. NO. BB231401); as a sterility check, 0.6-ml is dispensed into a Tryptic Soy Broth (TSB) (VWR, Cat. No. 29446-184) bottle for aerobic bacteria growth assay, 0.6-ml is dispensed into a Fluid Thioglycollate Media (FTM) (VWR Cat. #29446-138) bottle for anaerobic bacteria growth assay, and 0.3-ml is used in flow analysis for CD34+ cell enumeration and cell viability.

The collection is weighed on an electronic scale, and the appropriate tare weight of the collection bag recorded. The relationship of the volume of the bone marrow product to the weight of the product can be expressed as $$\text{Volume (ml)} = [\text{Weight (gm) of product} - \text{Tare weight of bag (gm)}] \div 1.06 \text{ (gm/ml)} \quad \text{(Formula 1)}$$

The number of Total Nucleated Cells (TNC) in the bone marrow product is calculated using the white blood cell (WBC) count obtained from the CBC according to the following relationship:

$$\text{TNC} = \text{WBC}/\mu l \times 1000 \times \text{Product volume (ml)} \quad \text{(Formula 2)}$$

The number of CD34+ cells in the bone marrow product is calculated from the following relationship:

$$\text{Total CD34+ cells in the bone marrow product} = \text{Number of CD34+ cell}/\mu l \times 1{,}000 \times \text{Product volume (ml)} \quad \text{(Formula 3)}$$

The Red Blood Cell (RBC) volume of the bone marrow collection product is calculated from the following relationship:

$$\text{RBC volume (ml)} = \text{Product volume (ml)} \times \text{Hematocrit (\%)}/100 \quad \text{(Formula 4)}$$

If the collection contains more than 20 ml of RBC, red blood cell depletion is required. RBCs are depleted by centrifugation. Centrifugation at 1000×g for 20 minutes at ambient temperature is performed to separate the buffy coat from the RBCs. The term "buffy coat" refers to a thin grayish white fraction of a blood sample that contains most of the white blood cells (leukocytes). Immediately after centrifugation, a 60 ml syringe is connected to the bottom of the centrifugation bag and the RBCs are removed. More than one syringe may be needed to collect all the packed RBC. The RBC depleted bone marrow product then is washed to remove fat contents.

A 1-ml syringe is used to remove 0.3-ml of the RBC-depleted bone marrow cell product through the transfer set attached to the product bag and a CBC performed. The TNC of the RBC depleted bone marrow product is determined from the relationship:

$$\text{Total TNC of the RBC depleted product} = \text{WBC}/\mu l \text{ of RBC depleted product} \times 1000 \times 180\text{-ml} \quad \text{(Formula 5)}$$

The TNC recovery of the RBC depleted product, which must be at least 80% of the original product count, is calculated from the relationship:

$$\text{TNC recovery} = \frac{\text{TNC of the RBC depleted product}}{\text{TNC of the unprocessed product}} \times 100\% \quad \text{(Formula 6)}$$

The total RBC volume is calculated as described supra; the RBC volume in the RBC depleted product should be less than <20-ml.

In one embodiment according to the described invention, the Isolex 300i system is used to process the RBC-depleted product or the bone marrow product whose RBC volume is <20 ml according to the following processing steps:

(i) The bone marrow is washed automatically to remove platelets;

(ii) CD34 positive (CD34+) cells are labeled specifically for selection by incubation with the Isolex 300i CD34 monoclonal antibody (Mab);

(iii) Unbound reagent is removed by washing the cell suspension with buffer solution;

(iv) Sensitized CD34+ cells (meaning CD34+ cells labeled with CD34 Mab) are captured by Dynabeads M-450 Sheep anti-Mouse IgG;

(v) A selection column is used to separate the magnetically-labeled Dynabeads having captured $CD34^+$ cells from unwanted cells, which are washed through the selection column and collected in the Negative Fraction Bag; and (vi) PR34+ Stem Cell Releasing Agent releases CD34+ cells from the column, and the $CD34^+$ cells are collected in the End Product Bag. The system performs several washing steps, disposing of most of the liquid into the Buffer Waste Bag.

The Isolex® selected CD34+ fraction is assayed as follows to determine WBC and CD34+ cell yields. The volume of the CD34 Positive Fraction is determined by mixing the cells in the End Product Bag; the bag is gently massaged by hand to ensure even cell distribution. A transfer set is inserted into the sampling port of the End Product Bag and a 60-ml syringe attached. The cell suspension is withdrawn into the syringe (maximum 50-ml at a time) in order to measure the total volume.

A 3-ml or 5-ml syringe is used to remove a 2.0-ml sample from the End Product Bag through the transfer set for quality control testing. The aliquoted volumes of the samples and the analyses performed on those samples are as previously described, i.e., CBC: 0.3-ml; Gram stain: 0.3-ml; CD34+ cell enumeration and cell viability: 0.2-ml.

The total TNC of the CD34 Positive Fraction is calculated from the relationship:

$$\text{Total TNC of the Positive Fraction} = \text{WBC}/\mu l \text{ of the Positive Fraction} \times 1000 \times \text{Volume of the Positive Fraction} \quad \text{(Formula 7)}$$

The TNC recovery of the Positive Fraction, which must be less than 5% of the original product count, is calculated from the following relationship:

$$\text{TNC recovery} = \frac{\text{Total TNC of the Positive Fraction}}{\text{Total TNC of the unprocessed product}} \times 100\% \quad \text{(Formula 8)}$$

The total number of viable CD34+ cells in the Positive Fraction is determined from the following relationship:

Total CD34+ cells in the Positive Fraction=Number of CD34+ cells/µl of the final product×1,000× Final product volume (ml)　(Formula 9)

The CD34+ cell recovery of the Positive Fraction s calculated from the following relationship:

CD34+ cell recovery=Total CD34+ cells of the Positive Fraction÷Total CD34+ cells of the unprocessed product×100%　(Formula 10).

Example 6

Preparation of Selected CD34+ Cells for Transfusion

Samples of the chemotactic hematopoietic stem cell product will be removed to be assayed for WBC count, by flow cytometry (for CD34+ cell enumeration and viability), Gram stain, and sterility.

CD34+ cells are characterized by flow cytometric analysis featuring CD34bright and CD45dim fluorescence by double labeling with anti-CD34 and anti-CD45 antibodies (Beckman Coulter, PN IM3630). CD34+ cells and CD45+ cell viability is determined by excluding the dying cells which take up the intercalating DNA dye 7-aminoactinomycin D (7AAD). See Brocklebank A M, Sparrow R L. Cytometry. 2001; 46:254-261 (2001); Barnett D, et al. Br. J. Haematol. 106:1059-1062 (1999); Sutherland, et al., J Hematotherapy 5:213-226 (1996), and U.S. Pat. Nos. 4,520,110; 4,859,582; 5,055,556; European Patent No. 76.695; Canadian Patent No. 1,179,942 (PE, APC); U.S. Pat. No. 4,876,190 (PerCP); U.S. Pat. Nos. 5,268,486; 5,486,616; 5,569,587; 5,569,766; 5,627,027 (Cy); U.S. Pat. Nos. 4,714,680; 4,965,204; 5,035, 994 (CD34); U.S. Pat. No. 5,776,709 (Lyse/no-wash method); U.S. Pat. Nos. 5,723,218 and 5,187,288 (Tru-COUNT Tubes), the contents of each of which is incorporated by reference herein in its entirety.

Any flow cytometer or an equivalent device can be used for conducting analysis of CD34+ cell enumeration and viability. In one embodiment, the processing laboratory employs a BD FACSCalibur™ flow cytometer and BD FACSComp™ software is used for instrument setup and monitoring. A template and a panel of legend labels are preinstalled for acquisition and analysis. Prior to use, the reagents, namely CD45FITC/CD34PE, Stem-Count Fluorospheres, Concentrated Ammonium Chloride Lysing Solution, and 7AAD Viability Dye, are brought to ambient temperature. CD34+ cell controls are run as a positive control to affirm that the instrument is set up for analyzing CD34+ cells, and the results are compared with the manufacturer's pre-determined CD34 percent range.

The unprocessed bone marrow product and Isolex processed chemotactic hematopoietic stem cell products may be analyzed by many different procedures. In one embodiment, or example, immediately upon receiving the sample, if the WBC count of the sample is greater than 2×10$^7$ cells per ml, the sample is diluted with Sheath fluid to achieve a cell count of about 2×10$^7$ WBC per ml. 100 µl of the diluted product is aliquoted into two 15×100 mm tubes. Using a micropipetter, 20 µl of CD45FITC/CD34 PE and 7-AAD viability dye reagent are added into each tube and the samples gently vortexed. The tubes are covered with aluminum foil and left at ambient temperature for 15 to 20 minutes. RBCs are lysed by adding 1.5 ml of 1× Lysing Solution to each tube, vortexing gently. The tubes are incubated for ten minutes at ambient temperature, protected from light. The samples are stored at about 2° C.-about 8° C. (i.e., on an ice bath) protected from light until data acquisition is performed. Data acquisition must be performed within one hour of adding the lysing buffer. Before data acquisition, Stem-Count Fluorospheres are resuspended by end-over-end rotation (10 times). 100 µl of Fluorospheres is added to each tube and gently vortexed taking care not to generate air bubbles. The absolute count of CD34+ cells in the product is calculated from the relationship:

Number of viable CD34+ cells per µl of product=LCD34×FAC　(Formula 11)

where LCD34 is the averaged number of events for Live CD34+/All CD 45+; "FAC" is Fluorospheres Assayed Concentration; and F is the averaged number of Fluorosphere singlets counted.

The volume of CD34+ Positive Fraction is calculated to obtain the number of CD34+ cells required for the required dosing. The Required Positive Fraction Volume (ml) is defined as:

The Requested CD34+ cell dosage÷(Total CD34+ cells per µl in the Positive Fraction×1,000).　(Formula 12)

An appropriate number of cells is dispensed into a 50 ml conical tube and centrifuged at 500×g for 10 minutes. The supernatant is removed using a 30 ml serological pipette and disposed of as waste while exercising care not to disperse the cell pellets at the bottom of the tubes during this process. The infusion solution (20 ml) is added into the CD34+ Cell Positive Fraction tube and the cells dispersed using a 10 ml serological pipette by repeat pipetting. The resuspended cells are centrifuged for 10 minutes at 500 g. A 30 ml serological pipette is used (without disturbing the cell pellet) to transfer the supernatant/infusion solution into a 50 ml conical tube with a label "Positive. Fraction Supernatant" affixed. The tube containing the supernatant is vortexed to homogenize the solution. A 10 ml serological pipette is used to transfer 10 ml of the homogenized supernatant back to the CD34+ Cell Positive Fraction tube. The remaining 10 ml of suspension in the Supernatant tube will be used for sterility testing (5 ml each into a TSB (Trypticase Soy Broth) bottle and an FTM (Fluid Thioglycollate) bottle). The cells in the CD34+ Cell Positive Fraction are resuspended by slowly withdrawing and aspirating through a blunt end needle affixed to a 10 ml syringe (Infusion Syringe) several times. The cell suspension is withdrawn into the syringe, any air bubbles re aspirated off, and the blunt end needle removed. The infusion syringe is attached to the injection port of a 4-way stopcock.

The chemotactic hematopoietic stem cell product of the described invention will be released for infusion only if it meets the following criteria:

CD34$^+$ cell purity of at least about 70%, 75%, 80%, 85%, 90% or 95%;

A negative Gram stain result for the selected positive fraction;

Endotoxin Levels: less than about 0.5 endotoxin units/ml;

Viable CD34$^+$ cell yield of the "Chemotactic hematopoietic stem cell product" meets the required dosing as per the treatment cohort;

CD34$^+$ cells are at least about 70%, 75%, 80%, 85%, 90% or 95% viable by 7-AAD;

USP sterility result for "Positive Fraction Supernatant": negative (14 days later); and Bone marrow CD34$^+$ cell selection was initiated within about 12 hours to about 24 hours of completion of bone marrow harvest.

Sterility assessment on the stem cell product including gram staining and endotoxin will be performed prior to product release for infusion. USP sterility (bacterial and fungal) culture will be performed and the results will be reported to the principal investigator. In the event of a positive USP sterility result, the subject and attending physician on call will be notified immediately, provided with identification and sensitivity of the organism when available, and documentation of appropriate anti-microbial treatment and treatment outcome will be recorded by the investigative site and the sponsor.

After meeting these release criteria, the chemotactic hematopoietic stem cell product will be released for infusion and packaged for transportation to the catheterization facility. A sample also will be sent for in vitro testing.

According to some embodiments, product will be released only if CD34+ cell selection is initiated within 12 hours to about 24 hours of completion of bone marrow harvest and only if it is to be infused within about 48 hours to about 72 hours of completion of bone marrow harvest.

According to some embodiments, the nonexpanded, isolated population of autologous mononuclear cells containing CD34+ cells, which further contain potent CD34+/CXCR-4+ cells that have CXCR-4-mediated chemotactic activity is divided into aliquots, which are frozen at −86° C. and cryostored in the vapor phase of a liquid nitrogen freezer for subsequent administration. Each of these aliquots can be used to prepare a thawed chemotactic hematopoietic stem cell product as follows. The frozen nonexpanded, isolated population of autologous mononuclear cells are thawed at a sufficient time before planned administration the sterile nonexpanded, isolated population of autologous mononuclear cells comprising CD34+ cells, which further contain a subpopulation of potent CD34+/CXCR-4+ cells that have CXCR-4-mediated chemotactic activity will be enriched for CD34+ cells, which further contain a subpopulation of potent CD34+/CXCR-4+ cells that have CXCR-4-mediated chemotactic activity so as to yield the thawed chemotactic hematopoietic stem cell product. Samples of this thawed chemotactic hematopoietic stem cell product will be removed to be assayed for WBC count, by flow cytometry (for CD34+ cell enumeration and viability), Gram stain, and sterility. The thawed chemotactic hematopoietic stem cell product will be released for infusion within about 48 hours to about 72 hours of thawing of the frozen aliquot of the sterile nonexpanded, isolated population of autologous mononuclear cells comprising CD34+ cells.

Example 7

Formulation of the Chemotactic Hematopoietic Stem Cell Product Comprising CD34+ Cells The chemotactic hematopoietic stem cell product is formulated in 10-ml of saline (0.9% Sodium Chloride, Injection, USP, Hospira, Cat#7983-09) supplemented with 1% HSA (Human Albumin USP, Alpha, Cat. #521303) ("Infusion Solution") and more than 20% autologous serum. In addition, there may be some trace amount of materials (quantities not determined) in the Chemotactic hematopoietic stem cell product that are used and left over during the product processing. These materials include: Dulbecco's Phosphate Buffered Saline-Ca++, Mg++ Free (D-PBS) (Baxter, Cat. #EDR9865), Sodium Citrate (Baxter/Fenwal, Cat. #4B7867), Hetastarch (Abbott Laboratories, Cat. #0074-7248-03), IVIg (Gammagard® Immune Globulin Intravenous, Baxter, Cat. #060384) and the reagents in the Isolex® 300i Stem Cell Reagent Kit (Baxter, Cat. #4R9734) including anti-CD34 monoclonal antibody, stem cell releasing agent and Sheep anti-mouse magnetic beads.

Example 8

Transporting Chemotactic Hematopoietic Stem Cell Product to the Catheterization Facility According to the original plan, the chemotactic hematopoietic stem cell product that met the release criteria was to be loaded into a sterile 10 cc syringe in a Class 100 biological safety cabinet located within a controlled aseptic environment, e.g., at minimum, a Class 100,000 cell processing facility; class 10,000 is preferable, but not required. The chemotactic hematopoietic stem cell product was suspended in 10-ml PBS supplemented with HSA and the container labeled in accordance with release criteria. The original plan called for four dosing cohorts consisting of five subjects each in each cohort. The first was to receive about $5 \times 10^6$ CD34+ cells, the second about $10 \times 10^6$ CD34+ cells, the third about $20 \times 10^6$ CD34+ cells and the fourth about $30 \times 10^6$ CD34+ cells. Subjects in the higher dosing cohorts with inadequate CD34+ cell quantities to meet the assigned cohort dose were to be added to a prior cohort at the greatest possible CD34+ cell dose. The loaded infusion syringe was attached to a four-way stopcock along with a flushing syringe, capped and have safety guards applied to prevent leakage. The delivery apparatus was sealed in a double sterile bag and placed in a secure transportation box for transportation to the cardiac catheterization facility. Following release of the chemotactic hematopoietic stem cell product and cohort assignment, the chemotactic hematopoietic stem cell product was shipped to the catheterization site for direct infarct-related artery infusion ("intravascular administration").

Example 9

Intra-Coronary Infusion of Chemotactic Hematopoietic Stem Cell Product

Upon notification from the cell processing facility that the chemotactic hematopoietic stem cell product had been released for infusion (see supra), the subject/patient was scheduled to arrive at the catheterization facility at a time to coincide with the arrival of the chemotactic hematopoietic stem cell product.

Cardiac enzymes (brain natriuretic peptide (BNP), troponin and CPK MB), complete blood counts, a full chemistry panel (renal and liver function test) and an EKG were performed just prior to chemotactic hematopoietic stem cell product infusion. Clinical assessment of the stage of heart failure according to the New York Heart Association's (NYHA) functional classification system was recorded.

Upon receipt of the chemotactic hematopoietic stem cell product and final quality assurance release (by facsimile) for infusion, the subject 1 did undergo cardiac catheterization as detailed above. Coronary arteriography was performed to assess for patency (meaning openness, freedom from blockage) of the infarct related artery and Thrombolysis in Myocardial Infarction (TIMI) angiographic flow. A balloon catheter over a wire was placed in the stented segment of the infarct related artery. Any appropriate balloon dilatation catheter having an internal diameter of at least about 0.36 mm compatible with the chemotactic hematopoietic stem cell product infusion can be used. After positioning, the balloon wire was removed. The chemotactic hematopoietic stem cell product delivery apparatus was removed from the transportation case.

The delivery apparatus was in a sterile bag and had safety blocks attached to the infusion syringe (containing the chemotactic hematopoietic stem cell product) and the flushing syringe. The apparatus consisted of the infusion syringe (containing 10 ml of the chemotactic hematopoietic stem cell product) and the flushing syringe (containing 6 ml of flushing solution) wherein both were attached to a sterile four-way stopcock. The entire delivery apparatus was shaken gently to resuspend the CD34+ cells in the infusion solution. The flushing syringe was used to eliminate all air bubbles in the apparatus (to prevent air emboli) and the delivery apparatus then attached to the balloon dilatation catheter via the stopcock.

Delivery of the chemotactic hematopoietic stem cell product to the subject by infusion proceeded as follows. First, with the stopcock open between the flushing syringe (6 ml solution) and the central lumen of the balloon catheter, 1 ml of flushing solution was infused (after removal of the guard) into the central lumen of the catheter over 15 seconds. Second, the balloon was inflated at two atmospheres of pressure within the stent to avoid damage to the coronary artery endothelium and then the stopcock valve adjusted to allow infusion of the chemotactic hematopoietic stem cell product distal to the inflated balloon (after removal of the guard). With the balloon inflated, about 3 cc to about 4 cc from the infusion syringe was infused by hand over a period of about 30 seconds to about 45 seconds (to be timed and documented). The balloon remained inflated to allow adhesion of the CD34+ cells and to prevent back flow for a total of about 2 minutes to about 3 minutes (including the time for infusion). In between infusions, the balloon remain deflated for 3 minutes to allow restoration of blood flow (reperfusion). It was expected that 3 infusions will be required to empty the infusion syringe. Third, upon completion of infusing the chemotactic hematopoietic stem cell product and with the balloon deflated, the valve on the stopcock was adjusted to allow filling of the infusion syringe from the flushing syringe. Finally, with the balloon inflated (about 2 minutes to about 3 minutes), the 4 ml of flushing solution now in the infusion syringe was infused over a period of about 30 seconds to about 45 seconds to dislodge any residual CD34+ cells from the syringe and catheter into the IRA circulation. The catheter then was removed.

An infusion-related ischemia (inadequate blood flow) assessment was performed during the first 24 hours after chemotactic hematopoietic stem cell product infusion. An EKG at about 12 hours and at about 24 hours and analytical chemistry of cardiac enzymes (BNP, troponin and CPK MB) about every 8 hours for about 24 hours was obtained. Arrhythmia assessment (24 hour Holter monitor) was performed immediately post-chemotactic hematopoietic stem cell product infusion.

All subjects were provided with digital thermometers and a log book to record twice daily temperatures for 30 days post infusion of the chemotactic hematopoietic stem cell product. Subjects were instructed to notify the investigator site immediately for temperatures recorded above 100.5° F. Rapid follow-up with appropriate cultures and radiographic assessments was performed according to routine clinical standards. Documented bacterial infections, if any, were reported to the IRB and the FDA.

Additional follow-up visits for safety assessments included visits at 1 week and 2 weeks after product administration. Visit assessments included a comprehensive medical history and physical examination, EKG, complete blood counts, full chemistry panel (renal and liver function test), and measure of serum cardiac markers (BNP, troponin and CPK MB). Clinical assessment of NYHA functional class was recorded on week 1 and 2. At 4 weeks post chemotactic hematopoietic stem cell product infusion, an EKG and cardiac enzymes (BNP, troponin and CPK MB) was obtained. A 24 Holter monitor was used to assess for arrhythmias. Clinical assessment of NYHA functional class was recorded. Treadmill exercise testing using a symptom limiting Bruce protocol was performed as well.

At about 3 months and about 6 months post chemotactic hematopoietic stem cell product infusion at the first infusion time, a 24 hour Halter monitor was performed. Clinical assessment of NYHA functional class was recorded. At about 6 months post chemotactic hematopoietic stem cell product infusion, a symptom limited treadmill exercise testing using the Bruce protocol was recorded.

A safety assessment at about 12 months post chemotactic hematopoietic stem cell product infusion will include a comprehensive medical history and physical examination, EKG, complete blood counts, full chemistry panel (renal and liver function test), and measure of serum cardiac markers (BNP, troponin and CPK MB). A 24 hour Holter monitor will be performed. Clinical assessment of NYHA functional class will be recorded.

Statistical Analysis

A paired design, where each subject serves as his or her own control, was used in some embodiments. Differences between before and after treatment, per subject, were analyzed for each of the four numeric cardiac functions (i.e., myocardial contractility; end systolic volume, end diastolic volume; and perfusion). Linear regression analysis was used to assess the significance of increased dosing levels. The null hypothesis is that the slope of the regression line (dosing level serving as the independent variable and the "after" minus the "before" difference serving as the dependant variable) is equal to zero. The power of rejecting a false null hypothesis is 0.68 at the 0.05 alpha level of significance for a high correlation of 0.5 between dosing and improvement in cardiac function. The 95% confidence interval about the slope of the regression line was used to assess the medical significance of the increase in dosing level. If the slope of the regression line was not significantly different from zero but the intercept of the regression line is different from zero, then all treatment groups was combined and a paired t-test will be performed to assess the overall treatment effectiveness. The null hypothesis is that the mean of the differences is equal to zero. A Wilcoxon signed-ranks test also was performed as an additional test to determine the treatment effectiveness. This test is more powerful (rejecting a false null hypothesis) than a t-test if the observations are not normally distributed. The power of the t-test is 0.79 for rejecting a false null hypothesis at the alpha level of 0.05 and the treatment having a medium size effect (an effect large enough to be discernable by the naked eye). The medical significance of the treatment effect size was determined by computing a 95% confidence interval about the mean of the differences (the true mean of the differences will lay in this interval in 95% of tested samples).

To assess improvement in perfusion, logistic regression was used with dosing level as the independent variable and perfusion change (1=yes, 0=no) as the dependant variable. Odds ratios of the four dosing levels was computed separately with $5.0 \times 10^6$ cells serving as the index group.

A binomial test was used to assess the significance of CD34+ cell dosing on perfusion. It was expected that there would be no spontaneous improvement in a perfusion defect if present on the baseline perfusion scan. Therefore, any clinically significant improvement in a perfusion defect when assessed at 6 months and compared to baseline was considered a treatment effect.

A concurrent group (non-treated controls) meeting eligibility but not receiving CD34+ cells was evaluated similar to the treated group and assessed for significant improvement in cardiac function/perfusion. Each study site alternated accrual of treated and non-treated controls. A coin flip was used to determine the initial (treated or non-treated) subject sequence at each site. Comparison of outcomes between treated and non-treated groups was made. The core lab was blinded regarding treatment or no-treatment.

An assessment was performed to determine if a correlation existed between clinical outcome and cell content (CD34+) and/or in vitro colony growth (CFU-GM, CFU-GEMM, BFU-E), CXCR-4 mobility, and CXCR-4 surface antigen expression.

As originally planned, a total of 20 subjects were to receive the chemotactic hematopoietic cell product of the described invention. There were to be four dose cohorts (about $5 \times 10^6$, about $10 \times 10^6$, about $20 \times 10^6$, and about $30 \times 10^6$ CD34+ cells). If the chemotactic hematopoietic stem cell product content in any subject was not sufficient for the assigned cohort, that subject was reassigned to a prior cohort at the greatest possible dose. Subjects having fewer than $5 \times 10^6$ CD34+ cells available for infusion were removed from the study, did not undergo repeat catheterization and were not counted as part of the 20-subject study group. In addition, if the chemotactic hematopoietic cell product of the described invention did not meet release criteria, the subject did not receive the cell product and was not counted as a study candidate to be replaced by the next subject. In any cohort dosing group, if a subject experienced an acute (meaning immediate to about 7 days post infusion) unexpected toxicity considered to (probably) be a result of the cell product infusion, dose escalation was halted and 3 additional subjects were accrued to that dose level. If no other unexpected toxicity was observed, then dose escalation resumed, however the total of 20 subjects was not exceeded. If another toxicity occurs at that dose level, then all subsequent subjects were accrued to the next lower dose level.

The chemotactic hematopoietic stem cell product of the described invention was not administered to any subject in the higher dose cohort until all the subjects from the prior dose cohort had completed their follow-up assessments two weeks after product administration.

Example 10

Experimental Results of Preliminary Studies

A series of preliminary preclinical studies were performed in an attempt to accomplish the following goals:

(1) Optimize the manufacturing process for the Mini bone-Marrow Harvest (MMH);

(2) Evaluate the stability of the inbound MMH product and the outbound hematopoietic cell product.

(3) Evaluate the internal diameter allowance and safety of the catheters;

(4) Evaluate the compatibility of the cell product with the catheters intended to be used in the study; and (5) Evaluate the suitability of using the supernatant of the final hematopoietic cell product to represent the final hematopoietic cell product for stability testing.

Study 1: Optimizing the Manufacturing Process for the Mini Bone-Marrow Harvest (MMH)

The effect of key manufacturing variables on the yield of viable CD34 cells from representative bone marrow products was evaluated. A total of six (6) volunteer donors over the age of 45 (based on a range of 45-57) and three under 30 years of age (based a range of 21-28) agreed to donate an average of 45 ml (based on a range of 31 ml-54 ml) bone marrow and provided written Informed Consent for the procedure. The marrow aspiration technique employed was identical to that to be performed for the clinical scale MMH (see Example 3, supra). As shown in Table 2, the cell counts of nucleated cell (NC) and CD34+ cells of Mini bone-Marrow Harvest ("MMH") derived cells collected from volunteer donors appeared to be age related.

TABLE 2

Effect of donor age on nucleated cell yield of the MMH.

| | Donor age group | | | | | |
|---|---|---|---|---|---|---|
| | Over 45 (45-57) | | | Under 30 (23-28) | | |
| Donor | Volume of MMH (ml) | Viability (%) | CD34 cells ($10^5$ per ml) | Volume of MMH (ml) | Viability (%) | CD34 cells ($10^5$ per ml) |
| 1 | 31.30 | 83.85 | 1.27 | 48.00 | 96.90 | 7.98 |
| 2 | 43.50 | 97.42 | 3.89 | 50.60 | 96.28 | 11.60 |
| 3 | 51.50 | 85.74 | 1.37 | 39.90 | 87.17 | 5.99 |
| 4 | 47.50 | 80.95 | 1.76 | — | — | — |
| 5 | 53.70 | 98.21 | 5.58 | — | — | — |
| 6 | 44.90 | 96.36 | 4.48 | — | — | — |
| Avg. | 45.40 | 90.42 | 3.06 | 46.17 | 93.45 | 8.52 |

The average cell count of the bone marrow products from older donors (N=6) was $28.4 \times 106$ (based on a range of $15.8 \times 10^6$-$49.5 \times 10^6$) nucleated cells per ml ["NC/ml"], with an average viability, as determined by 7-AAD dye exclusion and flow cytometry, of 90.42% (based on a range of 80.95%-98.21%) and CD34+ content of $3.06 \times 10^5$/ml (based on a range of $1.27 \times 10^5$/ml-$5.58 \times 10^5$/ml). In the younger subject group (N=3), the average cell count collected from marrow aspiration was $46.2 \times 10^6$ NC/ml (based on a range of $39.9 \times 10^6$ NC/ml-$50.6 \times 10^6$ NC/ml), with an average 7-AAD viability of 93.5% (based on a range of 87.17%-96.90%) and total $CD34^+$ content of $8.5 \times 10^5$/ml (based on a range of $5.99 \times 10^5 CD34^+$ cells/ml-$11.60 \times 10^5$ $CD34^+$ cells/ml).

Red Cell Depletion and CD34 Selection

TABLE 3

CD34+ cell recovery after RBC depletion of MMH from older age group (4557) donors.

| | Donor | | | | | |
|---|---|---|---|---|---|---|
| | 1 | 2 | 3 | 4 | 5 | Average |
| Method of RBC depletion | Hetastarch | Buffy coat | Buffy coat | Buffy coat | Buffy coat | — |
| CD34+ cell % in MMH: Pre-RBC depletion | 1.09 | 1.64 | 1.63 | 1.45 | 1.99 | 1.58 |
| CD34+ cell % in MMH: Post-RBC depletion | 1.33 | 1.55 | 1.51 | 1.61 | 1.84 | 1.57 |
| CD34+ cell recovery post RBC depletion (%) | 65.68 | 92.36 | 80.66 | 78.79 | 81.67 | 79.83 |

As shown in Table 3, following red cell depletion of the MMH-derived bone marrow products collected from the older donors, an average of 79.83% (based on a range of 65.68%-92.36%) of the CD34 cells from the initial MMH was recovered. There was no significant difference between the initial CD34 cell purity (1.58%, based on a range of 1.09%-1.99%) and that following red cell depletion (1.57%, based on a range of 1.33%-1.84%). Assay methods to quantify chemotaxis are well known in the art, and a wide variety of techniques are used to evaluate chemotactic ability of a variety of cell types. Furthermore, cell migration assays are commercially available.

The assay used for the determination of in vitro migratory activity of CD34+ cells mediated by CXCR-4, which is adapted from an assay described in Jo et al (J. Clin. Invest. 105: 101-11 (2000)), relies on transmembrane migration of CD34+ cells. Transmembrane migration of CD34+ cells from the upper chamber to the lower chamber of a transwell polystyrene plate (6.5 mm diameter, 5 um pore size, Costar) is induced by SDF-1 placed in the lower chamber. The number of migrated viable CD34+ cells in the lower chamber then is determined by flow cytometry analysis using CD34/CD45 antibodies and 7-AAD. Control spontaneous migration of CD34+ cells is performed without SDF-1 in the lower chamber.

The subpopulation of potent cells that (i) express CXCR-4 and (ii) have CXCR-4 mediated chemotactic activity, expressed VEGFR-2 at very low levels (mean 0.84%, range 0 to 2.39%). Because the subpopulation of potent CD34+ cells co-expresses CXCR-4, {CXCR-4 co-expression; mean 60.63%, median 52% range 31-98% of CD34+ cells, capable of migrating in an SDF-1 gradient} while less than 2.5% of the CD34+ cells co-expresses VEGFR-2, functionally, these cells are VEGFR-2-, i.e., VEGFR-2 is not what drives the cells into the peri-infarct zone.

TABLE 4

CD34+ cell recovery, purity, CXCR-4 migratory activity, viability and hematopoietic CFU growth immediately after Isolex processing of MMH from older age group (age 45-age 57) donors.

| | Donor | | | | | |
|---|---|---|---|---|---|---|
| | 1 | 2 | 3 | 4 | 5 | Average |
| Storage time (hours) at 4° C.-8° C. | 0 | 0 | 0 | 12 | 10.50 | — |
| CD34+ cell recovery (%) | 32.36 | 29.09 | 15.31 | 43.60 | 40.20 | 32.11 |
| CD34+ cell purity (%) | 76.76 | 73.64 | 71.66 | 72.52 | 72.01 | 73.32 |
| CD34+ cell viability | 98.49 | 93.80 | 97.38 | 98.28 | 98.39 | 97.27 |
| CD34+ cell CXCR-4 migratory activity (%) | 22.10 | 2.60 | 22.00 | 19.90 | 19.70 | 17.26 |
| Hematopoietic CFU/100 CF34+ cells cultured | 27.5 | 25.0 | 18.9 | 17.0 | 21.00 | 21.9 |

As shown in Table 4, following CD34 selection using the Isolex system, which includes immunomagnetic Dynabeads® and anti-CD34 mAb, an average of 32.11% (based on a range of 15.31%-43.60%) of the CD34 cells was recovered with an average purity of 73.32% (based on a range of 71.66%-73.64%) and an average viability of 97.27% (based on a range of 93.80%-98.49%). In addition, these CD34+ cells displayed an average of 17.26% (based on a range of 2.60%-22.10%) CXCR-4 migratory ability immediately after selection and were capable of generating hematopoietic colonies (21.89 colonies/1C CD34+ cells plated (based on a range of 17.0 colonies/100 CD34+ cells plated-27.5 colonies/100 CD34+ cells plated) in MethoCult culture.

Study 2: Evaluation of the Stability of the Inbound Mini-Bone Marrow Harvest and of the Outbound Chemotactic hematopoietic Cell Product A series of experiments, using healthy volunteers, was performed in order to evaluate the stability of the inbound MMH and of the outbound chemotactic hematopoietic stem cell product of the described invention. Assessment of the functional viability of the inbound and outbound products was evaluated by cell viability (7-AAD), SDF-1/CXCR-4 mediated CD34+ cell migration, and the ability to form hematopoietic colonies in methylcellulose (CFU colony forming ability).

To evaluate the inbound product stability for shipping and logistic purposes and for coordination with clinical schedules, MMH products were stored at 4° C. to 8° C. as indicated. To evaluate the outbound product stability for shipping and logistic purposes, the chemotactic hematopoietic stem cell product comprising isolated CD34+ cells enriched following MMH was stored at 4° C. to 8° C. as indicated.

In preliminary studies, cells either were processed immediately or maintained at 4-8° C. for 12 hours prior to processing to evaluate the impact of shipping and logistic duration on the manufacture of a suitable cell product for infusion. Despite the duration of storage prior to processing (inbound product expiration), the results did not vary significantly (data not shown).

In another series of experiments, cells were stored at about 4° C. to about 8° C. for 12 hours and about 24 hours prior to reassessment to simulate products infused at about 36 hours and at about 48 hours, respectively, following MMH.

TABLE 5

CD34+ cell viability, growth and CXCR-4 migratory activity 13-13.5 hours after Isolex processing of MMH.

|  | Donor | | |
|---|---|---|---|
|  | 1 | 2 | Average |
| CD34+ cell viability (%) | 97.59 | 96.90 | 97.24 |
| CD34+ cell CXCR-4 migratory activity (%) | 7.70 | 7.50 | 7.60 |
| Hematopoietic CFU/100 CD34+ cells cultured | 18.00 | 25.00 | 21.5 |

As shown in Table 5, the isolated CD34+ cells of the chemotactic hematopoietic stem cell product had an average viability of 97.24% (based on a range of 96.90%-97.59%) and average CXCR-4-mediated migratory capacity of 7.60% (based on a range of 7.50%-7.70%). As shown in Table 6, after storage for an average of 26.3 hours (based on a range of 26.0 h-26.5 h), these cells had an average viability of 96.81% (based on a range of 96.39%-97.22%) and an average CXCR-4-mediated migratory capacity of 4.75% (based on a range of 4.50%-5.00%). Further, the cells still maintained their ability to generate hematopoietic colonies in vitro.

TABLE 6

CD34+ cell viability, growth and CXCR-4 migratory activity 26.0-26.5 hours after Isolex processing of MMH.

|  | Donor | | |
|---|---|---|---|
|  | 1 | 2 | Average |
| CD34+ cell viability (%) | 97.22 | 96.39 | 96.81 |
| CD34$^+$CXCR-4$^+$ cell CXCR-4 migratory activity (%) | 4.50 | 5.00 | 4.75 |
| Hematopoietic CFU/100 CD34+ cells cultured | 28.00 | 14.00 | 21.00 |

Thus, an average of 13.3 hours (based on a range of 13.0 h-13.5 h) after CD34+ cell selection, representing 26.0-26.5 hr post-MMH, the CD34+ cell population had an average viability of 97.24% (based on a range of 96.90%-97.59%), with average CXCR-4 mediated migratory capacity of 7.60% (based on a range of 7.50%-7.70%). At an average of 26.3 hours (based on a range of 26.0 h-26.5 h) following MMH, the average viability of the cells was 96.81% (based on a range of 96.39%-97.2%) and maintained an average CXCR-4-mediated migratory capacity of 4.75% (based on a range of 4.50%-5.00%).

Formulation of the composition of the described invention comprising this product occurred an average of 8 hours (8.63±1.80 N=4) hours after MMH collection, and infusion occurred within 24 hours of MMH.

TABLE 7

CD34+ cell viability as a function of time after MMH: 12-hour in-dating and 48 hour outdating (all time points measured from completion of MMH.)

| Time (h) after MMH (SD) | CD34$^+$ cell viability (%) | | | | |
|---|---|---|---|---|---|
|  | A | B | C | D | Average (SD) |
|  | 98.22 | 97.13 | 97.60 | 99.00 | 97.99 (0.29) |
| 24 | 95.32 | 97.76 | — | — | 96.54 (1.73) |
| 33 | 91.92 | 96.32 | 95.90 | 80.00 | 91.04 (7.62) |

In a subsequent experiment, four (4) MMH products (A-D) were collected and stored at 4° C. for an average of 12.8 hours (based on a range of 12.5 h-13.0 h) before the CD34+ cells were isolated by the Isolex procedure. This group, representing the "12 hour in-date" group (meaning that the product was formulated within the in-date time of about 12 hours), was evaluated for functional viability out-date at "24 hours" (22.9 h±1.63, N=4), "33 hours" (33.38±1.11, N=2), and "48 hours" (48.33±0.82, N=4) post MMH harvest. The data, summarized in Tables 7-9, demonstrate that following MMH, the chemotactic hematopoietic stem cell product comprising enriched CD34+ cells maintains 1) high viability (>90.0% average viability, Table 7), 2) 76.85% (±21.66) of their SDF-1/CXCR-4 mediated migratory ability (Table 8), and 3) their ability to form hematopoietic colonies in vitro (Table 9), respectively.

Table 8 shows SDF-1/CXCR-4 mediated CD34+ cell migration (% migrating CD34+ cells) as a function of time after MMH: 12-hour in-dating and 48-hour outdating (all time points measured from completion of MMH). For the purpose of determining the impact of time post-MMH on the migratory ability of the CD34+ cells, time point "X" was considered the reference point, as this was determined to represent the earliest time point following MMH at which cells reasonably could be expected to be returned to the subject in a finished formulation. The remaining migratory activity at the following time points (Y=33 hours, Z=48 hours) was calculated as percent migratory ability remaining following the 24 hour (X) time point.

TABLE 8

SDF-1/CXCR-4 mediated CD34+CXCR-4+ cell migration (% migrating CD34+ cells) as a function of time after MMH: 12-hour in-dating and 48-hour outdating (all time points measured from completion of MMH).

| Time (h) after MMH | Migrating CD34$^+$CXCR-4$^+$ cells (%) | | | | |
|---|---|---|---|---|---|
|  | A | B | C | D | Average (SD) |
| 24 (X) | 20.00 | 18.50 | 21.50 | 36.00 | 24 (8.09) |
| % Remaining | 100.00 | 100.00 | 100.00 | 100.00 | 100.00 (0) |
| 33 (Y) | 21.80 | 10.50 | — | — | 16.15 (7.99) |
| *% Remaining | 109.00 | 56.76 | — | — | 82.88 (36.94) |
| 48 (Z) | 8.80 | 17.00 | 17.50 | 31.00 | 18.58 (9.19) |
| @% Remaining | 44.00 | 91.89 | 81.40 | 86.00 | 75.85 (21.66) |

*= (Y ÷ X) × 100%
@= (Z ÷ X) × 100%

Table 9 shows the number of colony forming units (CFU) per 100 viable CD34+ cells plated as a function of time after MMH: 12-hour in-dating and 48 hour-out-dating (all time points measured from completion of MMH).

TABLE 9

CFU per 100 viable CD34+ cells plated as a function of time after MMH

| Time (h) after MMH | # of CFU per 100 viable CD34$^+$ cells plated | | | | |
|---|---|---|---|---|---|
|  | A | B | C | D | Average (SD) |
| 24 | 13.00 | 30.00 | 37.00 | 39.00 | 29.75 (11.81) |

TABLE 9-continued

CFU per 100 viable CD34+ cells plated as a function of time after MMH

| Time (h) after MMH | # of CFU per 100 viable CD34⁺ cells plated | | | | Average (SD) |
|---|---|---|---|---|---|
| | A | B | C | D | |
| 33 | 12.00 | 34.00 | — | — | 23.00 (15.56) |
| 48 | 15.00 | 30.00 | 20.00 | 8.00 | 28.25 (14.57) |

In an attempt to extend both the in-date and out-date stability parameters for the chemotactic hematopoietic stem cell product of the described invention comprising CD34+ cells from 12-hours (in-date) and from 48-hours (out-date) (12/48), respectively, to 24-hours (in-date) and 72-hours (outdate) (24/72), respectively, CD34 cells were purified about 12 hours after MMH harvest (12 hour in-date) and about 24 hours after MMH harvest (24 hour in-date) and analyzed for functional viability at about 48 hours and at about 72 hours total time from MMH to time of testing/anticipated infusion (48 hour out-date and 72 hour out-date, respectively). Specifically, the functional viability characteristics of two MMH/chemotactic hematopoietic stem cell products of the described invention were evaluated at 48 hours and 72 hours. The resulting data were further compared to the same indices derived at the previous 12/48 time points (Tables 7-9).

Tables 10-12 show that at 33 hours (based on 32.5±0.71, N=2), 48 hours (based on one data point at 49 hours), and at 72 hours (based on 72.5 h±0.71, N=2), the isolated CD34+ cells of the chemotactic hematopoietic stem cell product of the described invention maintained 1) over 90% viability (Table 10), 2) 102.19±32.69% of their SDF-1/VEGF/CXCR-4 mediated migratory ability (Table 11), and 3) their ability to generate hematopoietic colonies in vitro (Table 12).

TABLE 10

CD34+ cell viability as a function of time after MMH: 24-h in-dating and 72-h outdating (all time points measured from completion of MMH)

| Time (h) after MMH | CD34⁺ cell viability (%) | | Average (SD) |
|---|---|---|---|
| | A | B | |
| 33 | 98.00 | 99.00 | 98.50 (0.71) |
| 48 | — | 97.00 | 97.00 (—) |
| 72 | 91.00 | 97.00 | 94.00 (4.24) |

TABLE 11

SDF-1/CXCR-4 mediated CD34+ cell migration (% population of migrated CD34+ cells as a function of time after MMH): 24-h in-dating and 72-h outdating (all time points measured from completion of MMH)

| Time (h) after MMH (SD) | Migrating CD34⁺ cells (%) | | Average (range) |
|---|---|---|---|
| | A | B | |
| 33 | 8.20 | 14.05 | 11.13 (2.93) |

TABLE 11-continued

SDF-1/CXCR-4 mediated CD34+ cell migration (% population of migrated CD34+ cells as a function of time after MMH): 24-h in-dating and 72-h outdating (all time points measured from completion of MMH)

| Time (h) after MMH (SD) | Migrating CD34⁺ cells (%) | | Average (range) |
|---|---|---|---|
| | A | B | |
| % Remaining | 100.00 | 100.00 | 100.00 (0.00) |
| 48 | — | 18.61 | 18.61 (—) |
| % Remaining | — | 132.46 | 132.46 (—) |
| 72 | 5.70 | 18.95 | 12.33 (6.63) |
| % Remaining | 69.51 | 134.88 | 102.19 (32.69) |

The % remaining ratios in Table 11 were determined as in Table 8 above.

TABLE 12

Number of CFU per 100 viable CD34+ cells plated as a function of time after MMH: 24-h in-dating and 72-h outdating (all time points measured from completion of MMH)

| Time (h) after MMH (SD) | # of CFU per 100 viable CD34⁺ cells plated | | Average (range) |
|---|---|---|---|
| | A | B | |
| 33 | 26.00 | 28.50 | 22.25 (1.25) |
| 48 | — | 16.80 | 16.80 (—) |
| 72 | 14.50 | 27.50 | 21.00 (6.5) |

Further evaluation of the functional viability parameters of the chemotactic hematopoietic stem cell product comprising isolated CD34+ cells of the described invention ("clinical product") at 8 hours (8.6 h±1.80, N=4), 12 hours (12.87 h±1.92, N=4), 32 hours (one time point at 33.5 h), 48 hours (47.50 h±2.5, N=2), and 72 hours (71.5 h±0.50, N=2) after MMH shows that after 72 hours, the product retains its 1) viability (Table 13), 2) SDF-1/CXCR-4 mediated migratory ability (Table 14) and 3) ability to form hematopoietic colonies in vitro (Table 15), equivalent to the 24-hour time point.

TABLE 13

Clinical Product Experience: CD34+ cell viability as a function of time after MMH.

| Time (h) after MMH | CD34⁺ cell viability (%) | | | | Average (SD) |
|---|---|---|---|---|---|
| | A | B | C | D | |
| 8 | 98.30 | 99.08 | 90.00 | 96.45 | 95.96 (4.12) |
| 12 | 98.89 | 96.96 | 99.00 | 99.43 | 98.57 (1.10) |
| 33 | — | 93.42 | — | — | 93.42 |
| 48 | — | 93.15 | 91.58 | — | 92.37 (1.11) |
| 72 | — | 91.25 | 89.25 | — | 90.30 (1.48) |

TABLE 14

Clinical Product Experience: SDF-1/CXCR-4 mediated
CD34+ cell migration (% migrating CD34+ cells
as a function of time after MMH)

| Time (h) after MMH | Migrating CD34+ cells (%) | | | | Average (SD) |
|---|---|---|---|---|---|
| | A | B | C | D | |
| 12 (X) | 14.31 | 13.08 | 9.74 | 31.73 | 17.97 (11.34) |
| % Remaning | 100.0 | 100.0 | 100.0 | 100.0 | 100.0 (0) |
| 33 (Y) | — | 6.17 | — | — | 6.17 |
| *% Remaining | — | 47.17 | — | — | 47.17 |
| 48 (Y) | — | 4.88 | 8.21 | — | 6.55 (2.35) |
| *% Remaining | — | 37.30 | 84.29 | — | 60.79 (23.49) |
| 72 (Y) | — | 3.7 | 6.6 | — | 5.15 (2.05) |
| *% Remaining | — | 28.29 | 21.19 | — | 24.74 (3.55) |

*= (Y ÷ X) × 100%

All remaining ratios were calculated as in Table 8 above.

TABLE 15

Clinical Product Experience: # of CFU per 100 viable CD34+
cells plated as a function of time after MMH

| Time (h) after MMH | # of CFU per 100 viable CD34+ cells plated | | | | Average (SD) |
|---|---|---|---|---|---|
| | A | B | C | D | |
| 12. | 98.14 | 33.30 | 24.00 | 22.50 | 44.49 (36.09) |
| 33 | — | 16.50 | — | — | 16.5 |
| 48 | — | 19.56 | 20.50 | — | 20.03 (0.66) |
| 72 | — | 20.45 | 21.19 | — | 20.82 (1.10) |

Based on these data, extension of the in-dating to 24 hours (from 12-hours) and the out-dating to 72 hours (from 48 hours) for the CD34+ cell clinical product of the described invention is justified.

FIG. 1 indicates the equivalence of the functional viability of the chemotactic hematopoietic cell product of the described invention at 72 hours to the same indices evaluated at 48 hours.

Study 3: Catheter Safety.

The viability and potential efficacy of the chemotactic hematopoietic stem cell product of the described invention comprising potent CD34+ cells depends on the cells maintaining their potency as they pass through a catheter. The catheter used in the methods of the described invention has an internal diameter of at least 0.36 mm. Any type of catheter having an internal diameter of at least 0.36 mm may be effective in delivering the pharmaceutical compositions of the described invention.

In one embodiment, the catheter is a balloon catheter. Balloon catheter safety studies were conducted to determine whether high cell concentrations and repeated perfusions adversely affect cell viability, cell recovery or catheter integrity. Non-mobilized peripheral blood progenitors were used in order to obtain an adequate number of cells to perform the analysis. Catheters were assessed for infusion of the cell product of the described invention comprising selected CD34+ cells through the IRA. None of the 0.36 mm internal diameter catheters tested adversely affected CD34+ selected cell viability, growth in culture, or mobility in CXCR-4 assays.

TABLE 16

Viability of CD34+ cells before
and after infusions through the catheters.

| Catheter | Condition | Viability (%) | | | | |
|---|---|---|---|---|---|---|
| | | 1 | 2 | 3 | 4 | 5 |
| — | Pre-infusion | 81.45 | | | | |
| Raptor | After 1st infusion | 84.29 | 70.94 | 87.89 | 88.02 | 84.68 |
| | After 2nd infusion | 83.00 | 87.44 | 86.39 | 79.91 | 83.18 |
| Sprinter | After 1st infusion | 93.39 | 91.09 | 84.13 | 88.28 | 81.68 |
| | After 2nd infusion | 91.89 | 91.08 | 84.88 | 77.65 | 77.73 |
| Voyager | After 1st infusion | 94.21 | 86.21 | 83.08 | 77.53 | 69.68 |
| | After 2nd infusion | 88.03 | 84.71 | 79.27 | 78.11 | 76.80 |
| Maverick | After 1st infusion | 90.00 | 89.76 | 90.79 | 85.49 | 81.31 |
| | After 2nd infusion | 90.94 | 87.38 | 81.98 | 80.09 | 85.47 |

As shown in Table 16, in all catheters tested, average CD34+ cell viability was at or above 70% following passage through the catheters.

To demonstrate that infusion of the CD34+ cell product does not pose any safety breach of the catheter used and that a significant percentage of cell product does not adhere to the interior walls of the catheter, catheters were challenged with repeat infusions of a CD34+ cell product having a considerably higher cell concentration than that used clinically. Four brands of catheters (Sprinter, Voyager, Maverick and Raptor) were evaluated using 5 catheters of each type. Non-mobilized apheresis products were used in order to obtain an adequate number of cells to perform the analysis. A cell concentration greater than three times that planned as treatment doses for the trial, i.e., 160×10$^6$ nucleated cells containing CD34+ cells in 10 ml of infusion solution, was passed twice through each catheter. The average. CD34+ cell recovery was 100.59% (based on a range of 76.99% to 228.70%) following passage through the catheters.

All twenty catheters were tested for integrity using a methylene blue dye leak test after two perfusions with the nucleated cells. There was no evidence of leakage and the contact points and catheter tips were normal upon inspection.

As shown in Tables 17a and 17b, the effect on the cells of their perfusion through a catheter appears to be independent of catheter model and make among those catheters tested and was independent of the amount of time the cells were stored either prior to processing and/or after CD34+ cell selection and prior to perfusion, resulting in a final formulation containing an average recovery of 96.0% (range 80.8%-102.2%) of the CD34+ cells (Table 17b) and 86.36% of the CD45+ cells perfused through the catheter. Further, the average viability of the cells was 96.5% (range 92.5%-98.6%, N=16); the cells maintained both CXCR-4 migratory capacity (data not shown) and their ability to form hematopoietic colonies in methylcellulose (average 25.8 CFU/100 cells seeded (range 21.0%-30.5%)

TABLE 17a

CD45 cell recovery and viability after being infused through the catheters.

| Catheter | Condition | 1 Recovery | 1 R'd viab | 2 Recovery | 2 R'd viab | 3 Recovery | 3 R'd viab |
|---|---|---|---|---|---|---|---|
| Raptor | After $1^{st}$ infusion | 69.68% | −1.35% | 78.67% | 2.08% | 72.14% | −4.55% |
|  | After $2^{nd}$ infusion | 97.91% | −8.55% | 81.84% | −4.76% | 142.98% | 3.28% |
| Sprinter | After $1^{st}$ infusion | 76.74% | −0.60% | 68.56% | 4.01% | 72.63% | 5.29% |
|  | After $2^{nd}$ infusion | 78.82% | 2.86% | 85.40% | 0.98% | 90.29% | −1.02% |
| Voyager | After $1^{st}$ infusion | 87.38% | 1.58% | 83.93% | −0.36% | 103.58% | 0.93% |
|  | After $2^{nd}$ infusion | 82.70% | 7.01% | 69.34% | 15.90% | 69.54% | 10.40% |
| Maverick | After $1^{st}$ infusion | 73.97% | 1.58% | 87.01% | 0.42% | 78.31% | 0.69% |
|  | After $2^{nd}$ infusion | 152.35% | −5.06% | 73.44% | 2.78% | 80.85% | −3.92% |

| Catheter | Condition | 4 Recovery | 4 R'd viab | 5 Recovery | 5 R'd viab | Average Recovery | Average R'd viab |
|---|---|---|---|---|---|---|---|
| Raptor | After $1^{st}$ infusion | 80.54% | 1.83% | 73.21% | −2.13% | 74.85% (30.83%) | −0.82% (2.53%) |
|  | After $2^{nd}$ infusion | 107.82% | −8.48% | 94.08% | 0.08% | 104.93% (47.60%) | −3.69% (4.94%) |
| Sprinter | After $1^{st}$ infusion | 73.61% | 6.06% | 66.83% | 8.31% | 71.67% (29.48%) | 4.61% (3.51%) |
|  | After $2^{nd}$ infusion | 82.22% | 6.50% | 91.61% | 0.00% | 85.67% (35.30%) | 1.86% (2.76%) |
| Voyager | After $1^{st}$ infusion | 95.82% | 4.52% | 131.55% | −4.39% | 100.45 (44.39%) | 0.46% (2.91%) |
|  | After $2^{nd}$ infusion | 89.04% | 0.27% | 69.03% | 7.50% | 75.93% (32.11%) | 8.22% (6.09%) |
| Maverick | After $1^{st}$ infusion | 75.53% | 2.61% | 77.22% | 2.95% | 78.41% (32.33%) | 1.65% (1.21%) |
|  | After $2^{nd}$ infusion | 97.10% | −2.97% | 91.11% | −2.07% | 98.97% (49.11%) | −2.25% (2.85%) |
|  | Average of all catheters: |  |  |  |  | 86.36% | 1.26% |

[a]Recovery of CD45+ cells = (# of CD45 cells after infusion ÷ # of CD45 before infusion) × 100%
[b]Reduction of CD45+ cell viability = [1 − (CD45+ cell viability % after infusion ÷ CD45+ cell viability % before infusion)] × 100%

TABLE 17b

CD34 cell recovery and viability after being infused through the catheters.

| Catheter used | Condition | 1 Recovery[a] | 1 R'd viab[b] | 2 Recovery | 2 R'd viab | 3 Recovery | 3 R'd viab |
|---|---|---|---|---|---|---|---|
| Raptor | After $1^{st}$ infusion | 116.49% | −3.48% | 121.62% | 12.91% | 110.89% | −7.91% |
|  | After $2^{nd}$ infusion | 91.66% | 1.53% | 85.18% | −23.26% | 122.47% | 1.71% |
| Sprinter | After $1^{st}$ infusion | 89.19% | −14.66% | 83.34% | −11.83% | 102.72% | −3.29% |
|  | After $2^{nd}$ infusion | 103.52% | 1.61% | 99.82% | 0.01% | 82.11% | −0.89% |
| Voyager | After $1^{st}$ infusion | 81.02% | −15.67% | 96.08% | −5.84% | 90.16% | −2.00% |
|  | After $2^{nd}$ infusion | 106.48% | 6.56% | 81.66% | 1.74% | 95.04% | 4.58% |
| Maverick | After $1^{st}$ infusion | 76.99% | −10.50% | 101.79% | −10.21% | 98.62% | −11.46% |
|  | After $2^{nd}$ infusion | 228.70% | −1.05% | 88.66% | 2.65% | 103.35% | 9.70% |

| Catheter used | Condition | 4 Recovery | 4 R'd viab | 5 Recovery | 5 R'd viab | Average Recovery (SD) | Average R'd viab (SD) |
|---|---|---|---|---|---|---|---|
| Raptor | After $1^{st}$ infusion | 97.55% | −8.06% | 96.14% | −3.97% | 108.54% (45.46%) | −2.10% (7.79%) |
|  | After $2^{nd}$ infusion | 111.33% | 9.21% | 98.96% | 1.78% | 101.92% (43.73%) | −1.81% (11.14%) |
| Sprinter | After $1^{st}$ infusion | 84.57% | −8.39% | 88.65% | −0.28% | 89.69% (37.28%) | −7.69% (6.16%) |
|  | After $2^{nd}$ infusion | 114.87% | 12.05% | 100.45% | 4.84% | 100.15% (42.22%) | 3.52% (4.90%) |
| Voyager | After $1^{st}$ infusion | 82.73% | 4.82% | 89.32% | 14.46% | 87.86% (36.28%) | −0.85% (10.13%) |
|  | After $2^{nd}$ infusion | 94.81% | −0.75% | 91.01% | −10.23% | 93.80% (39.12%) | 0.38% (5.86%) |

TABLE 17b-continued

CD34 cell recovery and viability after being infused through the catheters.

| | | | | | | | |
|---|---|---|---|---|---|---|---|
| Maverick | After 1st infusion | 112.58% | −4.96% | 96.05% | 0.18% | 97.21% (41.34%) | −7.39% (5.34%) |
| | After 2nd infusion | 89.35% | 6.31% | 117.63% | −5.12% | 125.54% (73.48%) | 2.50% (5.33%) |
| | | | Average of all catheters: | | | 100.59% | −1.68% |

[a]Recovery of CD34+ cells = (# of CD34 cells after infusion ÷ # of CD34 before infusion) × 100%
[b]Reduction of CD34+ cell viability = [1 − (CD34+ cell viability % after infusion ÷ CD34+ cell viability % before infusion)] × 100%

Collectively these experiments demonstrate that the serial passage of a chemotactic hematopoietic stem cell product comprising CD34+ cells through a cardiac catheter with an internal diameter of at least about 0.36 mm does not adversely affect either catheter integrity or CD34+ cell potency, i.e., CD34+ cell viability, CFU colony growth, or CD34+ CXCR+ mediated migratory capacity/mobility.

Study 4: Compatibility of the Cell Product with the Catheters

To further test the compatibility of the chemotactic hematopoietic stem cell product comprising CD34+ cells with each of the catheters that may be used for delivery of the cell product in the study, cell products were tested after multiple passages through each catheter type to evaluate the effects of extreme conditions of stress that would be greater than those expected during the treatment protocol.

At 48 hours post-MMH harvest, the chemotactic hematopoietic stem cell product comprising a range of about 5.73×106 CD34+ cells to about 21.10×106 CD34+ cells (i.e., dosages reflective of the treatment cohort) obtained from individual donors was infused sequentially through three catheters of the same brand, one type of catheter for each donor (Sprinter, Voyager or Maverick), and the cell product assessed for CD34+ cell recovery, colony formation and viability.

TABLE 18

CD34+ cell recovery and sterility after sequential infusions through the catheters.

| | | Catheter used | | |
|---|---|---|---|---|
| Condition | Parameter | Sprinter | Voyager | Maverick |
| Pre-infusion | CD34+ cell yield | 9.72 × 10⁶ | 2.11 × 10⁷ | 5.73 × 10⁶ |
| After 1st catheter | CD34+ cell recovery | 111% | 103% | 99% |
| After 2nd catheter | CD34+ cell recovery | 94% | 104% | 97% |
| After 3rd catheter | CD34+ cell recovery | 99% | 99% | 106% |
| | Sterility (aerobic and anaerobic microbes) | Negative | Negative | Negative |

As shown in Table 18, viable, colony forming cells were recovered in all experiments for all three catheters tested (cell recovery 99%, 99% and 106%).

As shown in Table 19, the average viability of the CD34+ cells after passing through the third catheter was 94.000% (based on a range of 93.55%-94.40%) versus 96.01% (based on range of 94.18%-97.93%) of the pre-infusion cell product.

TABLE 19

CD34+ cell viability after sequential infusions through the catheters.

| | CD34+ cell viability | | | |
|---|---|---|---|---|
| Condition | Sprinter | Voyager | Maverick | Average |
| Pre-infusion | 94.18% | 95.91% | 97.93% | 96.01% |
| After 1st catheter | 94.73% | 96.31% | 95.45% | 95.50% |
| After 2nd Catheter | 95.34% | 95.72% | 95.01% | 95.36% |
| After 3rd catheter | 93.55% | 94.40% | 94.04% | 94.00% |

As shown in Table 20, colony forming unit (CFU) growth derived from the CD34+ cells after passing through the third catheter was 95.27% (based on a range of 43.47%-163.64%) of the infusion product (i.e., the infused chemotactic hematopoietic stem cell product comprising CD34+ cells).

TABLE 20

CFU growth of CD34+ cells after sequential infusions through the catheters.

| | CFU per 100 CD34+ cells cultured | | |
|---|---|---|---|
| Condition | Sprinter | Voyager | Maverick |
| Pre-infusion | 30.5 | 11.5 | 11.0 |
| After 1st catheter | 22.0 | 14.0 | 22.0 |
| After 2nd catheter | 20.5 | 4.0 | 19.0 |
| After 3rd catheter | 24.0 | 5.0 | 18.0 |
| Recovery from the pre-infused product after the 3rd catheter | 78.69% | 43.47% | 163.64% |
| Average recovery | | 95.27% | |

To determine the effect of catheter perfusion on CD34+ cell mobility and ability to grow in culture, a series of experiments were performed where MMH cells obtained from healthy donors were stored at 4° C. for 12 or 24 hours before initiation of Isolex processing. Isolated CD34+ cell product that had been stored for about 12 hours pre-Isolex processing then were stored at 4° C. until about 36 hours had elapsed from the end of processing, for a total of about 48 hours post MMH. At that time they were assessed for SDF-1/CXCR-4 mobility and CFU growth pre and post perfusion through a 0.36 mm inner diameter (i.d.) cardiac balloon catheter. Similarly, cells that were stored pre-Isolex processing for 24 hours then were stored at 4° C. until 48 hours had elapsed from the end of Isolex processing, for a total of 72 hours, and then assessed.

TABLE 21

12 inbound/48 outbound and 48 hour inbound/72 hour outbound from MMH: SDF-1/CXCR-4 mobility (% population of migrated CD34+ cells) and CFU (per 100 viable CD34+ plated) pre catheter perfusion ("PRE") and post catheter perfusion ("POST")

| Time (h) after MMH Inbound/outbound | SDF-1/CXCR-4 mobility (%) // # of CFU per 100 viable CD34$^+$ cells plated | | | | |
|---|---|---|---|---|---|
| | A | B | C | D | E |
| 12/48 PRE | 2.7 // 14 | 8.8 // 15 | 15.8 // 16 | — | — |
| 12/48 POST | 3.4 // 15 | 18.9 // 13 | 17.6 // 8 | — | — |
| 24/72 PRE | — | — | — | 34 // 37 | 18.9 // 27.5 |
| 24/72 POST | | | | 34 // 43 | 23.5 // 24 |

The results in Table 21 demonstrate that neither CD34+ CXCR-4-mediated cell mobility nor the cell's ability to grow in culture at any of the time points tested was affected adversely by perfusion through a catheter having an internal diameter of at least 0.36 mm.

The Stabilizing Effect of Serum

The following data confirm the importance of the stabilizing effect of serum to the migratory capability of the selected CD34+ cells.

As shown in Table 22, no CXCR-4 migratory activity was observed for all samples tested including the pre-catheter infusion samples when the composition comprising a chemotactic hematopoietic stem cell product was formulated without serum.

TABLE 22

Chemotaxis of CD34+ cells after sequential infusions through the catheters in the absence of serum.

| | Migration (%) | | |
|---|---|---|---|
| Condition | Sprinter | Voyager | Maverick |
| Pre-infusion | 0.0 | 0.0 | 0.1 |
| After 1st catheter | 0.0 | 0.0 | 0.0 |
| After 2nd catheter | 0.0 | 0.0 | 0.1 |
| After 3rd catheter | 0.0 | 0.0 | 0.0 |

FIGS. 2 and 3 further illustrate that Isolex selected CD34+ cells retain their migratory capacity longer when formulated in the presence of human serum. Following Isolex processing, the bone marrow derived hematopoietic stem cell product comprising selected CD34+ cells was formulated either in (1) phosphate buffered saline (Dulbecco's phosphate buffered saline, Ca++, Mg++ Free (Baxter Cat. No. EDR9865) ("PBS") containing 1% human serum albumin, 25 U/ml of heparin sodium and various concentrations (about 0%, about 10%, about 20%, or about 70%) of autologous serum; or (2) normal saline (0.9%) containing 1% human serum albumin, 25 U/ml of heparin sodium and (about 0% or about 10%) autologous serum. SDF-1/CXCR-4 mediated CD34+ cell migratory capacity was evaluated at different times during final product storage (at 2° C.-8° C.) and after passing the cells through the catheter at the same rate and duration as anticipated by the clinical protocol. None of these formulations affected CD34+ cell viability or the recovery of CD34+ cells after they had been passed through the catheter.

Regardless of whether the chemotactic hematopoietic cell products comprising selected CD34+ cells was (i) formulated either in PBS-serum or in saline-serum and (ii) either passed through the catheter immediately or passed through the catheter after a prolonged stability testing storage interval at about 4° C. to about 8° C., they maintained an average of 96.6% viability (range 92.5%-98.6%) and an average CXCR-4-mediated migratory capacity of 11.4% (range 2.4%-30.6%), representing a total time from harvest to mobility analysis of up to 48 hours.

As shown in FIG. 2 panel (a), cells formulated in PBS alone at about 25 hours retained about 10% of their CXCR-4 migratory capacity, which dropped off to near 0 at about 48 hours. As shown in panel (b), cells formulated in normal saline alone retained little, if any, of their migratory capacity. As shown in panels (c) and (d), cells formulated with PBS containing at least about 10% serum retained about 10-15% of their migratory capacity for up to about 55 hours (c), while cells formulated with saline and at least about 10% serum retained about 20% of their migratory capacity for up to about 50 hours. As shown in panels (e) and (f), cells retained a higher migratory capacity for a longer duration in PBS supplemented with even higher concentrations of serum.

As shown in FIG. 3, the product of the described invention comprising selected CD34+ cells when formulated in 10% serum, retained 14.25%, <1%, 6%, and 5.8% of its CD34+CXCR4-mediated migratory capacity about 24, about 32, about 48 and about 56 hours after harvest, respectively. FIG. 3 further shows that the product of the described invention comprising selected CD34+ cells when formulated in 20% serum retained 18.25%, 10.25%, 17% and 11% of its CD34+-CXCR-4-mediated migratory capacity about 24, about 32, about 48 and about 56 hours after harvest, respectively. The term "stabilizing amount" as used herein therefore refers to the amount of serum that, when included in the formulation of the product of the described invention comprising selected CD34+ cells, enables these cells to retain their CXCR-4 mediated chemotactic activity and hematopoietic colony forming ability.

As shown in Table 23, CD34+CXCR-4+ cells obtained from healthy volunteers and from patients to which autologous serum was added maintained their motility out to 72 hours. CD34+ cells were isolated from the bone marrow of healthy volunteers and of patients by the mini-bone marrow harvest procedure as described in Example 3 under identical conditions; and the chemotactic hematopoietic stem cell product was created as described in Examples 4 and 5. The products then were formulated with or without >20% autologous serum, and tested at 24, 48 and 72 hours. As shown in column 2, CXCR-4 cell mobility of CD34+CXCR-4+ cells obtained from healthy volunteers, when formulated without serum, decreased 72% after 48 hours. As shown in column 3, CXCR-4 cell mobility of CD34+CXCR-4+ cells obtained from healthy volunteers, when formulated with serum showed no change in mean CD34+CXCR-4+ cell motility, meaning that the serum stabilizes SDF-1/CXCR-4 motility. Column 4 shows that CD34+CXCR-4+ cells obtained from patients showed less motility than did cells from healthy volunteers, but that the motility of the CD34+CXCR-4+ cells was maintained out to 72 hours.

TABLE 23

Mean CD34+ Cell Mobility and % Change Over Time.

| Hours | Volunteers[†] (N)[††] | Volunteers With Serum[§] | Patients With Serum |
|---|---|---|---|
| | Mean CD34+ Cell Mobility % | | |
| 24 | 14.6 [1](4) | 18.1 (6) | 12.8 (6) |
| 48 | 3.2 (4) | 19.7 (8) | 4.7 (3) |
| 72 | ND[#] | 22.1 (7) | 4.6 (5) |
| | Mean % Change (range)** | | |
| 48 | ↓72 (↓53-↓84) | ↓0.6 (↓16-↑28) | ↓57 (↓13-↓93) |
| 72 | ND | ↑9.6 (↓30-↑85) | ↓68 (↓48-↓86) |

*Hours from bone marrow aspiration
[†]CD34+ cells suspended in PBS only
[††]Number of individuals tested
[§]CD34+ cells suspended in PGS and autologous serum
[1]% CD34+ migrating to lower chamber
[#]Not Done
**Sum of % change of each experiment/number of experiments Study 5: Final Product Sterility Testing Due to the limited yield of CD34+ cells obtained from a 300-ml MMH, final cell product sterility is assessed using the supernatant removed from the final product formulation in order to preserve cell product for infusion. Supernatant samples are loaded into the syringes in a manner identical to that used to load the cell product into the syringes used for infusion (see supra).

To demonstrate that such a sample is representative of the final cell product formulation, we inoculated selected CD34+ cells in infusion solution prior to centrifugation of the final product with C. sporogenes (13 CFU/ml), P. aeruginosa (2 CFU/ml), S. aureus (18 CFU/ml), A. niger (17 CFU/ml), C. albicans (3 CFU/ml) and B. subtilis (17 CFU/ml) (See table 24). After centrifugation, the sterility of both cell pellet and non-cell supernatant fractions was assessed using USP aerobic and anaerobic testing.

TABLE 24

Bacteria and fungi used for the sterility study. Each source microorganism vial prepared by Microbiological Environments contained 400 microbes per ml, but the numbers of CFU derived from each species are varied.

| Microbe | Total # of microbes/ml | Total CFU/ml | Expected CFU/ml of inoculated sample (21 ml) |
|---|---|---|---|
| C. sporogenes | 400 | 279 | 13 |
| P. aeruginosa | 400 | 36 | 2 |
| S. aureus | 400 | 371 | 18 |
| A. niger | 400 | 356 | 17 |
| C. albicans | 400 | 62 | 3 |
| B. subtilis | 400 | 349 | 17 |

As shown in Table 25, both the cell pellet fraction and suspension fractions from all tested samples showed outgrowth of the inoculated microorganisms, while un-inoculated controls showed no growth. Further, no apparent differential growth rate was observed between testing of cell pellet fractions and the suspension fractions for all microorganisms tested. Samples taken before each step of the processing procedure and following the final perfusion through the catheters all tested negative for microbial contamination.

TABLE 25

14-day sterility testing of nucleated cell (NC) samples inoculated with specific species of microorganism (400 microbes in 21-ml NC sample).

| Sample with microbe Inoculated | Medium type | Sample fraction | Test 1 | Test 2 | Test 3 |
|---|---|---|---|---|---|
| C. sporogenes | FTM[a] | Cell pellet | Positive | Positive | Positive |
| | | Suspension | Positive | Positive | Positive |
| S. aureus | FTM | Cell pellet | Positive | Positive | Positive |
| | | Suspension | Positive | Positive | Positive |
| P. aeruginosa | FTM | Cell pellet | Positive | Positive | Positive |
| | | Suspension | Positive | Positive | Positive |
| A. niger | TSB[b] | Cell pellet | Positive | Positive | Positive |
| | | Suspension | Positive | Positive | Positive |
| C. albicans | TSB | Cell pellet | Positive | Positive | Positive |
| | | Suspension | Positive | Positive | Positive |
| B. subtilis | TSB | Cell pellet | Positive | Positive | Positive |
| | | Suspension | Positive | Positive | Positive |
| Positive control: C. sporogenes | FTM | Cell suspension | Positive | | |
| Positive control: S. aureus | FTM | | Positive | | |
| Positive control: P. aeruginosa | FTM | | Positive | | |
| Positive control: A. niger | TSB | | Positive | | |
| Positive control: C. albicans | TSB | | Positive | | |
| Positive control: B. subtilis | TSB | | Positive | | |
| Negative control: No microbes | FTM | Cell suspension | Negative | | |
| Negative control: No microbes | TSB | | Negative | | |

[a]Fluid thioglycollate medium
[b]Tryptic soy broth

Preclinical Study Summary

Collectively, these preclinical data indicate that the manufacturing and testing procedures described are capable of generating adequate numbers of viable cells with adequate stability to withstand shipment and perfusion through the catheter in a manner that should pose no additional safety concerns to the subject other than those associated with the routine use of fluid infusion through the balloon catheter.

Example 11

Preliminary Phase 1 Efficacy Data, with a Single Infusion Date

The following preliminary phase I efficacy data show that within about $10 \times 10^6$ isolated CD34+ cells, there are enough potent CD34+ cells expressing CXCR-4 and having CXCR-4-mediated chemotactic activity to effect a paracrine effect, which affects immediate cell death and later changes consistent with ventricular remodeling.

In accordance with the disclosure in Example 1, a total of 31 subjects were consented, eligible and enrolled in the study. The 31 patients enrolled in the phase I study were randomly assigned to an autologous stem cell harvest treatment group or to a control group five days after an ST elevation myocardial infarction (STEMI) characterized by a prolonged period of hypoperfusion (meaning blocked blood supply) Of the 31 subjects enrolled, 16 were in the treatment group and 15 in the control group. The first subject at each Center was randomized to either treatment or control, and each subsequent patient was enrolled into alternating treatment or control groups. If the subject was assigned to treatment, he/she continued into the Treatment Phase as long as all inclusion/exclusion criteria continued to be met. Subjects assigned to the control group progressed to the follow-up phase. There were no significant differences between groups in any of the baseline demographic or clinical characteristics. Patients enrolled were from 34 to 71 years of age, 87% male, 77% white, 61% in NYHA Class II or III and 49% in NYHA Class I, 74% experienced an infarcted left anterior descending coronary artery, and 55% received a drug eluting stent.

CD34+ cells were isolated from the bone marrow by the mini-bone marrow harvest procedure as described in Example 3 within 5-8 days post stent replacement. Harvested marrow then was shipped to the cGMP cell processing facility as described in Example 4 and isolated as described in Example 5.

As originally planned, and as described in Example 8, there were to be four dosing cohorts (5 million, 10 million, 15 million and 20 million CD34+ cells) in the study. However more than 15 million cells post CD34+ selection could not be obtained reliably. Therefore enrollment terminated at the end of cohort 3 with 15×106 being the highest cell dose assessed.

Following cell product release and cohort assignment, the CD34+ cell product was shipped to the catheterization site for direct infarct related artery infusion. Treatment infusion occurred 6-9 days post stent replacement (and within 48 hours of mini-bone marrow harvest). Subjects were brought to the catheterization laboratory only after the CD34+ cell product had arrived at the facility and had received final release for infusion.

The dosing cohorts consisted of 5 subjects in cohorts 1 and 2, 6 subjects in cohort 3, and 15 control subjects. For cohort 1, the chemotactic hematopoietic stem cell product of the invention comprised $5 \times 10^6$ isolated CD34+ hematopoietic stem cells containing a subpopulation of at least $0.5 \times 10^6$ potent CD34+ cells expressing CXCR-4 and having CXCR-4 mediated chemotactic activity [represented as "5 M"]. For cohort 2, the chemotactic hematopoietic stem cell product of the invention comprised $10 \times 10^6$ isolated CD34+ hematopoietic stem cells containing a subpopulation of at least $0.5 \times 10^6$ potent CD34+ cells expressing CXCR-4 and having CXCR-4 mediated chemotactic activity [represented as "10 M"]. For cohort 3, the chemotactic hematopoietic stem cell product of the invention comprised $15 \times 10^6$ isolated CD34+ hematopoietic stem cells containing a subpopulation of at least $0.5 \times 10^6$ potent CD34+ cells expressing CXCR-4 and having CXCR-4 mediated chemotactic activity [represented as "15 M"]. Control subjects (i.e., those not receiving CD34+ cell infusion) were not expected to have significant improvements in cardiac function (ejection fraction, end systolic and diastolic volumes), or infarct region perfusion at 6 months follow up.

A sterile pharmaceutical composition of the described invention was delivered to each subject in cohorts 1, 2, and 3 parenterally by infusion via the infarct-related artery through a catheter seven to eleven days following the STEMI. The sterile pharmaceutical composition comprised: (a) a therapeutically effective amount of a sterile chemotactic hematopoietic stem cell product, the chemotactic hematopoietic stem cell product comprising an enriched population of isolated CD34+ cells containing a subpopulation of potent cells having chemotactic activity; which, when passed through the catheter remained potent, and (b) a stabilizing amount of serum.

Cardiac function follow-up was performed at 3 and 6 months post-infusion. Cardiac infarct region perfusion was assessed at 6 months post infusion. Both perfusion and functional follow-up testing was assessed by a core lab facility blinded to the study treatment status of each subject. Comparison of these results to baseline indices was performed. Long term follow-up visits are conducted at 12 months and telephone interview with subjects will be made annually at years 2 through 5. For those subjects completing the 2-year follow-up telephone call, no serious adverse events were reported, and thus, there have been no long term safety events detected at this point.

The cardiac performance measures Resting Total Severity Score (RTSS), percent infarct ("% Infarct"), End Systolic Volume (ESV) and Ejection Fraction ("EF") were assessed at 3 months post treatment and at 6 months post treatment and compared with controls to assess efficacy of the compositions compared to controls. Preliminary results are shown in Table 26. SPECT SCAN. As used herein, a single-photon emission computerized tomography (SPECT) scan is a type of nuclear imaging test, which uses a radioactive substance and a special camera to create three dimensional images of the heart to show blood flows to the heart. Generally, the "Resting Total Severity Score (RTSS) is a score based on the amount of dye not taken up in a SPECT SCAN. The data from Resting Total Severity Score represents cardiac perfusion, i.e., blood flow at the microvascular level, and muscle function. In brief, the technetium dye used in a SPECT SCAN is taken up by the heart muscle. If the heart muscle is healthy and takes up the dye, it appears white. If the heart muscle is not healthy, dye uptake is diminished or does not occur at all, and the muscle appears gray to black.

Percent Infarct (MRI).

The size of a heart attack matters for determining how well a patient will recover from the trauma. A patient who has suffered damage to more than 30 percent of the left ventricle of the heart is twice as likely to die within a year from the injury as a patient who has suffered less damage, and bigger infarcts often require more aggressive therapy A computer method calculates the amount of damaged tissue by comparing MRI signal strength between damaged and undamaged tissue. Damaged heart tissue is denser than undamaged tissue because the muscle structure has collapsed, and MRI can distinguish between tissues of varying density. The term "percent (%) infarct" as used herein refers to the infarcted area compared to the rest of the heart. For purposes of this study, a % infarct greater than 20% is considered significant.

Preliminary results are shown in Tables 26 and 27. In order to assess statistical significance, data for the control group and the 5 M group were pooled and data for the 10 M group and 15 M group were pooled (N=7 for each pooled group). The preliminary results for these pooled groups are shown in Table 27. Note that only the SPECT data reached statistical significance; the other measures did not reach statistical significance because of the small numbers of patients involved.

TABLE 26

Phase I Efficacy Data
5M, 10M, 15M and Control
Quantitative Measures of Left Ventricular Function

| Cardiac Function Test | | Control | Treated (5 Million) (N = 5) | Treated (10 Million) (N = 5) | Treated (15 Million) (N = 6) | All Treated (N = 15) | P-Value All Treated vs. Control |
|---|---|---|---|---|---|---|---|
| MRI | | n = 10 | n = 5 | n = 4 | n = 2 | n = 11 | n = 10 |
| LVEF (%) | Baseline | 53 +/− 11 | 47 +/− 13 | 47 +/− 11 | 50 +/− 7 | 48 +/− 10 | |
| | 6 Months | 54 +/− 11 | 47 +/− 13 | 54 +/− 11 | 50 +/− 6 | 50 +/− 11 | |
| | Difference | 1.1 +/− 7.8 | −0.02 +/− 13 | 7 +/− 4 | 0.2 +/− 0.8 | 2.5 +/− 9 | 0.706 |
| EDV (mL) | Baseline | 154.7 +/− 55 | 153.3 +/− 30 | 176.6 +/− 51 | 175.7 +/− 12 | 165.8 +/− 36.1 | |
| | 6 Months | 154.1 +/− 55 | 176.3 +/− 53 | 182.4 +/− 58 | 180.1 +/− 41 | 179.2 +/− 48 | |
| | Difference | −0.56 +/− 20 | 23.1 +/− 37 | 5.83 +/− 29 | 4.39 +/− 29 | 13.4 +/− 31 | 0.244 |
| ESV (mL) | Baseline | 76 +/− 45 | 81 +/− 23 | 97 +/− 46 | 88 +/− 18 | 88 +/− 30 | |
| | 6 months | 74 +/− 44 | 95 +/− 46 | 87 +/− 46 | 91 +/− 32 | 91 +/− 40 | |
| | Difference | −1.84 +/− 17 | 14 +/− 25 | −9.9 +/− 18 | 2.7 +/ 13 | 3.4 +/− 22 | 0.553 |
| Infarct Size[1] | Baseline | 17 +/− 8 | 18.8 +/− 8.6 | 33.2 +/− 14 | 12 +/− 1 | 22.8 +/− 13 | |
| (% of LV Mass) | 6 months | 10 +/− 9 | 16.2 +/− 10.9 | 22 +/− 12 | 11 +/− 2 | 17.5 +/− 11 | |
| | Difference | −7 +/− 5 | −2.6 +/− 5.9 | −10.9 +/− 3 | −0.6 +/− 1 | −5.2 +/− 6 | 0.570 |
| SPECT | | n = 13 | n = 5 | n = 5 | n = 4 | n = 14 | n = 13 |
| RTSS | Baseline | 259 +/− 283 | 714 +/− 658 | 999 +/− 753 | 584 +/− 440 | 779 +/− 620 | |
| (perfusion) | 6 Months | 273 +/− 395 | 722 +/− 521 | 636 +/− 532 | 462 +/− 290 | 617 +/− 449 | |
| | Difference | 14 +/− 210 | 7.8 +/− 216 | −363 +/− 307 | −122 +/− 260 | −162 +/− 293 | 0.087 |

| Cardiac Function Test | | P-Value Control vs 10 + 15 million | Combined Control Control + 5 million | Combined Treated 10 million + 15 million | P-Value Control + 5 million vs 10 + 15 million |
|---|---|---|---|---|---|
| MRI | | | n = 15 | n = 6 | |
| LVEF (%) | Baseline | | 51 +/− 11 | 48 +/− 9 | |
| | 6 Months | | 52 +/− 12 | 53 +/− 9 | |
| | Difference | 0.336 | 1 +/− 9 | 4.5 +/− 5 | 0.352 |
| EDV (mL) | Baseline | | 154 +/− 47 | 176.4 +/− 39.9 | |
| | 6 Months | | 161.5 +/− 53.3 | 181.7 +/− 48.7 | |
| | Difference | 0.617 | 7.3 +/− 28.1 | 5.35 +/− 25.9 | 0.884 |
| ESV (mL) | Baseline | | 78 +/− 38 | 94 +/− 37 | |
| | 6 months | | 81 +/− 44 | 88 +/− 38 | |
| | Difference | 0.666 | 3.6 +/− 21 | −5.7 +/− 17 | 0.341 |
| Infarct Size[1] | Baseline | | 17.3 +/− 8.2 | 26 +/− 16 | |
| (% of LV Mass) | 6 months | | 12 +/− 9.8 | 19 +/− 11 | |
| | Difference | 0.794 | −5.3 +/− 5.8 | −7.5 +/− 5.7 | 0.450 |
| SPECT | | n = 9 | N = 18 | n = 9 | |
| RTSS | Baseline | | 385 +/− 450 | 814 +/− 636 | |
| (perfusion) | 6 Months | | 398 +/− 465 | 559 +/− 426 | |
| | Difference | 0.021 | 13 +/− 205 | −256 +/− 298 | 0.011 |

[1]Infarct size expressed in % of total mass (grams)

TABLE 27

Simple Changes in SPECT Rest Reperfusion Severity
Score by Treatment Group - 6 Month Completers

| | | Baseline | Change from Baseline to 6 Months Post-Infusion | P-value 6 Month Change |
|---|---|---|---|---|
| Treatment Group 1 | N | 5 | 5 | |
| | Mean | 714.200 | 7.8000 | 0.940 |
| | Std. Deviation | 657.850 | 216.054 | |
| | Minimum, Maximum | (0.000, 1787.000) | (−322.000, 222.000) | |
| Treatment Group 2-3 | N | 9 | 9 | |
| | Mean | 814.333 | −255.7778 | 0.033 |
| | Std. Deviation | 635.641 | 297.644 | |
| | Minimum, Maximum | (97.000, 1868.000) | (−859.000, 263.000) | |
| Control Group | N | 13 | 13 | |
| | Mean | 259.000 | 14.462 | 0.808 |
| | Std. Deviation | 282.698 | 210.078 | |
| | Minimum, Maximum | (0.000, 858.000) | (−250.000, 528.000) | |
| Control + Treatment Group 1 | N | 18 | 18 | |
| | Mean | 385.444 | 12.611 | 0.798 |
| | Std. Deviation | 449.728 | 205.293 | |

TABLE 27-continued

Simple Changes in SPECT Rest Reperfusion Severity
Score by Treatment Group - 6 Month Completers

|  | Baseline | Change from Baseline to 6 Months Post-Infusion | P-value 6 Month Change |
|---|---|---|---|
| Minimum, Maximum | (0.000, 1787.000) | (−322.000, 528.000) | |

Note 1:
p-values estimated from paired differences t-tests. 95% confidence interval from t-distribution.

As for Resting Total Severity Score, Table 27 shows that for the 5M and control pooled group, the change in Resting Total Severity Score after 6 months was +12.6, indicating that the infarct area grew in these patients. The Resting Total Severity Score data further shows that patients in the 10M and 15M groups had bigger infarct areas at risk. The 10 M and 15M group showed a drop of 31.4% in infarct size with a p of <0.01. Based on this data, infusion of at least 10×106 isolated CD34+ hematopoietic stem cells containing a subpopulation of at least 0.5×106 potent CD34+ cells expressing CXCR-4 and having CXCR-4 mediated chemotactic activity results in a statistically significant improvement in infarct area perfusion.

The RTSS data for nontreated control subjects show neither neoangiogenesis or prevention of cell death. When subjects were treated with a subtherapeutic dose of cells (i.e., $5 \times 10^6$ CD34+ cells containing a subpopulation of at least $0.5 \times 10^6$ potent CD34+ cells expressing CXCR-4 and having CXCR-4 mediated chemotactic activity), RTSS data showed neither neoangiogenesis or prevention of cell death. Improvement in RTSS was seen only in subjects treated with $10 \times 10^6$ or more CD34+ cells containing a subpopulation of at least $0.5 \times 10^6$ potent CD34+ cells expressing CXCR-4 and having CXCR-4 mediated chemotactic activity. This dose therefore is the minimal therapeutically-effective dose.

Example 12

Multiple Administrations of Chemotactic Hematopoietic Stem Cell Product to Subjects The blood supply in the peri-infarct ischemic border zones is marginal, placing the cardiomyocytes of the border zone in jeopardy. Multiple infusions of chemotactic hematopoietic stem cell product, by supporting cells in the border zone, can preserve/restore viability of the pen-infarct myocardium.

According to this aspect of the described invention, a first aliquot of the composition is administered at a first infusion date, a second aliquot of the composition is administered at a second infusion date, a third aliquot of the composition is administered at a third infusion date, and so on. The scheduling of infusion dates is determined for a given patient by the treating practitioner according to his/her medical judgment.

According to one embodiment, the first infusion date is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after occurrence of an AMI. According to another embodiment, the first infusion date is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 42 months, at least about 48 months, at least about 54 months, at least about 60 months, at least about 66 months, at least about 72 months, at least about 78 months, at least about 84 months, at least about 90 months, at least about 96 months, at least about 102 months, at least about 108 months, at least about 114 months, at least about 120 months, at least about 126 months, at least about 132 months, at least about 138 months, at least about 144 months, at least about 150 months, at least about 156 months, at least about 162 months, at least about 168 months, at least about 174 months, at least about 180 months, at least about 186 months, at least about 192 months, at least about 198 months, at least about 204 months, at least about 210 months, at least about 216 months, at least about 222 months, at least about 228 months, at least about 234 months, at least about 240 months or more after occurrence of an AMI. According to some embodiments, the first infusion date is at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI.

According to another embodiment, the second infusion date is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after occurrence of an AMI. According to another embodiment, the second infusion date is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 42 months, at least about 48 months, at least about 54 months, at least about 60 months, at least about 66 months, at least about 72 months, at least about 78 months, at least about 84 months, at least about 90 months, at least about 96 months, at least about 102 months, at least about 108 months, at least about 114 months, at least about 120 months, at least about 126 months, at least about 132 months, at least about 138 months, at least about 144 months, at least about 150 months, at least about 156 months, at least about 162 months, at least about 168 months, at least about 174 months, at least about 180 months, at least about 186 months, at least about 192 months, at least about 198 months, at least about 204 months, at least about 210 months, at least about 216 months, at least about 222 months, at least about 228 months, at least about 234 months, at least about 240 months or more after occurrence of an AMI. According to some embodiments, the second infusion date is at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI.

According to another embodiment, the third infusion date is at least about one day, at least about two days, at least about three days, at least about four days, at least about five days, at least about six days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or more after occurrence of an AMI. According to another embodiment, the third infusion date is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 30 months, at least about 36 months, at least about 42 months, at least about 48 months, at least about 54 months, at least about 60 months, at least about 66 months, at least about 72 months, at least about 78 months, at least about 84 months, at least about 90 months, at least about 96 months, at least about 102 months, at least about 108 months, at least about 114 months, at least about 120 months, at least about 126 months, at least about 132 months, at least about 138 months, at least about 144 months, at least about 150 months, at least about 156 months, at least about 162 months, at least about 168 months, at least about 174 months, at least about 180 months, at least about 186 months, at least about 192 months, at least about 198 months, at least about 204 months, at least about 210 months, at least about 216 months, at least about 222 months, at least about 228 months, at least about 234 months, at least about 240 months or more after occurrence of an AMI. According to some embodiments, the first infusion date is at least 3 years, 4 years, 5 years, 6 years, 7 years, 8 years, 9 years, 10 years, 11 years, 12 years, 13 years, 14 years, 15 years, 16 years 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years 37 years, 38 years, 39 years, 40 years or more after occurrence of an AMI.

Eligible subjects/patients presenting with symptoms and clinical findings suggestive of a myocardial infarction and eligible for inclusion in the study will be selected as described in Example 1 and catheterized as described in Example 2. In some embodiments, the nonexpanded, isolated population of autologous mononuclear cells comprising potent CD34+ cells will be acquired from the subject/patient as described in Example 3 and, in some embodiments, the harvested bone marrow will be transported to the processing facility as described in Example 4. CD34+ cells will be selected from the harvested bone marrow product as described in Example 5.

The Isolex 300i system will be used to process the RBC-depleted product or the bone marrow product whose RBC volume is <20 ml according to the following processing steps:
  (i) The bone marrow is washed automatically to remove platelets;
  (ii) CD34 positive (CD34+) cells are labeled specifically for selection by incubation with the Isolex 300i CD34 monoclonal antibody (Mab);
  (iii) Unbound reagent is removed by washing the cell suspension with buffer solution;
  (iv) Sensitized CD34+ cells (meaning CD34+ cells labeled with CD34 Mab) are captured by Dynabeads M-450 Sheep anti-Mouse IgG;
  (v) A selection column is used to separate the magnetically-labeled Dynabeads having captured CD34+ cells from unwanted cells, which are washed through the selection column and collected in the Negative Fraction Bag; and
  (vi) PR34+ Stem Cell Releasing Agent releases CD34+ cells from the column, and the CD34+ cells are collected in the End Product Bag. The system performs several washing steps, disposing of most of the liquid into the Buffer Waste Bag.

The Isolex® selected CD34+ fraction then will be assayed to determine WBC and CD34+ cell yields as described in Example 6. A first aliquot of the chemotactic hematopoietic stem cell product containing at least $10 \times 10^6$ CD34+ cells will be formulated a described in Example 7, transported to the catheterization facility as described in Example 8, and infused into the patient as described in Example 9 at the first infusion date. A plurality of aliquots of the nonexpanded, isolated population of autologous mononuclear cells containing CD34+ cells, which further contain a subpopulation of CD34+/CXCR-4+ cells that have CXCR-4-mediated chemotactic activity will be frozen at −86° C. and cryostored in the vapor phase of a liquid nitrogen freezer for subsequent administration. (see "Cryopreservation Study" below).

CryoPreservation Study.

This study was conducted to evaluate the ability of the Isolex-based portion of the chemotactic hematopoietic stem cell product manufacturing process to effectively enrich for CD34+ cells of the cryopreserved MMH. The protocol has been designed to evaluate the yield, viability, functionality and stability of the CD34+ cells derived from the enrichment of cryopreserved MMH. The study has been designed to evaluate and describe the effect on the chemotactic hematopoietic stem cell product of cryopreservation of the RBC reduced MMH prior to the Isolex-based CD34 selection.

The following experimental conditions have been applied:

(1) Two (2) MMH for each of three (3) replicates in order to provide for adequate cell yield to meet with requirements of the experimental design; with a twenty four (24) hour interval between MMH and commencement of RBC depletion procedure.

(2) Study control: Freshly prepared chemotactic hematopoietic stem cell product, with full product characterization after perfusion of the chemotactic hematopoietic stem cell product through a catheter at 48 and 72 hours after MMH.

(3) Experimental: the chemotactic hematopoietic stem cell product derived from cryopreserved MMH, with full product characterization after perfusion of the chemotactic hematopoietic stem cell product derived from cryopreserved MMH through a catheter at 48 and 72 hours after MMH, minus the time the cryopreserved MMH remains in storage (defined as >24 hours)

Study Design

In order to yield sufficient CD34+ cells to perform the intended experiment, two (2) donors will be required. More than or equal to 80 ml MMH and ≥30 ml of peripheral blood will be collected from each donor.

In Bound Storage:

Samples will be stored at 2 to 8° C. for twenty four (24) hours before commencing the RBC reduction procedure.

Following RBC reduction, the MMH from both donors will be pooled and then divided into two equal fractions. One fraction will be used as a fresh (unfrozen) product control and the other fraction will be used for the cryopreservation test.

For the cryopreservation test, RBC reduced MMH will be frozen in a −86° C. freezer and then cryostored in the vapor phase (≤−150° C.) of a liquid nitrogen freezer (LNF) using the cryoprotectant containing the liquid source Hetastarch (6% Hetastarch in 0.9% Sodium Chloride manufactured by Hospira).

Both control (unfrozen) and cryopreserved (after thaw) samples will be Isolex processed essentially as described in Example 5 above. Samples in two 10 ml syringes will be prepared from the selected CD34+ cells. Full product characterization will be performed at the following time points: (i) After perfusion of the product through a catheter at 48 hours after MMH; and (ii) after perfusion of the product through a catheter at 72 hours after MMH. For the cryopreserved samples, the term "72 hours of collection", for example, means the time from collection to the time of testing, excluding the time elapsed from freezing and cryostorage of the RBC depleted bone marrow.

Key determinants for the CD34+ cell quality of the hematopoietic stem cell product include: (i0 CD34+ cell enumeration and 7-AAD viability; (ii) SDF-1/CXCR-4 mediated CD34+ cell migratory activity; (iii) expression of CXCR-4 cell surface antigen on CD34+ cells; and (iv) growth of hematopoietic progenitor cell colonies (CFU). This experiment will be repeated three times.

Summary of Results

The study was conducted in accordance with the methods described above. All deviations from methodology and materials used are detailed in the related result sections presented below.

Table 28 summarizes the relevant information on the donors of the bone marrow used in this study.

TABLE 28

Age and gender of the bone marrow donors for the cryopreservation study.

|  | Exp 1 | | Exp 2 | | Exp 3 | |
| --- | --- | --- | --- | --- | --- | --- |
| Donor | 1 | 2 | 3 | 4 | 5 | 6 |
| Age | 26 | 26 | 22 | 62 | 32 | 24 |
| Gender | F | F | F | F | F | F |

Table 29 summarizes the sample volume, RBC content and the yield, viability and purity of the cells in the pre-processed MMH following 24-h storage in a 2-8° C. refrigerator.

TABLE 29

Post 24 hours storage at 2-8° C. - Volume, cell yield and quality of MMH.

|  | Exp 1 | | Exp 2 | | Exp 3 | |
| --- | --- | --- | --- | --- | --- | --- |
|  | Donor 1 | Donor 2 | Donor 3 | Donor 4 | Donor 5 | Donor 6 |
| Volume (ml) | 117 | 64 | 106 | 105 | 103 | 113 |
| WBC per µl[#] | 1.39E+04 | 1.26E+04 | 1.39E+04 | 1.44E+04 | 1.94E+04 | 2.45E+04 |
| TNC[#] | 1.62E+09 | 8.03E+08 | 1.47E+09 | 1.51E+09 | 1.99E+09 | 2.76E+09 |
| HCT[#] | 33.85% | 33.40% | 29.10% | 27.85% | 31.60% | 32.60% |
| RBC vol. (ml)[#] | 39.44 | 21.38 | 30.85 | 29.24 | 32.55 | 36.84 |
| CD45+ cell viability* | 91.13% | 91.72% | 90.58% | 93.17% | 94.11% | 95.8% |
| Viable CD34+ cell per µl* | 149.18 | 148.38 | 140.89 | 114.45 | 150.80 | 203.76 |
| CD34+ cell viability* | 94.14% | 98.90% | 98.35% | 97.24% | 98.89% | 98.78% |
| CD34+ cell purity* | 1.44% | 1.32% | 1.23% | 0.97% | 1.21% | 0.88% |

TABLE 29-continued

Post 24 hours storage at 2-8° C. - Volume, cell yield and quality of MMH.

|  | Exp 1 | | Exp 2 | | Exp 3 | |
| --- | --- | --- | --- | --- | --- | --- |
|  | Donor 1 | Donor 2 | Donor 3 | Donor 4 | Donor 5 | Donor 6 |
| CXCR-4 expressing CD34+ cells⁻ | 77.68% | 77.03% | 71.88% | 64.57% | 75.75% | 68.36% |
| Total # of CD34+ cells* | 1.74E+07 | 9.50E+06 | 1.49E+07 | 1.20E+07 | 1.55E+07 | 2.30E+07 |

Determined by hematology analyzer
*Determined by flow cytometric analysis of CD45-FITC/CD34-PE antibodies and 7-AAD staining of the sample
⁻Determined by flow cytometric analysis of CD34-FITC and CXCR-4-PE antibodies staining of the sample In each of the experiments, the MMH from each pair of donors were pooled following RBC reduction.

Table 30 presents the RBC content, viability and cell recovery of pooled MMH after RBC reduction:

TABLE 30

Post RBC reduction - RBC content and cell quality

|  | Exp 1 Donors 1 & 2 | Exp 2 Donors 3 & 4 | Exp 3 Donors 5 & 6 |
| --- | --- | --- | --- |
| RBC volume | 15.35 ml | 13.80 ml | 20.85 ml |
| TNC recovery# | 76.95% | 85.93% | 89.37% |
| CD45+ cell viability | 84.97% | 93.35% | 95.60% |
| CD34 recovery# | 72.89% | 84.00% | 88.36% |
| CD34+ cell viability | 93.99% | 97.92% | 98.95% |
| CXCR-4 expressing CD34+ cells | 71.33% | 64.89% | 74.64% |

As compared to the pre-processed samples

Following RBC reduction, each of the pooled MMH samples was divided into two equal fractions. One was used as a fresh (unfrozen) control and the other one was used for the cryopreservation test.

For cryopreservation, MMH mixed with an equal volume of chilled cryoprotectant was loaded evenly into two 250 ml Cryocyte containers, frozen in a mechanical freezer (–86° C.) and then stored cryopreserved in the vapor phase of a LNF according to the Protocol. Table 31 presents data obtained from post-thawed and washed MMH:

TABLE 31

Post thawed & washed MMH - Cell quality and recovery of cells Cryopreserved Sample Thawed and washed

|  | Exp 1 | Exp 2 | Exp 3 |
| --- | --- | --- | --- |
| Storage duration prior to thaw | 10 days | 8 days | 8 days |
| Wash media | PBS working sol'n* | 2% Dextran~ | 8.3% Dextran@ |
| RBC volume | 0.39 ml | 1.11 ml | 0.38 ml |
| TNC recovery# | 36.11% | 50.73% | 28.61% |
| CD45+ cell viability | 61.85% | 32.18% | 43.97% |
| CD34+ cell recovery# | 52.43% | 46.29% | 15.72% |
| CD34+ cell viability | 94.36% | 86.11% | 81.76% |
| CD34+ cell purity | 2.40% | 1.29% | 1.88% |
| CXCR-4 expressing CD34+ cells | 51.42% | 50.74% | 37.85% |

Key:
As compared to the RBC reduced MMH before cryopreservation.
*PBS Working Solution contained 1% HSA and 0.41% sodium citrate (w/v) in PBS (Ca⁺⁺ and Mg⁺⁺ free). Washing of cells with this solution was performed according to that instructed in the Protocol.
~This wash solution contained 2% Dextran 40, 1% HSA and 0.4% Na citrate in PBS (Ca⁺⁺ and Mg⁺⁺ free). The thawed sample was expanded with 200 ml of this solution and was then washed twice each with 200 ml of this solution. Centrifugation was set for 600 g, 10 minutes at 20° C. The washed cells were resuspended with 150 ml PBS Working Solution for Isolex process.
@This solution contained 8.3% Dextran 40 and 4.2% HSA in saline. The washing procedure was essentially as described for the 2% Dextran 40 wash solution.

Table 32 summarizes the CD34+ cell quality and recovery of the chemotactic hematopoietic stem cell product prepared from the unfrozen and cryopreserved MMH following Isolex processing.

TABLE 32

Post Isolex - Cell quality and recovery of cells

|  | Exp 1 | | Exp 2 | | Exp 3 | |
| --- | --- | --- | --- | --- | --- | --- |
| MMH source | Unfrozen | Frozen | Unfrozen | Frozen | Unfrozen | Frozen |
| CD34+ cell recovery# | 47.28% | 37.88% | 35.94% | 49.29% | 44.05% | 82.25% |
| CD34+ cell viability# | 99.37% | 96.89% | 98.97% | 95.05% | 98.26% | 95.38% |
| CD34+ cell purity | 87.51% | 83.95% | 86.47% | 81.91% | 81.71% | 50.87% |
| Total # of viable CD34+ cells | 4.63E+06 | 1.95E+06 | 4.07E+06 | 2.58E+06 | 7.50E+06 | 2.20E+06 |

As compared to the RBC reduced sample for unfrozen samples and post thawed and washed samples for frozen samples.

Following Isolex processing of each RBC reduced MMH pooled pair, two chemotactic hematopoietic stem cell product ("AMR-001") samples with equal number of CD34+ cells, each in a 10 ml syringe, were prepared. Both AMR-001 samples were stored at 2-8° C. for stability testing. At 48 and 72 hours from MMH (For cryopreserved MMH samples, the time for cryostorage was not included), a prepared AMR-001 was perfused through a balloon dilatation catheter performed in a manner as for a clinical AMR-001. A full CD34+ cell characterization was performed on the perfused AMR-001 samples and the results are presented in Tables 33, 34, 35, and 36. Table 37 shows the balloon dilatation catheter used.

TABLE 33

Post infusion through catheter - CD34+ cell purity, viability and recovery

| | | Catheter perfused AMR-001 | | | |
|---|---|---|---|---|---|
| | MMH source | Unfrozen | | Frozen | |
| Experiment | Time post MMH | 48 h | 72 h | 48 h | 72 h |
| 1 | CD34+ cell recovery# | 101.73% | 92.32% | 91.71% | 69.35% |
| | CD34+ cell viability | 99.08% | 98.13% | 94.98% | 91.80% |
| | CD34+ cell purity | 85.92% | 84.93% | 82.94% | 74.24% |
| | Total # of CD34+ cells | 2.36E+06 | 2.14E+06 | 8.92E+05 | 6.74E+05 |
| 2 | CD34+ cell recovery# | 95.65% | 89.20% | 77.10% | 74.01% |
| | CD34+ cell viability | 98.29% | 97.29% | 89.47% | 82.82% |
| | CD34+ cell purity | 81.49% | 82.42% | 75.30% | 70.50% |
| | Total # of CD34+ cells | 1.95E+06 | 1.81E+06 | 9.96E+05 | 9.56E+05 |
| 3 | CD34+ cell recovery# | 104.17% | 101.99% | 77.35% | 79.12% |
| | CD34+ cell viability | 98.46% | 97.51% | 86.86% | 85.59% |
| | CD34+ cell purity | 83.18% | 82.80% | 47.81% | 43.71% |
| | Total # of CD34+ cells | 3.91E+06 | 3.83E+06 | 8.52E+05 | 8.71E+05 |

As compared with the prepared AMR-001 before perfusion

TABLE 34

Post infusion through catheter - CXCR-4 expressing CD34+ cells (% of total CD34+ cells).

| | MMH source of AMR-001 samples | | | | | |
|---|---|---|---|---|---|---|
| Catheter | Exp 1 | | Exp 2 | | Exp 3 | |
| perfusion | Unfrozen | Frozen | Unfrozen | Frozen | Unfrozen | Frozen |
| 48 h post MMH | 66.52% | 53.31% | 57.64% | 41.35% | 60.14% | 54.16% |
| 72 h post MMH | 73.87% | 53.89% | 56.73% | 44.07% | 64.60% | 50.67% |

TABLE 35

Post infusion through catheter - Migratory CD34+ cells (% of total viable CD34+ cells).

| | MMH source of AMR-001 samples | | | | | |
|---|---|---|---|---|---|---|
| Catheter | Exp 1 | | Exp 2 | | Exp 3 | |
| perfusion | Unfrozen | Frozen | Unfrozen | Frozen | Unfrozen | Frozen |
| 48 h post MMH | 18.81 ± 1.83%* | 5.87 ± 1.98% | 19.67 ± 10.43% | 15.67 ± 2.24% | 24.89 ± 1.93% | 26.66 ± 1.53% |
| 72 h post MMH | (1.07%)# | (1.51%) | (1.06%) | (2.19%) | (1.44%) | (1.56%) |

*SDF-1 induced migration. % of migratory CD34+ cell of total viable CD34+ cells with standard deviation of three replicates.
Natural migration (no SDF-1 added)

TABLE 36

Post infusion through catheter - Number of
CFU per 100 viable CD34+ cells cultured.

| | MMH source of AMR-001 samples | | | | | |
|---|---|---|---|---|---|---|
| | Exp 1 | | Exp 2 | | Exp 3 | |
| perfusion | Unfrozen | Frozen | Unfrozen | Frozen | Unfrozen | Frozen |
| 48 h post MMH | 24 | 15.5 | 31.5 | 14 | 38 | 15.5 |
| 72 h post MMH | 20.5 | 0.05 | 62.5 | 12 | 30.5 | 7 |

TABLE 37

Balloon dilatation catheters used

| Exp | MMH source of the AMR-001 sample | Time of perfusion (Hours of MMH) | Manufacture | Balloon length/dia. | Catalog # | Lot # | Comment |
|---|---|---|---|---|---|---|---|
| 1 | Unfrozen | 48 h | Sprinter | 12/3.5 mm | SPR3512W | 258795 | Outdated |
| | | 72 h | Sprinter | 12/4.0 mm | SPR4012W | 254243 | Outdated |
| | Frozen | 48 h | Sprinter | 15/3.0 mm | SPR3015W | 412090 | Outdated |
| | | 72 h | Voyager | 15/3.0 mm | 1009443-15 | 8111462 | — |
| 2 | Unfrozen | 48 h | Sprinter | 15/3.5 mm | SPR3515W | 443152 | Outdated |
| | | 72 h | Sprinter | 15/3.5 mm | SPR3515W | 443152 | Outdated |
| | Frozen | 48 h | Voyager | 15/3.0 mm | 1009443-15 | 8111462 | — |
| | | 72 h | Voyager | 15/3.0 mm | 1009443-15 | 8092561 | — |
| 3 | Unfrozen | 48 h | Voyager | 15/3.0 mm | 1009443-15 | 8111462 | Reused* |
| | | 72 h | Sprinter | 15/3.0 mm | SPR3015W | 476734 | Outdated |
| | Frozen | 48 h | Sprinter | 15/3.0 mm | SPR3015W | 476734 | Outdated |
| | | 72 h | Sprinter | 15/3.0 mm | SPR3015W | 476734 | Outdated |

*Prior to be used for the $2^{nd}$ time, the catheter and the central lumen were $1^{st}$ washed and flushed with 70% isopropyl alcohol and then with sterile PBS. The central lumen was then injected with air in order to remove the residual liquid inside. The washing procedure was performed inside a bio-safety cabinet.

Discussion

The aim of this study was to evaluate the quality of AMR-001 manufactured from cryopreserved MMH.

Post Isolex CD34+ cell recovery of the AMR-001 manufactured from unfrozen MMH (Control samples) was on average 34.6±4.35% (range 30.3% to 39%) which is within the acceptance range for manufacture of AMR-001 for clinical use. It should be noted that the data presented above are estimated without taking account for the cells removed for the in-process tests, therefore the actual CD34+ cell recovery will be slightly higher than that presented.

Post catheter CD34+ cell recovery was 100.52±4.39% (95.65% to 104.17%) at 48 hours post MMH and 94.50±6.67% (89.20% to 101.99%) at 72 hours post MMH. There was no substantial reduction in viability (Table 33), CXCR-4 expression (Table 34), migratory activity (Table 35) and CFU growth (Table 36) of CD34+ cells at 72 hours post MMH as compared to those monitored at 48 hours post MMH.

For the cryopreservation test, RBC reduced MMH samples were cryopreserved according to PCT protocol for cryopreservation of bone marrow for transplantation where MMH samples mixed with equal volume of cryoprotectant with final concentration of 5% DMSO, 2.5% HSA and 2.1% Hetastarch (from liquid source 6% Hetastarch, Hospira) were frozen at −86° C. and then cryostored in the vapor phase of a LNF.

Post cryopreservation and thaw, the stability, viability, mobility and growth in culture of Isolex selected CD34+ cells is maintained. Thus the frozen-thawed cells meet the criteria for clinical use.

In some embodiments, a chemotactic hematopoietic stem cell product prepared from frozen and thawed aliquots of a sterile nonexpanded, isolated population of autologous mononuclear cells comprising CD34+ cells, which further contain a subpopulation of potent CD34+/CXCR-4+ cells that have CXCR-4-mediated chemotactic activity will be used for infusion. Samples of this chemotactic hematopoietic stem cell product will be removed to be assayed for WBC count, by flow cytometry (for CD34+ cell enumeration and viability), Gram stain, and sterility. The chemotactic hematopoietic stem cell product will be released for infusion within about 48 hours to about 72 hours of thawing of the sterile nonexpanded, isolated population of autologous mononuclear cells only if it meets the following criteria:

CD34+ cell purity of at least about 70%, 75%, 80%, 85%, 90% or 95%;

A negative Gram stain result for the selected positive fraction;

Endotoxin Levels: less than about 0.5 endotoxin units/ml;

Viable CD34+ cell yield of the "Chemotactic hematopoietic stem cell product" meets the required dosing as per the treatment cohort;

CD34+ cells are at least about 70%, 75%, 80%, 85%, 90% or 95% viable by 7-AAD;

USP sterility result for "Positive Fraction Supernatant": negative (14 days later).

Sterility assessment on the stem cell product including gram staining and endotoxin will be performed prior to product release for infusion. USP sterility (bacterial and fungal) culture will be performed and the results will be reported to the principal investigator. In the event of a positive USP sterility result, the subject and attending physician on call will be notified immediately, provided with identification and sensitivity of the organism when available, and documentation of appropriate anti-microbial treatment and treatment outcome will be recorded by the investigative site and the sponsor.

The chemotactic hematopoietic stem cell product prepared from the frozen and thawed autologous mononuclear cells will be formulated a described in Example 7, transported to the catheterization facility as described in Example 8, and infused into the patient as described in Example 9.

It is proposed that administration of a potent dose of CD34+/CXCR-4+ cells that have CXCR-4-mediated chemotactic activity, early or late after occurrence of an acute myocardial infarction according to the described invention can result in a reduction in persistent/chronic and progressive adverse cardiac events, including, but not limited to, premature death, recurrent myocardial infarction, the development of congestive heart failure, significant arrhythmias, and acute coronary syndrome, and the worsening of congestive heart failure, significant arrhythmias, and acute coronary syndrome.

Example 13

Co-Administration of the Chemotactic Hematopoietic Stem Cell Product and Neuregulin 1

Neuregulin 1 (NRG1) is an agonist for receptor tyrosine kinases of the epidermal growth factor receptor family, consisting of ErbB1, 2, 3, and 4. (Fuller, S J, et al., J. Mal. Cell Cariol. 44: 831-54 (2008). Binding of NRG1 to Erb4 increases its kinase activity and leads to heterodimerization with erbB2 or homodimerization with ErbB4 and stimulation of intracellular signal transduction pathways. Id. NFRG1 receptor subunits ErbB2 and ErbB4 also are expressed in differentiated cardiomyocytes. Id. Recently it has been shown in mice that NRG1 induces proliferation of differentiated mononucleated cardiomyocytes in vivo by inducing differentiated cardiomyocytes to leave proliferative quiescence. Bersell, et al (Bersell, K. et al., Cell 138: 257-70 (2009). Undifferentiated stem and progenitor cells did not contribute to this proliferation. (Id). Using a mouse model in which the left anterior descending coronary artery (LAD) of two month old mice was ligated permanently and NRG1 administered daily one week later for 12 weeks, it was shown that administration of NRG1 for 12 weeks resulted in a sustained improvement in myocardial function, determined by ejection fraction, a reduced infarct scar size, and attenuation of cardiomyocyte hypertrophy. (Id).

Following acute myocardial infarction, in addition to necrotic cell death as a consequence of ischemia, ongoing apoptotic cell death and cardiomyocyte hibernation collectively lead to a decrement in cardiac function that can worsen over time and ultimately causing major adverse cardiac events. Once lost, cardiomyocytes are unable to significantly regenerate to restore cardiac function. Carbon 14 dating of cardiomyocytes show the regenerative capacity of cardiac muscle to be less than 1% annually (Bergman O. Science. 2009; 324:98-101). The described invention demonstrates the prevention of cardiomyocyte loss after AMI through enhancement of perfusion and prevention of apoptosis. Further restoration of cardiac function requires significantly increasing the regenerative capacity of cardiomyocytes. Regenerating cardiomyocytes will require adequate perfusion or will suffer the consequences of ischemia including hibernation and apoptosis.

It is proposed that the combination of the described invention with significant augmentation of the natural regenerative capacity of cardiomyocytes would be synergistic in restoring cardiac function after AMI and preventing major adverse cardiac events. Co-administration therefore of the chemotactic hematopoietic stem cell product of the described invention with neuregulin 1 is proposed as a therapeutic capable of restoring cardiac function after AMI through increasing perfusion, which prevents apoptotic cardiomyocyte cell death and rescues cardiomyocytes from hibernation, and by providing the infrastructure needed for generation of new cardiomyocytes to replace lost cardiomyocytes.

Recombinant human neuregulin 1 will be obtained from commercial sources. (Cell Sciences, Novus Biologicals, R & D Systems, Raybiotech, Inc., Shenandoah Biotechnology, Spring Bioscience).

Increased doses of neuregulin 1 will be admixed with the chemotactic hematopoietic stem cell product of the described invention and tested in vitro after passage through a catheter for product viability, sterility, purity and potency, meaning viability, migratory capacity and CFU-growth, after storage for up to 72 hours. If potency, purity and viability are maintained, a preclinical experiment is proposed in which purified, sterile human derived CD34+ cells containing a subpopulation of potent CD34+ cells expressing CXCR-4 and having CXCR-4-mediated chemotactic activity will be infused via the tail vein in Nod SCID mice after coronary artery ligation and relief (induced AMI model). The effect of this treatment on cardiac perfusion, cardiac muscle function, histopathology, apoptosis, and scarring will be assessed post infusion and compared to controls (i.e., Nod SCID mice not receiving cells). Prior studies have demonstrated an improvement in perfusion, human neoangiogenesis, prevention of apoptosis, and preserved cardiac function in treated versus control animals. Next, increasing doses of neuregulin 1 will be added to the purified, sterile human derived CD34+ cells containing a subpopulation of potent CD34+ cells expressing CXCR-4 and having CXCR-4-mediated chemotactic activity of the described invention and the results will be compared to control animals and to animals treated with the purified, sterile human derived CD34+ cells containing a subpopulation of potent CD34+ cells expressing CXCR-4 and having CXCR-4-mediated chemotactic activity of the described invention alone.

If pre-clinical models show a potential synergistic beneficial effect with the purified, sterile human derived CD34+ cells containing a subpopulation of potent CD34+ cells expressing CXCR-4 and having CXCR-4-mediated chemotactic activity of the described invention combined with neuregulin 1, a dose escalation safety and efficacy trial in sustaining and in AMI patients is proposed. For this study, patients will receive the purified, sterile human derived CD34+ cells containing a subpopulation of potent CD34+ cells expressing CXCR-4 and having CXCR-4-mediated chemotactic activity of the invention with or without neuregulin 1. Neuregulin I will be administered in increasing doses to determine (i) the mean therapeutic dose (MTD) and (ii) whether perfusion and cardiac function are enhanced by the combination of neuregulin 1 and the purified, sterile human derived CD34+ cells containing a subpopulation of potent CD34+ cells expressing CXCR-4 and having CXCR-4-mediated chemotactic activity of the described invention compared to the purified, sterile human derived CD34+ cells containing a subpopulation of potent CD34+ cells expressing CXCR-4 and having CXCR-4-mediated chemotactic activity of the described invention alone.

While the described invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the described invention. All such modifications are intended to be within the scope of the claims appended hereto.

What is claimed is:

1. A method for treating progressive decline in heart muscle function due to myocardial ischemia, which comprises
   (a) determining eligibility of the subject by clinically evaluating the heart muscle function;
   (b) administering parenterally to the subject through a catheter on a first infusion date a sterile pharmaceutical composition comprising a therapeutic amount of a chemotactic hematopoietic stem cell product comprising:
      (i) a nonexpanded, isolated population of autologous mononuclear cells enriched for CD34+ cells, which further contains a subpopulation of potent CD34+/CXCR-4+ cells that have CXCR-4-mediated chemotactic activity; and
      (ii) a stabilizing amount of serum, wherein the stabilizing amount of serum is at least 10% (v/v) and is effective to retain the CXCR-4-mediated chemotactic activity and hematopoietic colony forming activity of the subpopulation of CD34+/CXCR-4+ cells;
   the composition being characterized as having the following properties for at least 24 hours following acquisition of the mononuclear cells when tested in vitro after passage through the catheter:
   (1) at least 70% of the cells in the composition are CD34+ cells,
   (2) the subpopulation of CD34+/CXCR-4+ cells have CXCR-4-mediated chemotactic activity move in response to SDF-1,
   (3) at least 70% of the cells in the composition are viable, and
   (4) can form hematopoietic colonies in vitro;
   wherein the therapeutic amount of the chemotactic hematopoietic stem cell product comprises at least 10 million isolated CD34+ cells comprising at least 0.5× $10^6$ potent CD34+/CXCR-4+ cells that have CXCR-4-mediated chemotactic activity and that move in response to SDF-1; and
   (c) repeating steps (a) through (b) on at least one or more infusion dates during the subject's lifetime;
   thereby treating the progressive decline in heart muscle function due to myocardial ischemia by:
      improving myocardial perfusion of the myocardium and;
      reducing apoptosis of existing cardiomyocytes in the myocardium, thereby preserving their function.

2. The method according to claim 1, wherein the myocardial ischemia develops after an acute myocardial infarction.

3. The method according to claim 2, wherein a first infusion date comprises a specific time interval defined by a first time and a second time, and wherein the first time is after peak inflammatory cytokine cascade production in an infarcted area and the second time is before myocardial scar formation in an infarcted area.

4. The method according to claim 3, wherein the first time of the first infusion date is at least about 5 days post-infarction.

5. The method according to claim 3, wherein a second infusion date is at least 30 days after occurrence of an acute myocardial infarction.

6. The method according to claim 3, wherein peak inflammatory cytokine cascade production is determined by measuring a level of at least one inflammatory cytokine in plasma and or urine.

7. The method according to claim 2, wherein the therapeutic amount of the chemotactic hematopoietic stem cell product is effective to treat the myocardium that extends beyond an infarct region of myocardium after the acute myocardial infarction (peri-infarct zone).

8. The method according to claim 7, wherein the therapeutic amount of the chemotactic hematopoietic stem cell product is effective to treat cardiomyocyte cell death in the peri-infarct border zone, hypoperfusion in the peri-infarct border zone, myocardial hibernation in the peri-infarct border zone, or a combination thereof, relative to controls.

9. The method according to claim 2, wherein the therapeutic amount of the chemotactic hematopoietic stem cell product is effective to decrease infarct area, decrease infarct mass, or a combination thereof, relative to controls.

10. The method according to claim 2, wherein the progressive decline in heart muscle function comprises development of congestive heart failure, development of significant arrhythmias, development of an acute coronary syndrome, or a combination thereof.

11. The method according to claim 10, wherein worsening of congestive heart failure, worsening of significant arrhythmias, worsening of acute coronary syndrome, or a combination thereof can lead to premature death without treatment.

12. The method according to claim 10, wherein the development of acute coronary syndrome comprises recurrent myocardial infarction.

13. The method according to claim 2, wherein the progressive decline in heart muscle function comprises a progressive decline in heart muscle function following the acute myocardial infarction.

14. The method according to claim 2, wherein the improvement in myocardial perfusion of the myocardium comprises reducing apoptotic cardiomyocyte cell death and rescuing cardiomyocytes from hibernation in the myocardium.

15. The method according to claim 1, wherein the catheter has an internal diameter of at least about 0.36 mm.

16. The method according to claim 1, wherein the administering is through the catheter into myocardium, through the catheter intravascularly, or a combination thereof.

17. The method according to claim 1, wherein the pharmaceutical composition further includes at least one active agent that is compatible with both components (i) and (ii) of the composition.

18. The method according to claim 17, wherein the active agent is selected from the group consisting of a cytokine, a diuretic, an anti-arrhythmic agent, a tyrosine kinase receptor agonist, an anti-anginal agent, a vasoactive agent, an anticoagulant agent, a fibrinolytic agent, and a hypercholesterolemic agent.

19. The method according to claim 18, wherein the tyrosine kinase receptor agonist is human neuregulin 1.

20. The method according to claim 18, wherein the cytokine is a hematopoietic stem cell mobilizing agent.

21. The method according to claim 20, wherein the hematopoietic stem cell mobilizing agent is G-CSF, GM-CSF, or a combination thereof.

22. The method according to claim 18, wherein the vasoactive agent is an angiotensin converting enzyme inhibitor.

23. The method according to claim 18, wherein the antiarrhythmic agent is a beta blocker.

24. The method according to claim 1, wherein the subject is a revascularized subject.

25. The method according to claim 1, wherein step (a) comprises measuring inflammatory cytokines, cardiac biomarkers, or both.

26. The method according to claim 25, wherein the level of inflammatory cytokines is measured immunochemically.

27. The method according to claim 1, wherein the chemotactic hematopoietic stem cell product of the composition of step (b) is a frozen and thawed chemotactic hematopoietic stem cell product.

28. The method according to claim 1, wherein the myocardial ischemia is a transient ischemia or a chronic myocardial ischemia.

29. The method according to claim 1, wherein the myocardial ischemia is a peri-infarct border zone ischemia.

* * * * *